US009901567B2

(12) United States Patent
Beusker et al.

(10) Patent No.: US 9,901,567 B2
(45) Date of Patent: Feb. 27, 2018

(54) SUBSTITUTED CC-1065 ANALOGS AND THEIR CONJUGATES

(71) Applicant: SYNTARGA B.V., Nijmegen (NL)

(72) Inventors: Patrick Henry Beusker, Nijmegen (NL); Henri Johannes Spijker, Nijmegen (NL); Johannes Albertus Frederikus Joosten, Nijmegen (NL); Tijl Huijbregts, Nijmegen (NL); Franciscus Marinus Hendrikus De Groot, Nijmegen (NL)

(73) Assignee: Syntarga B.V., Nijmegen (NL)

(*) Notice: Subject to any disclaimer, the term of this patent is extended or adjusted under 35 U.S.C. 154(b) by 0 days.

(21) Appl. No.: 14/174,794

(22) Filed: Feb. 6, 2014

(65) Prior Publication Data

US 2015/0216844 A1    Aug. 6, 2015

Related U.S. Application Data

(62) Division of application No. 12/671,609, filed as application No. PCT/NL2007/050384 on Aug. 1, 2007, now Pat. No. 8,680,293.

(51) Int. Cl.
| | |
|---|---|
| C07D 209/56 | (2006.01) |
| A61K 38/00 | (2006.01) |
| A61K 31/40 | (2006.01) |
| A61K 31/404 | (2006.01) |
| A61K 47/68 | (2017.01) |

(52) U.S. Cl.
CPC ........ *A61K 31/404* (2013.01); *A61K 47/6803* (2017.08); *A61K 47/6851* (2017.08)

(58) Field of Classification Search
USPC ........................ 548/427; 514/19.2, 19.3, 411
See application file for complete search history.

(56) References Cited

U.S. PATENT DOCUMENTS

| | | | |
|---|---|---|---|
| 5,475,092 | A | 12/1995 | Chari et al. |
| 5,502,068 | A | 3/1996 | Lown et al. |
| 5,585,499 | A | 12/1996 | Chari et al. |
| 5,629,430 | A | 5/1997 | Terashima et al. |
| 5,646,298 | A | 7/1997 | Powell |
| 5,662,911 | A | 9/1997 | Huber et al. |
| 5,739,350 | A | 4/1998 | Kelly et al. |
| 5,843,937 | A | 12/1998 | Wang et al. |
| 5,846,545 | A | 12/1998 | Chari et al. |
| 7,705,045 | B2* | 4/2010 | De Groot ........... A61K 47/4813 514/483 |
| 8,012,978 | B2 | 9/2011 | Zhao et al. |
| 8,680,293 | B2 | 3/2014 | Beusker et al. |
| 8,889,868 | B2 | 11/2014 | Beusker et al. |
| 8,940,784 | B2 | 1/2015 | Beusker et al. |
| 9,421,278 | B2 | 8/2016 | Dokter et al. |
| 9,427,480 | B2 | 8/2016 | Santin et al. |
| 9,629,924 | B2 | 4/2017 | Beusker et al. |

| | | | |
|---|---|---|---|
| 2004/0033962 | A1 | 2/2004 | Tietze et al. |
| 2004/0120958 | A1 | 6/2004 | Bander et al. |
| 2006/0116422 | A1* | 6/2006 | De Groot ........... A61K 47/4813 514/483 |
| 2006/0233794 | A1* | 10/2006 | Law .................. A61K 47/48338 424/144.1 |
| 2009/0010945 | A1 | 1/2009 | Alley et al. |
| 2009/0111805 | A1 | 4/2009 | Morris et al. |
| 2009/0162372 | A1 | 6/2009 | King et al. |
| 2012/0214864 | A1 | 8/2012 | Richer et al. |
| 2013/0095172 | A1 | 4/2013 | Alavattam et al. |
| 2013/0224227 | A1 | 8/2013 | Beusker et al. |
| 2016/0008486 | A1 | 1/2016 | Dokter et al. |
| 2016/0008487 | A1 | 1/2016 | Santin et al. |
| 2016/0052880 | A1 | 2/2016 | Beusker et al. |
| 2016/0324979 | A1 | 11/2016 | De Roo et al. |
| 2017/0007717 | A1 | 1/2017 | Santin et al. |
| 2017/0014525 | A1 | 1/2017 | Dokter et al. |
| 2017/0080103 | A1 | 3/2017 | Ariaans et al. |
| 2017/0145006 | A1 | 5/2017 | Huijbregts et al. |

FOREIGN PATENT DOCUMENTS

| | | |
|---|---|---|
| EP | 0 263 526 A1 | 4/1988 |
| EP | 0 154 445 B1 | 5/1989 |
| EP | 0 702 014 A1 | 3/1996 |
| JP | 2008-531542 A | 8/2008 |
| JP | 2009-525322 A | 7/2009 |
| JP | 2009529030 A | 8/2009 |
| WO | WO 88/04659 A2 | 6/1988 |
| WO | WO 90/02746 A1 | 3/1990 |
| WO | WO 91/16324 A1 | 10/1991 |
| WO | WO 94/04535 A1 | 3/1994 |
| WO | WO 94/24304 A1 | 10/1994 |
| WO | WO 95/31971 A1 | 11/1995 |
| WO | WO 96/23497 A1 | 8/1996 |

(Continued)

OTHER PUBLICATIONS

International Search Report for International Applciation No. PCT/NL2007/050384 dated Apr. 3, 2008.
Tietze et al., "Synthesis and Biological Evaluation of Novel Analogues and Prodrugs of the Cytotoxic Antibiotic CC-1065 for Selective Cancer Therapy," *Eur. J. Org. Chem.*, 1634-1645 (2002).
Braga, D., et al., "Crystal Polymorphism and Multiple Crystal Forms," *Structural Bond* 132:25-50, Springer-Verlag Berlin Heidelberg, Germany (Feb. 2009).

(Continued)

*Primary Examiner* — Timothy Thomas
*Assistant Examiner* — George W Kosturko
(74) *Attorney, Agent, or Firm* — Sterne, Kessler, Goldstein & Fox P.L.L.C.

(57) ABSTRACT

This invention relates to novel agents that are analogs of the DNA-alkylating agent CC-1065 and to their conjugates. Furthermore this invention concerns intermediates for the preparation of said agents and their conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an illness that is characterized by undesired (cell) proliferation. As an example, the agents and the conjugates of this invention may be used to treat a tumor.

5 Claims, 4 Drawing Sheets

(56) References Cited

FOREIGN PATENT DOCUMENTS

| | | |
|---|---|---|
| WO | WO 97/07097 A1 | 2/1997 |
| WO | WO 97/12862 A1 | 4/1997 |
| WO | WO 97/32850 A1 | 9/1997 |
| WO | WO 97/44000 A2 | 11/1997 |
| WO | WO 97/45411 A1 | 12/1997 |
| WO | WO 98/11101 A2 | 3/1998 |
| WO | WO 98/25898 A1 | 6/1998 |
| WO | WO98-25900 | 6/1998 |
| WO | WO 98/52925 A1 | 11/1998 |
| WO | WO 99/19298 A1 | 4/1999 |
| WO | WO 99/31120 A1 | 6/1999 |
| WO | WO 01/83482 A1 | 11/2001 |
| WO | WO2001-083448 | 11/2001 |
| WO | WO 02/30894 A2 | 4/2002 |
| WO | WO 02/059122 A1 | 8/2002 |
| WO | WO 02/067930 A1 | 9/2002 |
| WO | WO 02/067937 A1 | 9/2002 |
| WO | WO 02/068412 A1 | 9/2002 |
| WO | WO 02/083180 A1 | 10/2002 |
| WO | WO 02/096910 A1 | 12/2002 |
| WO | WO 03/022806 A2 | 3/2003 |
| WO | WO 03/086318 A2 | 10/2003 |
| WO | WO 03/097635 A1 | 11/2003 |
| WO | WO 2004/043493 A1 | 5/2004 |
| WO | WO 2004/069159 A2 | 8/2004 |
| WO | WO 2004/069201 A2 | 8/2004 |
| WO | WO 2004/101767 A2 | 11/2004 |
| WO | WO 2005/032594 A2 | 4/2005 |
| WO | WO 2005/079398 A2 | 9/2005 |
| WO | WO 2005/103040 A1 | 11/2005 |
| WO | WO 2005/105154 A1 | 11/2005 |
| WO | WO2005-112919 | 12/2005 |
| WO | WO 2005112919 A2 * | 12/2005 ........... A61K 31/403 |
| WO | WO 2006/002895 A2 | 1/2006 |
| WO | WO 2006/012527 A1 | 2/2006 |
| WO | WO 2006/034488 A2 | 3/2006 |
| WO | WO 2006/037052 A2 | 4/2006 |
| WO | WO 2006/043839 A1 | 4/2006 |
| WO | WO 2006/090261 A1 | 8/2006 |
| WO | WO 2006/110476 A2 | 10/2006 |
| WO | WO 2007/038658 A2 | 4/2007 |
| WO | WO 2007/051081 A1 | 5/2007 |
| WO | WO 2007/059404 A2 | 5/2007 |
| WO | WO2007-089149 | 8/2007 |
| WO | WO 2008/063378 A2 | 5/2008 |
| WO | WO 2008/074004 A2 | 6/2008 |
| WO | WO 2008/103693 A2 | 8/2008 |
| WO | WO 2009/064908 A1 | 5/2009 |
| WO | WO 2010/027280 A1 | 3/2010 |
| WO | WO 2010/033733 A1 | 3/2010 |
| WO | WO 2010/062171 A2 | 6/2010 |
| WO | WO 2011/133039 A2 | 10/2011 |
| WO | WO 2013/049410 A1 | 4/2013 |
| WO | WO 2013/093809 A1 | 6/2013 |
| WO | WO 2015/104359 A2 | 7/2015 |
| WO | WO 2015/185142 A1 | 12/2015 |
| WO | WO 2016/046173 A1 | 3/2016 |

OTHER PUBLICATIONS

Boger, D.L. and Johnson, D.S., "CC-1065 and the Duocarmycins: Unraveling the Keys to a New Class of Naturally Derived DNA Alkylating Agents," Proceedings of the National Academy of Sciences, USA 92:3642-2649, National Academy of Sciences, United States (1995).

Boyd, M.R., "Status of the NCI preclinical antitumor drug discovery screen," in Cancer: Principles and Practice of Oncology, vol. 3, No. 10, DeVita, V.T., Jr., et al., eds., pp. 1-12, Lippincott Williams & Wilkins, United States (1989).

El-Sahwi, K.S., et al., Author Manuscript of "Development of targeted therapy in uterine serous carcinoma, a biologically aggressive variant of endometrial cancer," Expert Review of Anticancer Therapy 12(1):41-49, Expert Reviews Ltd., England, 15 pages (2012).

Popowycz, F., et al., "Synthesis and reactivity of 4-, 5- and 6-azaindoles," Tetrahedron 63(36):8689-8707, Elsevier Ltd., England (2007).

Tietze, L.F., et al., "Determination of the Biological Activity and Structure Activity Relationships of Drugs Based on the Highly Cytotoxic Duocarmycins and CC-1065," Toxins 1:134-150, MDPI AG, Switzerland (Dec. 2009).

Vippagunta, S.R., et al., "Crystalline Solids," Advanced Drug Delivery Reviews 48:3-26, Elsevier Science B.V., Netherlands (2001).

Amishiro. N., et al., "New Water-Soluble Duocarmycin Derivatives: Synthesis and Antitumor Activity of A-Ring Pyrrole Compounds Bearing β-Heteroarylacryloyl Groups," Journal of Medicinal Chemistry 42(4):669-676, American Chemical Society, United States (1999).

Amishiro, N., et al., "Synthesis and Antitumor Activity of Duocarmycin Derivatives: A-Ring Pyrrole Compounds Bearing β-(5', 6', 7'-Trimethoxy-2'-indolyl)acryloyl Group," Bioorganic & Medicinal Chemistry 8(7):1637-1643, Elsevier Science Ltd., England (2000).

Aristoff, P.A. & Johnson, P.D., "Synthesis of CBI-PDE-I-Dimer, the Benzannelated Analog of CC-1065," The Journal of Organic Chemistry 57(23):6234-6239, American Chemical Society, United States (1992).

Atwell, G.J., et al., "5-Amino-1-(chloromethyl)-1,2-clihydro-3H-benz[e]indoles: Relationships between Structure and Cytotoxicity for Analogues Bearing Different DNA Minor Groove Binding Subunits," Journal of Medicinal Chemistry 42(17):3400-3411, American Chemical Society, United States (1999).

Bagshawe, K.D., et al., "Antibody-Directed Enzyme Prodrug Therapy: A Review," Drug Development Research 34:220-230, Wiley-Liss, Inc., United States (1995).

Bagshawe, K.D., et al., "A Cytotoxic Agent Can be Generated Selectively at Cancer Sites," British Journal of Cancer 58:700-703, The Macmillan Press Ltd., England (1988).

Bando, T. and Sugiyama, H., "Synthesis and Biological Properties of Sequence-Specific DNA-Alkylating Pyrrole-Imidazole Polyamides," Accounts of Chemical Research 39(12):935-944, American Chemical Society, United States (2006).

Boger, D.L. et al., "Examination of the Role of the Duocarmycin SA Methoxy Substituents: Identification of the Minimum, Fully Potent DNA Binding Subunit," Bioorganic & Medicinal Chemistry Letters 6(18):2207-2210, Elsevier Science Ltd., England (1996).

Boger, D.L., et al., "Synthesis and Properties of Substituted CBI Analogs of CC-1065 and the Duocarmycins Incorporating the 7-Methoxy-1,2,9,9a-tetrahydrocyclopropa[c]benz[e]indol-4-one (MCBI) Alkylation Subunit: Magnitude of Electronic Effects on the Functional Reactivity," J. Org. Chem. 61(5):1710-1729, American Chemical Society, United States (1996).

Boger, D.L. et al., "CC-1065 and the Duocarmycins: Synthetic Studies," Chemical Reviews 97(3):787-828, American Chemical Society, United States (1997).

Boder, D.L. et al., "Substituent Effects within the DNA Binding Subunit of CBI Analogues of the Duocarmycins and CC-1065," Bioorganic & Medicinal Chemistry Letters 11(15):2021-2024, Elsevier'Ltd., England (2001).

Boger, D.L., et al., "Synthesis and Evaluation of a Series of C3-Substituted CBI Analogues of CC-1065 and the Duocarmycins," The Journal of Organic Chemistry 66(15):5163-5173, American Chemical Society, United States (2001).

Carter, P., et al., "Identification and Validation of Cell Surface Antigens for Antibody Targeting in Oncology," Endocrine-Related Cancer 11:659-687, Society for Endocrinology, England (2004).

Daniell, K. et al., "Design, Synthesis, and Biological Evaluation of Achiral Analogs of Duocarmycin SA," Bioorganic & Medicinal Chemistry Letters 15(1):177-180, Elsevier Ltd., England (2005).

Duncan, R., "The Dawning Era of Polymer Therapeutics," Nature Reviews Drug Discovery 2:347-360, Nature Publisher Group, England (2003).

Elvira, C., et al., "Covalent Polymer-Drug Conjugates," Molecules 10:114-125, MDPI AG, Switzerland (2005).

(56) References Cited

OTHER PUBLICATIONS

Frankel, A.E., et al., "Cell Surface Receptor-Targeted Therapy of Acute Myeloid Leukemia: A Review," *Cancer Biotherapy & Radiopharmaceuticals* 15(5):459-476, Mary Ann Liebert, Inc., United States (2000).

Greenwald, R.B., et al., "Effective Drug Delivery by PEGylated Drug Conjugates," *Advanced Drug Delivery Reviews* 55:217-250, Elsevier Science Publishers, B.V., Netherlands (2003).

Greenwald, R.B., et al., "A new aliphatic amino prodrug system for the delivery of small molecules and proteins utilizing novel PEG derivatives," *J Med Chem* 47(3):726-734, American Chemical Society, United States (2004).

Huber, B.E., et al., "Retroviral-Mediated Gene Therapy for the Treatment of Hepatocellular Carcinoma: An Innovative Approach for Cancer Therapy," *Proceedings of the National Academy of Sciences, USA* 88:8039-8043, National Academy of Sciences, United States (1991).

Jeffrey, S.C., et al., "Design, Synthesis, and in Vitro Evaluation of Dipeptide-Based Antibody Minor Groove Binder Conjugates," *Journal of Medicinal Chemistry* 48(5):1344-1358, American Chemical Society, United States (2005).

Kingsbury, W.D., et al.. "A Novel Peptide Delivery System Involving Peptidase Activated Prodrugs as Antimicrobial Agents. Synthesis and Biological Activity of Peptidyl Derivatives of 5-Fluorouracil," *Journal of Medicinal Chemistry* 27:1447-1451, American Chemical Society, United States (1984).

McGovren, J.P., et al., "Preliminary Toxicity Studies with the DNA-Binding Antibiotic, CC-1065," *The Journal of Antibiotics* 37(1):63-70, Antibiotics Research Association, Japan (1984).

Melton, R., et al., "The Use of Prodrugs in Targeted Anticancer Therapies," *S.T.P. Pharma Sciences* 9(1):13-33, Éditions de Santé, France (1999).

Milbank, J.B. et al., "Synthesis of 1-Substituted 3-(Chloromethyl)-6-aminoindoline (6-Amino-seco-CI) DNA Minor Groove Alkylating Agents and Structure-Activity Relationships for Their Cytotoxicity," *Journal Medicinal Chemistry* 42(4):649-658, American Chemical Society, United States (1999).

Murray, J.L., "Monoclonal Antibody Treatment of Solid Tumors: A Coming of Age," *Seminars in Oncology* 27(6 Suppl 11):64-70, W.B. Saunders Company, United States (2000).

Parrish, J.P., et al., "Establishment of Substituent Effects in the DNA Binding Subunit of CBI Analogues of the Duocarmycins and CC-1065," *Bioorganic & Medicinal Chemistry* 11(17):3815-3838, Elsevier Ltd., England (2003).

Parrish, J.P., et al., "Synthesis and Evaluation of N-aryl and N-alkenyl CBI Derivatives," *Bioorganic & Medicinal Chemistry* 12(22):5845-5856, Elsevier Ltd., England (2004).

Purnell, B. et al., "DNA Interstrand Crosslinking Agents: Synthesis, DNA Interactions, and Cytotoxicity of Dimeric Achiral Seco-Amino-CBI and Conjugates of Achiral Seco-Amino-CBI with Pyrrolobenzodiazepine (PBD)," *Bioorgcznic & Medicinal Chemistry Letters* 16(21):5677-5681, Elsevier Science Ltd., England (2006).

Ringsdorf, H., "Structure and Properties of Pharmacologically Active Polymers," *Journal of Polymer Science: Polymer Symposia* 51:135-153, John Wiley & Sons, United States (1975).

Schuster, H.J., et al., "Synthesis of the First Spacer Containing Prodrug of a Duocarmycin Analogue and Determination of Its Biological Activity," *Organic & Biomolecular Chemistry* 8(8):1833-1842, Royal Society of Chemistry, England (2010).

Suzawa, T. et al., "Synthesis of a Novel Duocarmycin Derivative DU-257 and Its Application to Immunoconjugate Using Poly(ethylene glycol)-dipeptidyl Linker Capable of Tumor Specific Activation," *Bioorganic & Medicinal Chemistry* 8(8):2175-2184, Elsevier Science Ltd., England (2000).

Ticiienor, M.S. et al., "Asymmetric Total Synthesis of (+)- and ent-(-)-Yatakemycin and Duocarmycin SA: Evaluation of Yatakemycin Key Partial Structures and its Unnatural Enantiomer," *Journal of the American Chemical Society* 128(49):15683-15696, American Chemical Society, United States (2006).

Tietze, L.F., et al., "Highly Selective Glycosylated Prodrugs of Cytostatic CC-1065 Analogues for Antibody-Directed Enzyme Tumor Therapy," *ChemBioChem* 2(10):758-765, Wiley-VCH—Verlag GmbH, Germany (2001).

Tietze, L.F., et al., "A Strategy for Tumor-Selective Chemotherapy by Enzymatic Liberation of seco-duocarmycin SA-Derivatives from Nontoxic Prodrugs," *Bioorganic & Medicinal Chemistry* 9:1929-1939, Elsevier Science Ltd., England (2001).

Tietze, L.F., et al., "Antitumor Agents: Development of Highly Potent Glycosidic Duocarmycin Analogues for Selective Cancer Therapy," *Angewandte Chemie International Edition* 45:6574-6577, Wiley-VCH Verlag GmbH & Co. KGaA, Germany (2006).

Tietze, L.F., et al., "Selective Treatment of Cancer: Synthesis, Biological Evaluation and Structural Elucidation of Novel Analogues of the Antibiotic CC-1065 and the Duocarmycins," *Chemistry—A European Journal* 13(16):4396-4409, Wiley-VCH Verlag GmbH, Germany (Apr. 2007).

Tietze, L.F., et al., "Asymmetric Synthesis and Biological Evaluation of Glycosidic Prodrugs for a Selective Cancer Therapy," *ChemMedChem* 3(12):1946-1955, Wiley-VCH Verlag GmbH & Co. KGaA, Germany (Dec. 2008).

Toki, B.E., et al., "Protease-Mediated Fragmentation of p-Amidobenzyl Ethers: A New Strategy for the Activation of Anticancer Prodrugs," *Journal of Organic Chemistry* 67:1866-1872, American Chemical Society, United States (2002).

Wang, Y., et al., "Design, Synthesis, Cytotoxic Properties and Preliminary DNA Sequencing Evaluation of CPI-N-methylpyrrole Hybrids. Enhancing Effect of a trans Double Bond Linker and Role of the Terminal Amide Functionality on Cytotoxic Potency," *Anti-Cancer Drug Design* 11(1):15-34, Oxford University Press, United States (1996).

Wang, Y. et al., "Synthesis and Preliminary Biological Evaluations of CC-1065 Analogues: Effects of Different Linkers and Terminal Amides on Biological Activity," *Journal of Medicinal Chemistry* 43(8):1541-1549, American Chemical Society, United States (2000).

Wang, Y., et al., "CC-1065 Analogues Bearing Different DNA-Binding Subunits: Synthesis, Antitumor Activity, and Preliminary Toxicity Study," *Journal of Medicinal Chemistry* 46(4):634-637, American Chemical Society, United States (2003).

Wang, Y. et al., "Synthesis and Antitumor Activity of CBI-bearing Ester and Carbamate Prodrugs of CC-1065 Analogue," *Bioorganic and Medicinal Chemistry* 14(23):7854-7861, Elsevier Ltd., England (2006).

Wrasidlo, W., et al., "Induction of Endonucleolytic DNA Fragmentation and Apoptosis by the Duocarmycins," *Bioorganic & Medicinal Chemistry Letters* 4(4):631-636, Elsevier Science Ltd., England (1994).

Non-Final Office Action dated Oct. 24, 2012 for U.S. Appl. No. 12/671,609, Beusker, P.H., et al., having a § 371(c) date of Oct. 26, 2010.

Final Office Action dated May 8, 2013 for U.S. Appl. No. 12/671,609, Beusker, P.H., et al., having a § 371(c) date of Oct. 26, 2010.

Notice of Allowance dated Nov. 6, 2013 for U.S. Appl. No. 12/671,609, Beusker, P.H., et al., having a § 371(c) date of Oct. 26, 2010.

Non-Final Office Action in U.S. Appl. No. 13/126,920, inventors Beusker, P. et al., filed Apr. 29, 2011, 20 pages, U.S. Patent Office, United States, dated Apr. 22, 2013.

Final Office Action in U.S. Appl. No. 13/126,920, inventors Beusker, P. et al., filed Apr. 29, 2011, 22 pages, U.S. Patent Office, United States, dated Jan. 7, 2014.

Notice of Allowance in U.S. Appl. No. 13/126,920, inventors Beusker, P. et al., filed Apr. 29, 2011, 5 pages, U.S. Patent Office, United States, dated Jul. 7, 2014.

Non-Final Office Action in U.S. Appl. No. 13/642,847, inventors Beusker, P. et al., having a § 371(c) date of Nov. 27, 2012, 23 pages, U.S. Patent Office, United States, dated Mar. 20, 2015.

Final Office Action in U.S. Appl. No. 13/642,847, inventors Beusker, P. et al., having a § 371(c) date of Nov. 27, 2012, 18 pages, U.S. Patent Office, United States, dated Dec. 2, 2015.

(56) References Cited

OTHER PUBLICATIONS

International Preliminary Report on Patentability and Written Opinion for International Application No. PCT/NL2007/050384, The International Bureau of WIPO, Geneva, Switzerland, dated Feb. 2, 2010, 8 pages.
Keepers, Y.P., et al., "Comparison of the sulforhodamine B protein and tetrazolium (MTT) assays for in vitro chemosensitivity testing," *Eur J Cancer.* 27(7):897-900, Pergamon Press, PLC., England (1991).
Non-Final Office Action in U.S. Appl. No. 14/859,201, inventors Dokter, W., et al., filed Sep. 18, 2015, 12 pages, U.S. Patent Office, United States, dated Mar. 16, 2016.
Non-Final Office Action in U.S. Appl. No. 14/859,221, inventors Santin, A., et al., filed Sep. 18, 2015, 12 pages, U.S. Patent Office, United States, dated Mar. 9, 2016.
Attard, G., et al., "A phase Ib study of pertuzumab, a recombinant humanised antibody to HER2, and docetaxel in patients with advanced solid tumours," *British Journal of Cancer* 97(10):1338-1343, Cancer Research UK, England (Nov. 2007).
Haymarket Media, Inc., "Endometrial Carcinoma Chemotherapy and Other Treatment Regimens," 1 page (Mar. 2012).
Mellstedt, H., "Clinical considerations for biosimilar antibodies," *EJC Supplements* 11(3):1-11, Elsevier Ltd., England (2013).
Roitt, I.M., "Antigens," in *Immunology*, 3rd Edition, Roitt, I.M., et al., eds., p. 1.7, Mosby-Year Book Europe Limited, England (1993).
Non-Final Office Action dated Nov. 22, 2016 in U.S. Appl. No. 15/216,366, inventors Santin, A.D. et al., filed Jul. 21, 2016.
Co-pending, U.S. Appl. No. 15/216,407, inventors Dokter, W. et al., filed Jul. 21, 2016 (Not Published).
Co-pending, U.S. Appl. No. 15/216,366, inventors Santin, A.D. et al., filed Jul. 21, 2016 (Not Published).
Kovtun, Y.V. and Goldmacher, V.S., "Cell killing by antibody-drug conjugates," *Cancer Letters* 255(2):232-240, Elsevier Ireland Ltd., Ireland (Oct. 2007).
Müller, U., "Polymorphism," in *Inorganic Structural Chemistry*, pp. 14-15, John Wiley & Sons Ltd, England (1993).
Non-Final Office Action dated Jun. 2, 2016 in U.S. Appl. No. 13/642,847, inventors Beusker, P.H. et al., § 371(c) date Nov. 27, 2012.
Non-Final Office Action dated Jun. 2, 2016 in U.S. Appl. No. 14/526,462, inventors Beusker, P.H. et al., filed Oct. 28, 2014.
Notice of Allowance dated Jun. 29, 2016 in U.S. Appl. No. 14/859,221, inventors Santin, A.D. et al., filed Sep. 18, 2015.
Notice of Allowance dated Jun. 30, 2016 in U.S. Appl. No. 14/859,201, inventors Dokter, W. et al., filed Sep. 18, 2015.
Non-Final Office Action dated Oct. 21, 2016 in U.S. Appl. No. 15/216,407, inventors Dokter, W. et al., filed Jul. 21, 2016.
Cumnock, K., et al., "Trisulfide Modification Impacts the Reduction Step in Antibody-Drug Conjugation Process," *Bioconjugate Chemistry* 24(7):1154-1160, American Chemical Society, United States (2013).
Dokter, W.H.A., et al., "Abstract 2652: In vitro and in vivo antitumor activity of SYD985, a novel HER2-targeting ADC: a comparison with T-DMI," *Cancer Research* 74(Suppl 19):Abstract 2652, Proceedings of the 105th Annual Meeting of the American Association for Cancer Research, Apr. 5-9, 2014, San Diego, CA (Oct. 1, 2014).
Foulkes, W.D., et al., "Triple-Negative Breast Cancer," *The New England Journal of Medicine* 363:1938-1948, Massachusetts Medical Society, United States (Nov. 2010).
Hamblett, K.J., et al., "Effects of Drug Loading on the Antitumor Activity of a Monoclonal Antibody Drug Conjugate," *Clinical Cancer Research* 10(20):7063-7070, American Association for Cancer, United States (2004).

Dokter, W., et al., "Preclinical Profile of the HER2-Targeting ADC SYD983/SYD985: Introduction of a New Duocarmycin-Based Linker-Drug Platform" (Supplemental Data Included) *Molecular Cancer Therapeutics* 13(11):2618-2629, American Association of Cancer Research, United States (Sep. 2014).
McDonagh, C.F., et al., "Engineered antibody-drug conjugates with defined sites and stoichiometries of drug attachment," *Protein Engineering, Design & Selection* 19(7):299-307, Oxford University Press, England (2006).
Shen, B-Q., et al., "Conjugation site modulates the in vivo stability and therapeutic activity of antibody-drug conjugates," *Nature Biotechnology* 30(2):184-189, Nature Publishing Group, United States (2012).
Ouyang, J., "Drug-to-antibody ratio (DAR) and drug load distribution by hydrophobic interaction chromatography and reversed phase high-performance liquid chromatography," *Methods in Molecular Biology* 1045:275-283, Springer Science+Business Media, LLC, England (2013).
Sun, M.M.C., et al., "Reduction-Alkylation Strategies for the Modification of Specific Monoclonal Antibody Disulfides," *Bioconjugate Chem.* 16(5):1282-1290, American Chemical Society, United States (2005).
Van Der Lee, M., et al., "Poster 2652:The HER2-targeting ADC SYD985 shows superior antitumor activity compared to T-DMI in preclinical studies with an activity profile that includes low-HER2 expressing breast cancers," AACR Annual Meeting 2014, Apr. 5-9, 2014, San Diego, CA.
Van Der Lee, M.M., et al., "The Preclinical Profile of the Duocarmycin-Based HER2-Targeting ADC SYD985 Predicts for Clinical Benefit in Low HER2-Expressing Breast Cancers," *Mol Cancer Ther.* 14(3):692-703, American Association for Cancer Research, United States (published online Jan. 14, 2015).
Verheijden, G., et al., "Poster 850294: Preclinical Data of SYD985 Support the Clinical Investigation of This Novel Anti-HER2 Antibody-Drug Conjugate in Breast Cancer Patients with Low Levels of HER2 Expression," 2014 San Antonio Breast Cancer Symposium, (Dec. 2014).
Notice of Allowance dated Jan. 11, 2017 in U.S. Appl. No. 13/642,847, inventors Beusker, P.H. et al., § 371(c) date Nov. 27, 2012.
Final Office Action dated Jan. 13, 2017 in U.S. Appl. No. 14/526,462, inventors Beusker, P.H. et al., filed Oct. 28, 2014.
Junutula, J.R., et al., "Site-specific conjugation of a cytotoxic drug to an antibody improves the therapeutic index," *Nature Biotechnology* 26(8):925-932, Nature Publishing Group, England (2008).
Tietze, L.F., et al., "Synthesis of Fluorescence-Labelled Glycosidic Prodrugs Based on the Cytotoxic Antibiotic Duocarmycin," *Eur. J. Org. Chem.* 2010(36):6909-6921, Wiley-VCH Verlag GmbH & Co., Germany (Dec. 2010).
Tietze, L.F., et al., "Enantio- and Diastereoselective Synthesis of Duocarmycine-Based Prodrugs for a Selective Treatment of Cancer by Epoxide Opening," *Chemistry—A European Journal* 14(3):895-901, Wiley-VCH Verlag GmbH & Co., Germany (2008).
Tietze, L.F., et al., "Atropisomerism of Aromatic Carbamates," *Chemistry—A European Journal* 16(42):12678-12682, Wiley-VCH Verlag GmbH & Co., Germany (Nov. 2010).
Sigma-Aldrich Co. LLC, "Product Information," Catalog No. B3773, sigma-aldrich.com, accessed at http://www.sigmaaldrich.com/content/dam/sigma-aldrich/docs/Sigma/Datasheet/b3773dat.pdf, accessed on Apr. 20, 2017, 1 page.
Advisory Action dated May 15, 2017 in U.S. Appl. No. 14/526,462, inventors Beusker, P.H. et al., filed Oct. 28, 2014.
Notice of Allowance dated Jun. 29, 2017 in U.S. Appl. No. 14/526,462, inventors Beusker, P.H. et al., filed Oct. 28, 2014.

* cited by examiner

SUBSTITUTED CC-1065 ANALOGS AND THEIR CONJUGATES

This application is a divisional of U.S. application Ser. No. 12/671,609, filed Oct. 26, 2010, which was the national stage of PCT application serial number PCT/NL2007/050384, filed Aug. 1, 2007; the entire contents of these prior applications being incorporated herein by reference.

FIELD OF THE INVENTION

This invention relates to novel agents that are analogs of the DNA-alkylating agent CC-1065 and to their conjugates. Furthermore this invention concerns intermediates for the preparation of said agents and their conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an illness that is characterized by undesired (cell) proliferation. As an example, the agents and the conjugates of this invention may be used to treat a tumor.

BACKGROUND OF THE INVENTION

The duocarmycins, first isolated from a culture broth of *Streptomyces* species, are members of a family of antitumor antibiotics that also includes CC-1065. These extremely potent agents allegedly derive their biological activity from an ability to sequence-selectively alkylate DNA at the N3 of adenine in the minor groove, which initiates a cascade of events that terminates in an apoptotic cell death mechanism.[1]

Although CC-1065 has shown very potent cytotoxicity, it could not be used in the clinic because of serious delayed hepatotoxicity.[2] This observation led to the development of synthetic analogs of CC-1065 (see for CC-1065 derivatives for example Aristoff et al., *J. Org. Chem.* 1992, 57, 6234; Boger et al., *Bioorg. Med. Chem. Lett.* 1996, 6, 2207; Boger et al., *Chem. Rev.* 1997, 97, 787; Milbank et al., *J. Med. Chem.* 1999, 42, 649; Atwell et al., *J. Med. Chem.* 1999, 42, 3400; Wang et al., *J. Med. Chem.* 2000, 43, 1541; Boger et al., *Bioorg. Med. Chem. Lett* 2001, 11, 2021; Parrish et al., *Bioorg. Med. Chem.* 2003, 11, 3815; Daniell et al., *Bioorg. Med. Chem. Lett.* 2005, 15, 177; Tichenor et al., *J. Am. Chem. Soc.* 2006, 128, 15683; Purnell et al., *Bioorg. Med. Chem.* 2006, 16, 5677; Bando and Sugiyama, *Acc. Chem. Res.* 2006, 39, 935; EP0154445; WO 88/04659; WO 90/02746; WO 97/12862; WO 97/32850; WO 97/45411; WO 98/52925; WO 99/19298; WO 01/83482; WO 02/067937; WO 02/067930; WO 02/068412; WO 03/022806; WO 2004/101767; WO 2006/043839; and WO 2007/051081), which generally showed to have similar cytotoxicity, but reduced hepatotoxicity. Still, however, these derivatives lack sufficient selectivity for tumor cells as the selectivity of these agents—and cytotoxic agents in general—is for a considerable part based on the difference in the rate of proliferation of tumor cells and normal cells, and therefore they also affect healthy cells that show a relatively high proliferation rate. This typically leads to severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can be considered one of the primary goals.

One promising approach to obtain selectivity for tumor cells or tumor tissue is to exploit the existence of tumor-associated antigens, receptors, and other receptive moieties, which can serve as a target. Such a target may be upregulated or to some degree be specifically present in tumor tissue or in closely associated tissue, such as neovascular tissue, with respect to other tissues in order to achieve efficient targeting. Many targets have been identified and validated and several methods to identify and validate targets have been developed.[3] By coupling a ligand, e.g. an antibody or antibody fragment, for such a tumor-associated antigen, receptor, or other receptive moiety to a therapeutic agent, this agent can be selectively targeted to tumor tissue.

Another promising approach to obtain selectivity for tumor cells or tumor tissue is to exploit the existence of tumor-associated enzymes. An enzyme that is mainly localized at the tumor site can convert a pharmacologically inactive prodrug, which consists of an enzyme substrate directly or indirectly linked to the toxic drug, to the corresponding drug in the vicinity of or inside the tumor.

Via this concept a high concentration of toxic anticancer agent can be selectively generated at the tumor site. All tumor cells may be killed if the dose is sufficiently high, which may decrease development of drug-resistant tumor cells.

Enzymes can also be transported to the vicinity of or inside target cells or target tissue via for example antibody-directed enzyme prodrug therapy (ADEPT)[4], polymer-directed enzyme prodrug therapy (PDEPT) or macromolecular-directed enzyme prodrug therapy (MDEPT)[5], virus-directed enzyme prodrug therapy (VDEPT)[6], or gene-directed enzyme prodrug therapy (GDEPT)[7]. With ADEPT, for example, a non-toxic prodrug is selectively converted into a cytotoxic compound at the surface of target cells by an antibody-enzyme conjugate that has been pretargeted to the surface of those cells.

Yet another promising approach to obtain selectivity for tumor cells or tumor tissue is to exploit the enhanced permeability and retention (EPRB) effect. Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.[8] By coupling a therapeutic agent directly or indirectly to a macromolecule, said agent can be selectively targeted to tumor tissue.

Besides efficient targeting, other important criteria for the successful application of targeted conjugates of cytotoxic agents in tumor therapy are that the one or more agents are released efficiently from the conjugate at the tumor site and that the conjugate is non-cytotoxic or only very weakly cytotoxic, whereas the cytotoxic agent itself exhibits highly potent cytotoxicity. Ideally, this leads to the generation of cytotoxic molecules only at the tumor site, which results in a greatly increased therapeutic index with respect to the untargeted cytotoxic agent. Another important criterion for a successful targeted conjugate is that the conjugate must have suitable pharmacological properties, such as sufficient stability in the circulation, low aggregation tendency, and good water solubility.

Several conjugates of CC-1065 and derivatives have been described (see for conjugates of CC-1065 derivatives for example Suzawa et al., *Bioorg. Med. Chem.* 2000, 8, 2175; Jeffrey et al., *J. Med. Chem.* 2005, 48, 1344; Wang et al., *Bioorg. Med Chem.* 2006, 14, 7854; Tietze et al., *Chem. Eur. J.* 2007, 13, 4396; WO 91/16324; WO 94/04535; WO 95/31971; U.S. Pat. No. 5,475,092; U.S. Pat. No. 5,585,499;

U.S. Pat. No. 5,646,298; WO 97/07097; WO 97/44000; U.S. Pat. No. 5,739,350; WO 98/11101; WO 98/25898; U.S. Pat. No. 5,843,937; U.S. Pat. No. 5,846,545; WO 02/059122; WO 02/30894; WO 03/086318; WO 2005/103040; WO 2005/112919; WO 2006/002895; WO 2006/110476; WO 2007/038658; and WO 2007/059404). In these conjugates, one or more of the favorable properties discussed above are non-optimal. As an illustrative example, glycoside conjugates of seco CC-1065 analogs have been described that can be activated at the lesion site via an ADEPT approach.[9] The difference in cytotoxicity between the conjugates and the corresponding drugs, expressed as the cytotoxicity quotient, $IC_{50, conjugate}/IC_{50, parent\ drug}$, was however relatively low, and the seco CC-1065 analogs themselves did not show extremely potent cytotoxicity. Improvements to the cytotoxicity quotient were made through the development of glycoside conjugates of seco CC-1065 derivatives with a secondary leaving group.[10] Although these conjugates demonstrated a high cytotoxicity quotient, their pharmacological properties were non-optimal. For instance, they generally showed poor water solubility, which is a consequence of the inherent lipophilic nature of the CC-1065 class of compounds.

Accordingly, there is still a clear need in the art for conjugates of CC-1065 derivatives that show high cytotoxicity quotients, contain CC-1065 derivatives that have potent cytotoxicity and favorable pharmacological properties, and release the CC-1065 derivatives efficiently.

SUMMARY OF THE INVENTION

The present invention fulfils the above-mentioned need with a compound of formula (I) or (II):

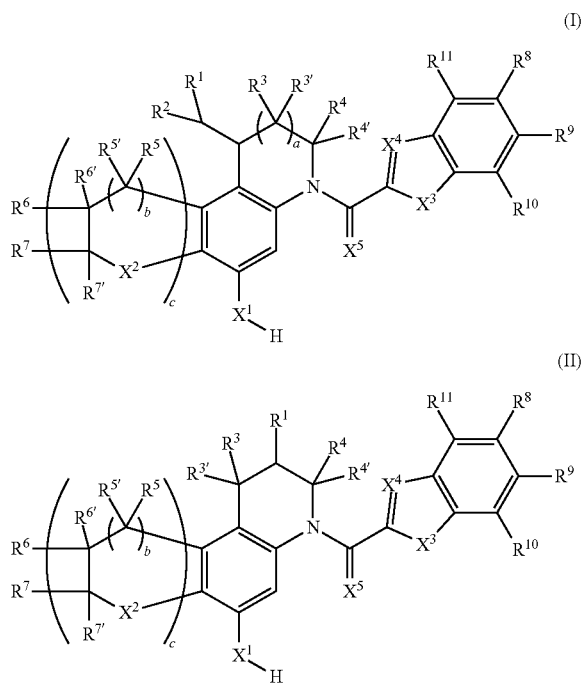

or a pharmaceutically acceptable salt, hydrate, or solvate thereof, wherein $R^1$ is a leaving group;

$R^2$ is selected from H, $N_3$, $NO_2$, NO, $CF_3$, CN, $C(O)NH_2$, $C(O)H$, $C(O)OH$, halogen, $R^b$, $SR^b$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2$ $OR^a$, $OR^b$, $N(R^b)R^c$, $^+N(R^b)(R^c)R^d$, $P(O)(OR^a)(OR^{a'})$, $OP(O)(OR^a)(OR^{a'})$, $SiR^aR^{a'}R^{a''}$, $C(O)R^a$, $C(O)OR^a$, $C(O)N(R^a)R^{a'}$, $OC(O)R^a$, $OC(O)OR^a$, $OC(O)N(R^a)R^{a'}$, $N(R^a)C(O)R^{a'}$, $N(R^a)C(O)OR^{a'}$, and $N(R^a)C(O)N(R^{a'})R^{a''}$, wherein $R^a$, $R^{a'}$, and $R^{a''}$ are independently selected from H and optionally substituted $C_{1-3}$ alkyl or $C_{1-3}$ heteroalkyl, and $R^b$, $R^c$, and $R^d$ are independently selected from optionally substituted $C_{1-3}$ alkyl and $C_{1-3}$ heteroalkyl;

$R^3$, $R^{3'}$, $R^4$, and $R^{4'}$ are independently selected from H and optionally substituted $C_{1-3}$ alkyl, wherein two or more of $R^2$, $R^3$, $R^{3'}$, $R^4$, and $R^{4'}$ are optionally joined by one or more bonds to form one or more optionally substituted carbocycles and/or heterocycles, and/or $R^3+R^{3'}$ and/or $R^4+R^{4'}$ are independently =O, =S, =$NOR^{18}$, or =$NR^{18}$, $R^{18}$ being selected from H and optionally substituted $C_{1-3}$ alkyl;

$X^2$ is selected from O, $C(R^{14})(R^{4'})$, and $NR^{14'}$, wherein $R^{14}$ is selected from H and optionally substituted $C_{1-8}$ alkyl or $C_{1-8}$ acyl and wherein $R^{14'}$ is absent or is selected from H and optionally substituted $C_{1-8}$ alkyl or $C_{1-8}$ acyl;

$R^5$ and $R^{5'}$ are independently selected from H, OH, SH, $NH_2$, $N_3$, $NO_2$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles, and $R^6$, $R^{6'}$, $R^7$, and $R^{7'}$ are independently selected from H, OH, SH, $NH_2$, $N_3$, $NO_2$, NO, $CF_3$, CN, $C(O)NH_2$, $C(O)H$, $C(O)OH$, halogen, $R^{e'}$, $SR^{e'}$, $S(O)R^{e'}$, $S(O)_2R^{e'}$, $S(O)OR^{e'}$, $S(O)_2OR^{e'}$, $OS(O)R^{e'}$, $OS(O)_2R^{e'}$, $OS(O)OR^{e'}$, $OS(O)_2OR^{e'}$, $OR^{e'}$, $NHR^{e'}$, $N(R^{e'})R^{f'}$, $^+N(R^{e'})(R^{f'})R^{g'}$, $P(O)(OR^{e'})(OR^{f'})$, $OP(O)(OR^{e'})(OR^{f'})$, $SiR^{e'}R^{f'}R^{g'}$, $C(O)R^{e'}$, $C(O)OR^{e'}$, $C(O)N(R^{e'})R^{f'}$, $OC(O)R^{e'}$, $OC(O)OR^{e'}$, $OC(O)N(R^{e'})R^{f'}$, $N(R^{e'})C(O)R^{f'}$, $N(R^{e'})C(O)OR^{f'}$, and $N(R^{e'})C(O)N(R^{f'})R^{g'}$, wherein $R^{e'}$, $R^{f'}$, and $R^{g'}$ are independently selected from H and optionally substituted $C_{1-6}$ alkyl, $C_{1-6}$ heteroalkyl, $C_{3-7}$ cycloalkyl, $C_{1-7}$ heterocycloalkyl, $C_{6-12}$ aryl, or $C_{1-12}$ heteroaryl, two or more of $R^{e'}$, $R^{f'}$, and $R^{g'}$ optionally being joined by one or more bonds to form one or more optionally substituted carbocycles and/or heterocycles, and/or $R^5+R^{5'}$, and/or $R^6+R^{6'}$, and/or $R^7+R^{7'}$ are independently =O, =S, =$NOR^{12}$, or =$NR^{12}$, $R^{12}$ being selected from H and optionally substituted $C_{1-3}$ alkyl, and/or $R^{5'}+R^{6'}$, and/or $R^{6'}+R^{7'}$, and/or $R^{7'}+R^{14'}$ are absent, which means that a double bond is present between the atoms bearing $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;

$X^1$ is selected from O, S, and $NR^{13}$, wherein $R^{13}$ is selected from H and optionally substituted $C_{1-8}$ alkyl;

$X^3$ is selected from O, S, and $NR^{15}$, wherein $R^{15}$ is selected from H and optionally substituted $C_{1-8}$ alkyl or $C_{1-8}$ acyl, or —$X^3$— represents —$X^{3a}$ and $X^{3b}$— wherein $X^{3a}$ is connected to the carbon to which $X^4$ is attached and $X^{3b}$ is connected to the phenyl ring ortho to $R^{10}$, wherein $X^{3a}$ is independently selected from H and optionally substituted $C_{1-8}$ alkyl or $C_{1-8}$ acyl, and $X^{3b}$ is selected from the same pool of substituents as $R^8$;

$X^4$ is selected from N and $CR^{16}$, wherein $R^{16}$ is selected from H and optionally substituted $C_{1-8}$ alkyl or $C_{1-8}$ acyl;

$X^5$ is selected from O, S, and $NR^{17}$, wherein $R^{17}$ is selected from H and optionally substituted $C_{1-8}$ alkyl or $C_{1-8}$ acyl;

$R^8$, $R^9$, $R^{10}$, and $R^{11}$ are each independently selected from H, OH, SH, $NH_2$, $N_3$, $NO_2$, NO, $CF_3$, CN, $C(O)NH_2$, $C(O)H$, $C(O)OH$, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, one or more of the optional substituents in $R^h$, $R^i$, and/or $R^j$ optionally being a water-soluble group, and two or more of $R^h$, $R^i$, and $R^j$ optionally being joined by one or more bonds to form one or more optionally substituted carbocycles and/or heterocycles, two or more of $R^8$, $R^9$, $R^{10}$, $R^{11}$, and $X^{3b}$ optionally being joined by one or more bonds to form one or more optionally substituted carbocycles and/or heterocycles;

a and b are independently selected from 0 and 1;
c is selected from 0 and 1;
provided that in a compound of formula (I):
a) at least one of $R^2$, $R^3$, $R^{3'}$, $R^4$, $R^{4'}$, $R^5$, $R^{5'}$, $R^6$, and $R^{6'}$ present is not hydrogen, and
b) when $R^2$, $R^3$, $R^{3'}$, $R^4$, $R^{4'}$, $R^5$, and $R^{5'}$ present are hydrogen, the atom that connects $R^6$ or $R^{6'}$ to the remainder of the compound contains at least two substituents other than hydrogen or fluorine that are each connected via a single bond to said atom, and
c) when $R^3$, $R^{3'}$, $R^4$, $R^{4'}$, $R^5$, and $R^{5'}$ present are hydrogen, $R^2$ is not methyl.

In another aspect, the present invention relates to a conjugate of a compound of formula (I) or (II).

In yet another aspect, this invention relates to a compound of formula (III):

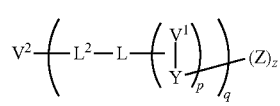

(III)

or a pharmaceutically acceptable salt, hydrate, or solvate thereof, wherein
$V^2$ is either absent or a functional moiety;
each $L^2$ is independently absent or a linking group linking $V^2$ to L;
each L is independently absent or a linking group linking $L^2$ to one or more $V^1$ and/or Y;
each $V^1$ is independently absent or a conditionally-cleavable or conditionally-transformable moiety, which can be cleaved or transformed by a chemical, photochemical, physical, biological, or enzymatic process;
each Y is independently absent or a self-eliminating spacer system which is comprised of 1 or more self-elimination spacers and is linked to $V^1$, optionally L, and one or more Z;
each p and q are numbers representing a degree of branching and are each independently a positive integer;
z is a positive integer equal to or smaller than the total number of attachment sites for Z;

each Z is independently a compound of formula (I) or (II) as defined hereinabove wherein one or more of $X^1$, $R^6$, $R^7$, $R^8$, $R^9$, $R^{10}$, and $R^{11}$ may optionally in addition be substituted by a substituent of formula (V):

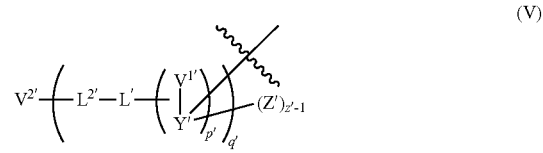

(V)

wherein each $V^{2'}$, $L^{2'}$, $L'$, $V^{1'}$, $Y'$, $Z'$, $p'$, $q'$, and $z'$ has the same meaning as defined for $V^2$, $L^2$, L, $V^1$, Y, Z, p, q, and z, respectively, the one or more substituents of formula (V) being independently connected to one or more of $X^1$, $R^6$, $R^7$, $R^8$, $R^9$, $R^{10}$, and $R^{11}$ via $Y'$, each Z being independently connected to Y through either $X^1$ or an atom in $R^6$, $R^7$, $R^8$, $R^9$, $R^{10}$, or $R^{11}$.

It is noted that z does not represent a degree of polymerization; hence z does not indicate that a number of moieties Z are connected to one another.

The present invention also relates to a compound of formula (IV):

(IV)

or a pharmaceutically acceptable salt, hydrate, or solvate thereof, wherein
RM is a reactive moiety and L, $V^1$, Y, Z, p; and z are as defined above, except that L is now linking RM to one or more $V^1$ and/or Y, and $V^1$, Y, and Z may contain protecting groups, and the one or more $V^{2'}$-$L^{2'}$ moieties optionally present in Z as defined hereinabove may optionally and independently be replaced by RM', which is a reactive moiety, and wherein, if there is more than 1 reactive moiety in (IV), some or all reactive moieties are the same or different. These linker-agent conjugates of formula (IV) may or may not be considered intermediates for compounds of formula (III).

Furthermore, this invention relates to the cyclopropyl ring-containing analogs of compounds of formulae (I) and (II), which are formed through rearrangement of and concomitant elimination of H—$R^1$ from the corresponding seco compounds of formulae (I) and (II) (FIG. 1). Said cyclopropyl ring-containing analogs are believed to be the active species, allegedly being formed from compounds of formulae (I) and (II) in vivo via said rearrangement.

This invention relates to enantiomerically pure and/or diastereomerically pure compounds of formulae (I)-(IV) as well as to enantiomeric and/or diastereomeric mixtures of compounds of formulae (I)-(IV).

Compounds of formulae (I) and (II) were unexpectedly found to exhibit a high in vitro cytotoxicity. This makes these compounds suitable for application in drug delivery purposes, including drug targeting and controlled release applications using compounds of formulae (III) and/or (IV).

DESCRIPTION OF THE INVENTION

Figure 1:
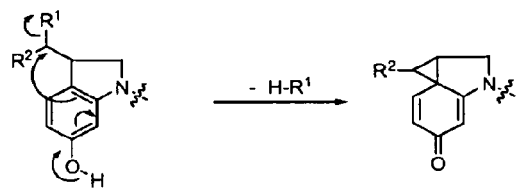
FIG. 1 illustrates the rearrangement of a seco compound to a cyclopropyl-containing compound.

The following detailed description is provided so that the invention may be more fully understood.

Definitions

Unless defined otherwise, all technical and scientific terms used herein generally have the same meaning as commonly understood by one of ordinary skill in the art.

The term "antibody", as used herein, refers to a full length immunoglobulin molecule, an immunologically active portion of a full-length immunoglobulin molecule, or a derivative of a full-length immunoglobulin molecule or an active portion thereof, i.e., a molecule that contains an antigen-binding site that immunospecifically binds an antigen of a target of interest or part thereof, such targets including, but not limited to, tumor cells. The immunoglobulin can be of any type (e.g., IgG, IgE, IgM, IgD, IgA, or IgY), class (e.g., IgG1, IgG2, IgG3, IgG4, IgA1, or IgA2), or subclass of immunoglobulin molecule. The immunoglobulin can be derived from any species, e.g., human, rodent (e.g., mouse, rat, or hamster), donkey, sheep, rabbit, goat, guinea pig, camelid, horse, cow, or chicken, but preferably, it is of human, murine, or rabbit origin. Antibodies useful in the invention include, but are not limited to, monoclonal, polyclonal, bispecific, human, humanized, or chimeric antibodies, single chain antibodies, Fv fragments, Fab fragments, F(ab') fragments, F(ab')$_2$ fragments, fragments produced by a Fab expression library, anti-idiotypic antibodies, CDRs, and epitope-binding fragments of any of the above that immunospecifically bind to an antigen-of-interest.

The term "leaving group" refers to a group that can be substituted by another group in a nucleophilic substitution reaction. Such leaving groups are well-known in the art, and examples include, but are not limited to, a halide (fluoride, chloride, bromide, and iodide), a sulfonate (e.g., an optionally substituted $C_{1-6}$ alkanesulfonate, such as methanesulfonate and trifluoromethanesulfonate, and an optionally substituted $C_{7-12}$ alkylbenzenesulfonate, such as p-toluenesulfonate), succinimide-N-oxide, p-nitrophenoxide, pentafluorophenoxide, tetrafluorophenoxide, a carboxylate, and an alkoxycarboxylate. For substitutions at saturated carbon, halides and sulfonates are preferred leaving groups.

The term "water-soluble group" refers to a functional group that is well solvated in aqueous environments and that imparts improved water solubility to the compound to which it is attached. Examples of water-soluble groups include, but are not limited to, polyalcohols, straight chain or cyclic saccharides, primary, secondary, tertiary, or quaternary amines and polyamines, sulfate groups, carboxylate groups, phosphate groups, phosphonate groups, ascorbate groups, glycols, including polyethylene glycols, and polyethers.

The term "substituted", when used as an adjective to "alkyl", "heteroalkyl", "cycloalkyl", "heterocycloalkyl", "aryl", "heteroaryl", and the like, indicates that said "alkyl", "heteroalkyl", "cycloalkyl", "heterocycloalkyl", "aryl", or "heteroaryl" group contains one or more substituents (not being hydrogen). Exemplary substituents include, but are not limited to, OH, =O, =S, =NR$^k$, =N—OR$^k$, SH, NH$_2$, NO$_2$, NO, N$_3$, CF$_3$, CN, OCN, SCN, NCO, NCS, C(O)NH$_2$, C(O)H, C(O)OH, halogen, R$^k$, SR$^k$, S(O)R$^k$, S(O)OR$^k$, S(O)$_2$ R$^k$, S(O)$_2$OR$^k$, OS(O)R$^k$, OS(O)OR$^k$, OS(O)$_2$R$^k$, OS(O)$_2$OR$^k$, OP(O)(OR$^k$)(OR$^l$), P(O)(OR$^k$)(OR$^l$), OR$^k$, NHR$^k$, N(R$^k$)R$^l$, $^+$N(R$^k$)(R$^l$)R$^m$, Si(R$^k$)(R$^l$)(R$^m$), C(O)R$^k$, C(O)OR$^k$, C(O)N(R$^k$)R$^l$, OC(O)R$^k$, OC(O)OR$^k$, OC(O)N(R$^k$)R$^l$, N(R$^k$)C(O)R$^l$, N(R$^k$)C(O)OR$^l$, N(R$^k$)C(O)N(R$^l$)R$^m$, and the thio derivatives of these substituents, or a protonated or deprotonated form of any of these substituents, wherein R$^k$, R$^l$, and R$^m$ are independently selected from H and optionally substituted $C_{1-15}$ alkyl, $C_{1-15}$ heteroalkyl, $C_{3-15}$ cycloalkyl, $C_{1-5}$ heterocycloalkyl, $C_{6-15}$ aryl, or $C_{1-5}$ heteroaryl, or a combination thereof, two or more of R$^k$, R$^l$, and R$^m$ optionally being joined by one or more bonds to form one or more optionally substituted carbocycles and/or heterocycles.

The term "aryl" as used herein refers to a carbocyclic aromatic substituent comprising 6-24 carbon atoms, which may consist of one ring or two or more rings fused together. Examples of aryl groups include, but are not limited to, phenyl, naphthyl, and anthracenyl.

The term "heteroaryl" as used herein refers to a carbocyclic aromatic substituent comprising 1 to 24 carbon atoms and at least one heteroatom selected from the group consisting of oxygen, nitrogen, sulfur, silicon, and phosphorus, which may consist of one ring or two or more rings fused together. Examples of heteroaryl groups include, but are not limited to, pyridinyl, furanyl, pyrrolyl, triazolyl, pyrazolyl, imidazolyl, thiophenyl, indolyl, benzofuranyl, benzimidazolyl, indazolyl, benzotriazolyl, benzisoxazolyl, and quinolinyl. In one embodiment, a heteroaryl group comprises 1 to 4 heteroatoms. It should be noted that "$C_1$ heteroaryl group" denotes that there is only one carbon present in the ring system of the heteroaromatic group. An example of such a heteroaromatic group is a tetrazolyl group.

The term "alkyl" as used herein refers to a straight chain or branched, saturated or unsaturated hydrocarbyl substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, 2-pentenyl, and 1-butynyl.

The term "heteroalkyl" as used herein refers to a straight chain or branched, saturated or unsaturated hydrocarbyl substituent in which at least one carbon atom is replaced by a heteroatom. Examples include, but are not limited to, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic cyclic hydrocarbyl substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein refers to a saturated or unsaturated non-aromatic cyclic hydrocarbyl substituent, which may consist of one ring or two or more rings fused together, wherein at least one carbon in one of the rings is replaced by a heteroatom. Examples include, but are not limited to, tetrahydrofuranyl, pyrrolidinyl, piperidinyl, 1,4-dioxanyl, decahydroquinolinyl, piperazinyl, oxazolidinyl, and morpholinyl. It should be noted that "$C_1$ heterocycloalkyl group" denotes that there is only one carbon present in the ring system of the heterocycloalkane. An example of such a group is a dioxiranyl group.

The number of carbon atoms that an "alkyl", "heteroalkyl", "cycloalkyl", "heterocycloalkyl", "aryl", "heteroaryl", and the like, may contain is indicated by a designation preceding said terms (i.e., $C_{1-10}$ alkyl means that said alkyl may contain from one to ten carbons).

The term "carbocycle" herein refers to a saturated or unsaturated cycloalkane or arene moiety, wherein the terms "cycloalkane" and "arene" are defined as parent moieties of the "cycloalkyl" and "aryl" substituents, respectively, as defined hereinabove.

The term "heterocycle" herein refers to a saturated or unsaturated heterocycloalkane or heteroarene moiety, wherein the terms "heterocycloalkane" and "heteroarene" are defined as parent moieties of the "heterocycloalkyl" and "heteroaryl" substituents, respectively, as defined hereinabove.

The extension "-ylene" as opposed to "-yl" in for example "alkylene" as opposed to "alkyl" indicates that said for example "alkylene" is a divalent moiety connected to one or two other moieties via one double bond or two covalent single bonds, respectively, as opposed to being a monovalent group connected to one moiety via one covalent single bond in said for example "alkyl". The term "alkylene" therefore refers to a straight chain or branched, saturated or unsaturated hydrocarbylene moiety; the term "heteroalkylene" as used herein refers to a straight chain or branched, saturated or unsaturated hydrocarbylene moiety in which at least one carbon is replaced by a heteroatom; the term "arylene" as used herein refers to a carbocyclic aromatic moiety, which may consist of one ring or two or more rings fused together; the term "heteroarylene" as used herein refers to a carbocyclic aromatic moiety, which may consist of one ring or two or more rings fused together, wherein at least one carbon in one of the rings is replaced by a heteroatom; the term "cycloalkylene" as used herein refers to a saturated or unsaturated non-aromatic cyclic hydrocarbylene moiety, which may consist of one ring or two or more rings fused together; the term "heterocycloalkylene" as used herein refers to a saturated or unsaturated non-aromatic cyclic hydrocarbylene moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing two or more attachment sites for adjacent moieties.

Certain compounds of the invention possess chiral centers and/or double bonds, and/or may have tautomers; the tautomeric, enantiomeric, diastereomeric, and geometric mixtures of two or more isomers, in any composition, as well as the individual isomers (including tautomers) are encompassed within the scope of the present invention. Whenever the term "isomer" is used, it refers to a tautomeric, enantiomeric, diastereomeric, and/or geometric isomer or to a mixture of two or more of these isomers, unless the context dictates otherwise.

The term "bond" herein refers to a covalent connection between two atoms and may refer to a single bond, a double bond, or a triple bond, or, if resonance structures are possible, the bond order of said bond may be different in two or more of these resonance structures. For example, if the bond is part of an aromatic ring, the bond may be a single bond in one resonance structure and a double bond in another resonance structure.

The compounds of the invention may also contain unnatural proportions of atomic isotopes at one or more atoms that constitute such compounds. All isotopic variations of the compounds of this invention, whether radioactive or not, are intended to be encompassed within the scope of this invention.

The phrase "pharmaceutically active salt" as used herein refers to a pharmaceutically acceptable organic or inorganic salt of a compound of the invention. For compounds containing one or more basic groups, e.g., an amine group, acid addition salts can be formed. For compounds containing one or more acidic groups, e.g., a carboxylic acid group, base addition salts can be formed. For compounds containing both acidic and basic groups, zwitterions may in addition be obtained as salts. When the compound of the invention comprises more than one charged atom or group, there may be multiple (distinct) counterions.

The phrase "pharmaceutically acceptable solvate" refers to an association of one or more solvent molecules and a compound of the invention. Examples of solvents that form pharmaceutically acceptable solvates include, but are not limited to, water, isopropyl alcohol, ethanol, methanol, DMSO, ethyl acetate, and acetic acid. When referring to water as a solvate, the term "hydrate" can be used.

The term "conjugate" hereinbelow refers to a compound of formula (III).

The term "linker-agent conjugate" hereinbelow refers to a compound of formula (IV).

The term "agent" hereinbelow refers to a compound of formula (I), (II), (I'), or (II').

The term "targeting moiety" refers to any moiety that specifically binds or reactively associates or complexes with a moiety specifically or in relative excess present at or near the target site, on, in, or near the target cell, or in (the proximity of) the target tissue or organ, e.g., a receptor, a receptor complex, substrate, antigenic determinant, or other receptive moiety, or that can target the conjugate to the target site via other mechanisms by virtue of its nature, e.g., through the EPR effect. Examples of a targeting moiety include, but are not limited to, an aptamer, an antibody or antibody fragment, a polymer, a dendrimer, a lectin, a biologic response modifier, an enzyme, a vitamin, a growth factor, a steroid, a sugar residue, an oligosaccharide residue, a carrier protein, and a hormone, or any combination thereof.

The phrase "moiety that improves the pharmacokinetic properties of the compound" refers to a moiety that changes the pharmacokinetic properties of a compound of this invention in such a way that a better therapeutic effect can be obtained. The moiety can for example increase the water solubility, increase the circulation time, or reduce immunogenicity.

The term "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are each directly attached to the moiety immediately to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_b$ with b being a number representing a degree of polymerization means that when b is 2, the formula reduces to A-B-B.

The term "single-release spacer" refers to a self-elimination spacer that can release one moiety upon self-immolation.

The term "multiple-release spacer" refers to a self-elimination spacer that can release two or more moieties upon repetitive self-immolation.

The term "electronic cascade spacer" refers to a self-elimination spacer, either branched or unbranched, which may self-eliminate through one or more 1,2+2n electronic cascade eliminations (n≥1).

The term "ω-amino aminocarbonyl cyclization spacer" refers to a self-elimination spacer that may eliminate through a cyclization process under formation of a cyclic ureum derivative.

The term "spacer system" refers to a single spacer moiety or to two or more of the same or different spacer moieties coupled together. A spacer system may be branched or unbranched and contain one or more attachment sites for Z as well as V$^1$ and optionally L.

In this document and in its claims, the verbs "to comprise", "to have", "to contain" and their conjugations are used in their non-limiting sense to mean that items that are "comprised", "had", or "contained" are included, but items non-specifically mentioned are not excluded. In addition, reference to an element by the indefinite article "a" or "an" does not exclude the possibility that more than one of the element is present; unless the context clearly requires that there be one and only one of the elements. The indefinite article "a" or "an" thus usually means "at least one".

In the generic structures throughout this description and in the claims letters are used to define structural elements. Some of these letters can be mistaken to represent an atom, such as C, N, O, P, K, B, F, S, U, V, W, I, and Y. To avoid confusion whenever these letters do not represent an atom they are given in bold typeface.

When there are one or more adjectives and/or adjective phrases to a noun that is a) the first in a list of nouns or b) that is anywhere in the middle of a list of nouns and said noun and adjectives together are preceded by the word "and" or "or", the adjectives do not only bear on said noun, but on all following nouns separately, unless the context dictates otherwise. This for example means that the phrase "optionally substituted C$_{1-4}$ alkyl, C$_{1-4}$ heteroalkyl, C$_{3-7}$ cycloalkyl, or C$_{1-7}$ heterocycloalkyl" should be read as "optionally substituted C$_{1-4}$ alkyl, optionally substituted C$_{1-4}$ heteroalkyl, optionally substituted C$_{3-7}$ cycloalkyl, or optionally substituted C$_{1-7}$ heterocycloalkyl" and that the phrase "C$_{1-4}$ alkyl, C$_{1-4}$ heteroalkyl, and optionally substituted C$_{3-7}$ cycloalkyl, C$_{6-8}$ aryl, or C$_{1-7}$ heterocycloalkyl" should be read as "C$_{1-4}$ alkyl, C$_{1-4}$ heteroalkyl, and optionally substituted C$_{3-7}$ cycloalkyl, optionally substituted C$_{6-8}$ aryl, or optionally substituted C$_{1-7}$ heterocycloalkyl".

Throughout this description and in the claims molecular structures or parts thereof are drawn. As usual in such drawings bonds between atoms are represented by lines, in some cases, to indicate stereochemistry, by bold or broken or wedged lines. Usually a line ending in space (a "loose" end), i.e., at one end not having another line or specific atom connected to it, represents a CH$_3$ group.

This is correct for the drawings representing the compounds of this invention. For those structures representing a structural element of the compounds of this invention a line ending in space may indicate the position of attachment of another structural element of the compound. This has been indicated with a wavy line perpendicular to and crossing the "loose" line in most drawings.

Furthermore, the structures or parts thereof have been drawn, under the assumption that the structures are read from left to right, meaning that for example in the drawings of compounds of formula (III) V$^2$ (if present) is always located on the left side and Z is always located on the right side of such structures.

The following abbreviations are used herein and have the indicated definitions: AIBN: 2,2'-azobis(2-methylpropionitril); DMF: N,N-dimethylformamide; EDC: 1-ethyl-3-(3-dimethylaminopropyl)-carbodiimide; EtOAc: ethyl acetate; THF: tetrahydrofuran; TTMSS: tris(trimethylsilyl)silane.

Agents, Linker-Agent Conjugates, and Conjugates

The present invention provides novel agents that belong to the class of the DNA-alkylating agents CC-1065 and the duocarmycins. Furthermore, the invention relates to novel conjugates of these agents and to linker-agent conjugates, which may or may not serve as intermediates for said conjugates.

The agents of the present invention are deemed to be used to treat an illness that is characterized by undesired (cell) proliferation. For example, an agent of this invention can be used to treat a tumor, cancer, an autoimmune disease, or an infectious disease.

The conjugates of the present invention are in one aspect deemed to be applicable to target agents of formulae (I) and (II) to a specific target site where the conjugate can be converted into one or more agents or be induced to be converted into one or more of said agents. This invention can furthermore find application in (non-specific) controlled release of one or more of said agents from a conjugate, with the aim of for example enhancing pharmacokinetic properties.

Compounds of formulae (I) and (II) were unexpectedly found to exhibit a high in vitro cytotoxicity, which makes these compounds suitable for application in drug delivery purposes. An explanation for the high in vitro cytotoxicity may be steric shielding of the alkylating site in a compound of formula (I) or (II).

Agents

In one aspect, the present invention provides a compound of formula (I) or (II):

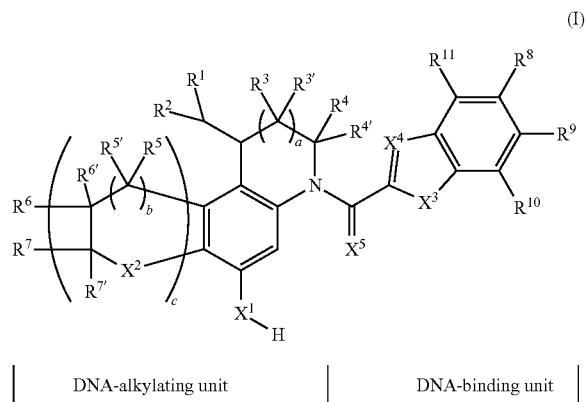

-continued (II)

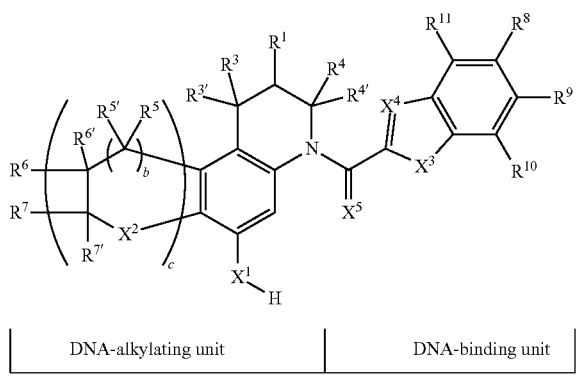

| DNA-alkylating unit | DNA-binding unit | or a pharmaceutically acceptable salt, hydrate, or solvate thereof, wherein $R^1$ is a leaving group;

$R^2$ is selected from H, $N_3$, $NO_2$, NO, $CF_3$, CN, $C(O)NH_2$, $C(O)H$, $C(O)OH$, halogen, $R^b$, $SR^b$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^b$, $N(R^b)R^c$, $^+N(R^b)(R^c)R^d$, $P(O)(OR^a)(OR^{a'})$, $OP(O)(OR^a)(OR^{a'})$, $SiR^aR^{a'}R^{a''}$, $C(O)R^a$, $C(O)OR^a$, $C(O)N(R^a)R^{a'}$, $OC(O)R^a$, $OC(O)OR^a$, $OC(O)N(R^a)R^{a'}$, $N(R^a)C(O)R^{a'}$, $N(R^a)C(O)OR^{a'}$, and $N(R^a)C(O)N(R^{a'})R^{a''}$, wherein $R^a$, $R^{a'}$, and $R^{a''}$ are independently selected from H and optionally substituted $C_{1-3}$ alkyl or $C_{1-3}$ heteroalkyl, and $R^b$, $R^c$, and $R^d$ are independently selected from optionally substituted $C_{1-3}$ alkyl and $C_{1-3}$ heteroalkyl;

$R^3$, $R^{3'}$, $R^4$, and $R^{4'}$ are independently selected from H and optionally substituted $C_{1-3}$ alkyl, wherein two or more of $R^2$, $R^3$, $R^{3'}$, $R^4$, and $R^{4'}$ are optionally joined by one or more bonds to form one or more optionally substituted carbocycles and/or heterocycles, and/or $R^3+R^{3'}$ and/or $R^4+R^{4'}$ are independently =O, =S, =NOR$^{18}$, or =NR$^{18}$, $R^{18}$ being selected from H and optionally substituted $C_{1-3}$ alkyl;

$X^2$ is selected from O, $C(R^{14})(R^{14'})$, and $NR^{14}$, wherein $R^{14}$ is selected from H and optionally substituted $C_{1-8}$ alkyl or $C_{1-8}$ acyl and wherein $R^{14'}$ is absent or is selected from H and optionally substituted $C_{1-8}$ alkyl or $C_{1-8}$ acyl;

$R^5$ and $R^{5'}$ are independently selected from H, OH, SH, $NH_2$, $N_3$, $NO_2$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^e)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or hetcrocycles, and $R^6$, $R^{6'}$, $R^7$, and $R^{7'}$ are independently selected from H, OH, SH, $NH_2$, $N_3$, $NO_2$, NO, $CF_3$, CN, $C(O)NH_2$, $C(O)H$, $C(O)OH$, halogen, $R^{e'}$, $SR^{e'}$, $S(O)R^{e'}$, $S(O)_2R^{e'}$, $S(O)OR^{e'}$, $S(O)_2OR^{e'}$, $OS(O)R^{e'}$, $OS(O)_2R^{e'}$, $OS(O)OR^{e'}$, $OS(O)_2OR^{e'}$, $OR^{e'}$, $NHR^{e'}$, $N(R^{e'})R^{f'}$, $^+N(R^{e'})(R^{f'})R^{g'}$, $P(O)(OR^{e'})(OR^{f'})$, $OP(O)(OR^{e'})(OR^{f'})$, $SiR^{e'}R^{f'}R^{g'}$, $C(O)R^{e'}$, $C(O)OR^{e'}$, $C(O)N(R^{e'})R^{f'}$, $OC(O)R^{e'}$, $OC(O)OR^{e'}$, $OC(O)N(R^{e'})R^{f'}$, $N(R^{e'})C(O)R^{f'}$, $N(R^{e'})C(O)OR^{f'}$, and $N(R^{e'})C(O)N(R^{f'})R^{g'}$, wherein $R^{e'}$, $R^{f'}$, and $R^{g'}$ are independently selected from H and optionally substituted $C_{1-6}$ alkyl, $C_{1-6}$ heteroalkyl, $C_{3-7}$ cycloalkyl, $C_{1-7}$ heterocycloalkyl, $C_{6-12}$ aryl, or $C_{1-12}$ heteroaryl, two or more of $R^{e'}$, $R^{f'}$, and $R^{g'}$ optionally being joined by one or more bonds to form one or more optionally substituted carbocycles and/or heterocycles, and/or $R^5+R^{5'}$, and/or $R^6+R^{6'}$, and/or $R^7+R^{7'}$ are independently =O, =S, =NOR$^{12}$, or =NR$^{12}$, $R^{12}$ being selected from H and optionally substituted $C_{1-3}$ alkyl, and/or $R^{5'}+R^{6'}$, and/or $R^{6'}+R^{7'}$, and/or $R^{7'}+R^{14'}$ are absent, which means that a double bond is present between the atoms bearing $R^{5'}$ and $R^{6'}$, and/or $R^{6'}$ and $R^{7'}$, and/or $R^{7'}$ and $R^{14}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;

$X^1$ is selected from O, S, and $NR^{13}$, wherein $R^{13}$ is selected from H and optionally substituted $C_{1-8}$ alkyl;

$X^3$ is selected from O, S, and $NR^{15}$, wherein $R^{15}$ is selected from H and optionally substituted $C_{1-8}$ alkyl or $C_{1-8}$ acyl, or —$X^3$— represents —$X^{3a}$ and $X^{3b}$— wherein $X^{3a}$ is connected to the carbon to which $X^4$ is attached and $X^{3b}$ is connected to the phenyl ring ortho to $R^{10}$, wherein $X^{3a}$ is independently selected from H and optionally substituted $C_{1-8}$ alkyl or $C_{1-8}$ acyl, and $X^{3b}$ is selected from the same pool of substituents as $R^8$;

$X^4$ is selected from N and $CR^{16}$, wherein $R^{16}$ is selected from H and optionally substituted $C_{1-8}$ alkyl or $C_{1-8}$ acyl;

$X^5$ is selected from O, S, and $NR^{17}$, wherein $R^{17}$ is selected from H and optionally substituted $C_{1-8}$ alkyl or $C_{1-8}$ acyl;

$R^8$, $R^9$, $R^{10}$, and $R^{11}$ are each independently selected from H, OH, SH, $NH_2$, $N_3$, $NO_2$, NO, $CF_3$, CN, $C(O)NH_2$, $C(O)H$, $C(O)OH$, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, one or more of the optional substituents in $R^h$, $R^i$, and/or $R^j$ optionally being a water-soluble group, and two or more of $R^h$, $R^i$, and $R^j$ optionally being joined by one or more bonds to form one or more optionally substituted carbocycles and/or heterocycles, two or more of $R^8$, $R^9$, $R^{10}$, $R^{11}$, and $X^{3b}$ optionally being joined by one or more bonds to form one or more optionally substituted carbocycles and/or heterocycles;

a and b are independently selected from 0 and 1;

c is selected from 0 and 1;

provided that in a compound of formula (I):

a) at least one of $R^2$, $R^3$, $R^{3'}$, $R^4$, $R^{4'}$, $R^5$, $R^{5'}$, $R^6$, and $R^{6'}$ present is not hydrogen, and b) when $R^2$, $R^3$, $R^{3'}$, $R^4$, $R^{4'}$, $R^5$, and $R^{5'}$ present are hydrogen, the atom that connects $R^6$ or $R^{6'}$ to the remainder of the compound contains at least two substituents other than hydrogen or fluorine that are each connected via a single bond to said atom, and c) when $R^3$, $R^{3'}$, $R^4$, $R^{4'}$, $R^5$, and $R^{5'}$ present are hydrogen, $R^2$ is not methyl.

In a further aspect, this invention relates to a compound of formula (I') or (II'):

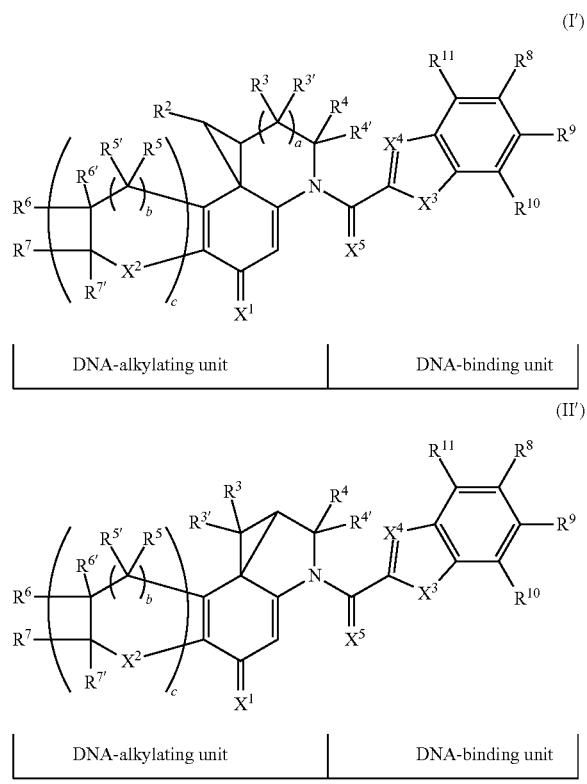

wherein all substituents have the same meaning as described for compounds of formulae (I) and (II) above. Compounds of formulae (I) and (II) are alleged to be converted to (I') and (II'), respectively, in vivo with concomitant elimination of H—$R^1$, as schematically illustrated in FIG. 1 for a compound of formula (I).

Therefore, this invention relates to a compound of formula (I') or (II'), said compound comprising a cyclopropyl group, which can be formed through rearrangement of and concomitant elimination of H—$R^1$ from a compound of formula (I) or (II).

It should be understood that in this entire document, when referring to a compound of formula (I) or (II), this includes reference to a compound of formula (I') or (II'), respectively, unless structural parts of (I) and (II) not present in (I') and (II') are concerned or the context dictates otherwise. Similarly, when referring to a structural part (fragment), linker-agent conjugate, or conjugate of formula (I) or (II), this includes reference to a similar structural part (fragment), linker-agent conjugate, or conjugate of formula (I') or (II'), respectively, unless structural parts of (I) and (II) not present in (I') and (II') are concerned or the context dictates otherwise.

It should also be understood that when reference is made to a compound of formula (I) or (II) and the scope of $R^2$ is specified, this specification only affects a compound of formula (I) as $R^2$ is absent in a compound of formula (II). Therefore, wherever it reads "$R^2$" in this document, one could read "$R^2$ (if present)".

It should further be understood that this invention relates to enantiomerically pure and/or diastereomerically pure compounds of formulae (I) and (II) as well as to enantiomeric and/or diastereomeric mixtures of compounds of formulae (I) and (II).

Considerations about substituent effects in compounds of formulae (I) and (II) and their cyclopropyl-containing analogs given in this document are presented without consenting to a specific mechanism of action for compounds of formulae (I) and (II) and their cyclopropyl-containing analogs.

Compounds of formula (I) and (II) can be considered to be built up of a DNA-binding unit and a DNA-alkylating unit, as indicated in the figures above.

The DNA-alkylating unit of compounds of formulae (I) and (II) is considered to contain the site of alkylation. Alkylation of DNA may occur through attack of DNA on the carbon bearing $R^1$ in a compound of formula (I) or (II) or on that same carbon in the cyclopropyl-containing analog of said compound.

In one embodiment, this invention relates to a compound of formula (I). In another embodiment, this invention relates to a compound of formula (II).

$R^1$ in a compound of formula (I) or (II) is a leaving group.

In one embodiment, the leaving group $R^1$ is selected from halogen, azide ($N_3$), carboxylate [$OC(O)R''$], carbonate [$OC(O)OR''$], carbamate [$OC(O)N(R'')R'''$], and $OS(O)_2R^o$, wherein $R''$ and $R'''$ are independently selected from optionally substituted $C_{1-6}$ alkyl and $C_{1-6}$ heteroalkyl and wherein $R^o$ is selected from $C_{1-6}$ perhaloalkyl and optionally substituted $C_{1-6}$ alkyl, benzyl, or phenyl. In one embodiment, $R^1$ is selected from halogen and $OS(O)_2R^o$. In another embodiment, the leaving group $R^1$ in a compound of formula (I) or (II) is a halogen. In another embodiment, $R^1$ is selected from chloride (Cl), bromide (Br), and iodide (I). In yet another embodiment, $R^1$ is chloride (Cl). In yet another embodiment, $R^1$ is bromide (Br). In yet another embodiment, $R^1$ is $OS(O)_2R^o$ In yet another embodiment, $R^1$ is selected from triflate [$OS(O)_2CF_3$], tosylate [$OS(O)_2C_6H_4CH_3$], and mesylate [$OS(O)_2CH_3$].

By varying the leaving group $R^1$, one may tune the alkylating activity of the seco agents and affect the transformation rate of a seco agent to a cyclopropyl-containing agent of formula (I') or (II'). If the leaving capability of $R^1$ is too good, this may cause the seco agent to become an (aspecific) alkylating agent as well, which may decrease the cytotoxicity quotient of conjugates of compounds of formulae (I) and (II) as the agent may be able to alkylate while still being bound in the conjugate. On the other hand, if $R^1$ is too bad a leaving group, the seco agent may not close to form a cyclopropyl-containing agent, believed to be the active species, which may reduce its cytotoxicity and, most likely, reduce the cytotoxicity quotient. Therefore, in one embodiment, the Swain-Scott parameter s of the alkylating site is larger than 0.3. In other embodiments, the Swain-Scott parameter s is larger than 0.5 or 0.7 or 1.0.

The size of $R^1$ may affect the non-DNA alkylation rate of a compound of formula (I) or (II) or a conjugate thereof. If $R^1$ is a relatively bulky group, aspecific alkylation may be reduced as the carbon bearing $R^1$ is somewhat shielded.

Another means to tune the alkylating activity of the seco agents and their cyclopropyl-containing derivatives may be to somewhat shield the carbon to which the leaving group $R^1$ is attached or on which nucleophilic attack can occur by choosing at least one of $R^2$, $R^3$, $R^{3'}$, $R^4$, $R^{4'}$, $R^5$, $R^{5'}$, $R^6$, and $R^{6'}$ present to be other than hydrogen. Shielding of said carbon may reduce aspecific alkylation by compounds of formulae (I) and (II) and their cyclopropyl-containing analogs and by their conjugates as well. Although introduction of steric hindrance may also affect the DNA alkylation rate, it may be reasonable to assume that aspecific alkylation may be affected relatively more than DNA alkylation as the latter occurs presumably after the agent is ideally positioned for nucleophilic attack being bound to the DNA minor groove. The carbon bearing $R^1$ in a compound of formula (II), being a secondary carbon atom, is already somewhat shielded in comparison to the carbon bearing $R^1$ in a compound of formula (I) when $R^2$ is H. In this respect, a compound of formula (II) may be compared to a compound of formula (I) in which $R^2$ is other than hydrogen. Further shielding may however be accomplished by choosing one or more of $R^3$, $R^{3'}$, $R^4$, $R^{4'}$, $R^5$, $R^{5'}$, $R^6$, and $R^{6'}$ present to be other than hydrogen.

In one embodiment, $R^2$ is hydrogen.

In another embodiment, $R^2$ is selected from $N_3$, $NO_2$, NO, $CF_3$, CN, $C(O)NH_2$, $C(O)H$, $C(O)OH$, halogen, $R^b$, $SR^b$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^b$, $N(R^b)R^c$, $^+N(R^b)(R^c)R^d$, $P(O)(OR^a)(OR^{a'})$, $OP(O)(OR^a)(OR^{a'})$, $SiR^aR^{a'}R^{a''}$, $C(O)R^a$, $C(O)OR^a$, $C(O)N(R^a)R^{a'}$, $OC(O)R^a$, $OC(O)OR^a$, $OC(O)N(R^a)R^{a'}$, $N(R^a)C(O)R^a$, $N(R^a)C(O)OR^a$, and $N(R^a)C(O)N(R^{a'})R^{a''}$, wherein $R^a$, $R^{a'}$, and $R^{a''}$ are independently selected from H and optionally substituted $C_{1-3}$ alkyl or $C_{1-3}$ heteroalkyl, and $R^b$, $R^c$, and $R^d$ are independently selected from optionally substituted $C_{1-3}$ alkyl and $C_{1-3}$ heteroalkyl.

In one embodiment, $R^2$ is optionally substituted $C_{1-3}$ alkyl. In another embodiment, $R^2$ is selected from methyl, ethyl, propyl, and isopropyl. In another embodiment, $R^2$ is methyl. In other embodiments, $R^2$ is ethyl or propyl or isopropyl.

In a further embodiment, $R^2$ is selected from $N_3$, halogen, $OS(O)_2R^a$, $CF_3$, $NO_2$, $N(R^b)R^c$, $OR^b$ $C(O)R^a$, $C(O)OR^a$, $OC(O)R^a$, $OC(O)OR^a$, $OC(O)N(R^a)R^{a'}$, and $C(O)N(R^a)R^a$.

In another embodiment, $R^2$ is selected from chloride (Cl), bromide (Br), azide ($N_3$), $CF_3$, $NO_2$, methoxy (OMe), and acetyl [$C(O)CH_3$].

In another embodiment, $R^2$ is selected from chloride and bromide. In a further embodiment, $R^2$ is chloride. In another further embodiment, $R^2$ is bromide. In other embodiments, $R^2$ is azide ($N_3$) or $CF_3$ or $NO_2$ or methoxy (OMe) or acetyl [$C(O)CH_3$].

$R^1$ and $R^2$ may be equal to each other. In such a case, the synthesis of a compound of formula (I) may be accomplished in a higher yield and/or with more ease as the compound contains one less chiral center than when substituents $R^1$ and $R^2$ are different from each other and $R^2$ is not hydrogen.

In one embodiment, $R^1$ and $R^2$ are equal to each other. In another embodiment, $R^1$ and $R^2$ are both either bromide or chloride. In another embodiment, $R^1$ and $R^2$ are both chloride (Cl). In another embodiment, $R^1$ and $R^2$ are both bromide (Br).

Alternatively, or simultaneously, steric shielding of the carbon bearing $R^1$ may be introduced by choosing one or more of $R^3$, $R^{3'}$, $R^4$, and $R^{4'}$ to be other than hydrogen. In one embodiment, $R^3$, $R^{3'}$, $R^4$, and $R^{4'}$ are each H. In another embodiment, $R^3$ and $R^{3'}$ are both H. In another embodiment, $R^4$ and $R^{4'}$ are both H. In another embodiment, one of $R^3$ and $R^{3'}$ is $C_{1-3}$ alkyl while the other is H. In another embodiment, one of $R^4$ and $R^{4'}$ is $C_{1-3}$ alkyl while the other is H. In another embodiment, one of $R^3$ and $R^{3'}$ is $C_{1-3}$ alkyl and one of $R^4$ and $R^{4'}$ is $C_{1-3}$ alkyl while the others are H. In another embodiment, both $R^3$ and $R^{3'}$ are independently $C_{1-3}$ alkyl. In another embodiment, both $R^4$ and $R^{4'}$, are independently $C_{1-3}$ alkyl.

The alkylating activity of a compound of formula (I) or (II) or its cyclopropyl-containing analog may also be affected by the nature of $X^1$. The nature of $X^1$ may affect the rate at which and the conditions under which the seco agents ring close to the cyclopropyl analogs and/or the rate at which the cyclopropyl ring is opened by nucleophilic attack (by DNA), and thus affect the alkylation behavior. In one embodiment, $X^1$ is O. In another embodiment, $X^1$ is $NR^{13}$.

The substituents $R^5$, $R^{5'}$, $R^6$, $R^{6'}$, $R^7$, $R^{7'}$, and $X^2$ as well as the size of the ring(s) connected to the left-hand side of the ring bearing $X^1$ may for example, each independently or two or more taken together, affect the pharmacokinetic properties of the agent, affect the water solubility, affect the aggregation behavior, affect the DNA alkylation process, or affect the DNA binding strength.

Furthermore, especially $R^5$ and $R^{5'}$, and to some degree $R^6$ and $R^{6'}$ as well, may also affect the degree of shielding of the carbon on which nucleophilic attack can occur.

In one embodiment, $R^5$ and $R^{5'}$ are both H, or $R^5$ is H and $R^{5'}$ is absent. In another embodiment, at least one of $R^5$ and $R^{5'}$ is not hydrogen. In another embodiment, $R^5$ is not hydrogen. In another embodiment, $R^5$ is selected from OH, SH, $NH_2$, $N_3$, $NO_2$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles. In another embodiment, $R^5$ is selected from H, OH, SH, $NH_2$, $N_3$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles. In another embodiment, $R^5$ is selected from H, OH, SH, $NH_2$, $N_3$, $NO_2$, NO, $CF_3$, CN, $C(O)NH_2$, $C(O)H$, $C(O)OH$, halogen, $R^{e''}$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, $R^{e''}$ is selected from H, substituted methyl, and optionally substituted $C_{2-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles. In yet another embodiment, $R^5$ is selected from nitro, halogen, amino, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkyloxy, $C_{1-3}$ alkylcarbonyloxy, $C_{1-3}$ alkylaminocarbonyloxy, or $C_{1-3}$ alkyl. In yet another embodiment, $R^5$ is optionally substituted linear $C_{1-3}$ alkyl. In another embodiment, $R^5$ is unsubstituted linear $C_{1-3}$ alkyl. In another embodiment, $R^5$ is selected from methyl, ethyl, propyl, isopropyl, nitro, $CF_3$, F, Cl, Br, methoxy, amino (NH$_2$), methylamino, formyl, hydroxymethyl, and dimethylamino. In another embodiment, R$^5$ is methyl. In other embodiments, R$^5$ is ethyl or propyl or isopropyl.

In one embodiment, R$^6$ and R$^{6'}$ are hydrogen, or R$^6$ is hydrogen and R$^{6'}$ is absent. In another embodiment, at least one of R$^6$ and R$^{6'}$ is not hydrogen. In another embodiment, R$^6$ is not hydrogen.

In another embodiment, R$^6$ is a sterically bulky group, meaning that the atom of R$^6$ that is connected to the remainder of a compound of formula (I) or (II) contains at least two substituents other than hydrogen or fluorine that are each connected via a single bond to said atom. In yet another embodiment, R$^6$ is selected from tert-butyl and isopropyl. In another embodiment, R$^6$ is tert-butyl. In yet another embodiment, R$^6$ is isopropyl.

Although the alkylation rate and efficiency of compounds of formulae (I) and (II) may be tuned in several ways, in one aspect of this invention, this is achieved by introducing steric shielding choosing for a compound of formula (I) at least one of R$^2$, R$^3$, R$^{3'}$, R$^4$, R$^{4'}$, R$^5$, R$^{5'}$, R$^6$, and R$^{6'}$ present to be other than hydrogen and for a compound of formula (II) optionally one or more of R$^2$, R$^3$, R$^1$, R$^4$, R$^{4'}$, R$^5$, R$^{5'}$, R$^6$, and R$^{6'}$ present to be other than hydrogen. Substituents should not cause too much steric hindrance, however, especially when more than one of these substituents is other than hydrogen, as this might adversely affect DNA alkylation. Furthermore, it may provide for less efficient binding in the DNA minor groove and may pose synthetic difficulties. In one embodiment, only one of R$^2$, R$^3$, R$^{3'}$, R$^4$, R$^{4'}$, R$^5$, R$^{5'}$, R$^6$, and R$^{6'}$ present is other than hydrogen. In another embodiment, two of R$^2$, R$^3$, R$^{3'}$, R$^4$, R$^{4'}$, R$^5$, R$^{5'}$, R$^6$, and R$^{6'}$ present are other than hydrogen and at least one of these two is a methyl group or a group of similar size, meaning that its van der Waals radius is no more than twice as large as that of a methyl group. In yet another embodiment, three of R$^2$, R$^3$, R$^{3'}$, R$^4$, R$^{4'}$, R$^5$, R$^{5'}$, R$^6$, and R$^{6'}$ present are other than hydrogen and these three each independently are a methyl group or a group of similar size, meaning that its van der Waals radius is no more than twice as large as that of a methyl group.

In one aspect of this invention, compounds of formulae (I) and (II) are represented by compounds of formulae (Ia) and (IIa), respectively:

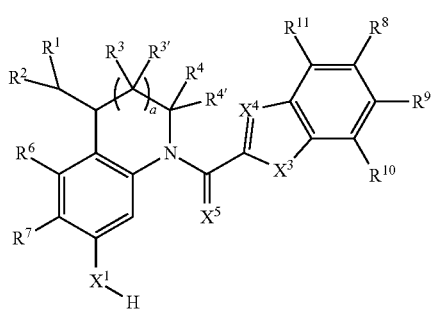

(Ia)

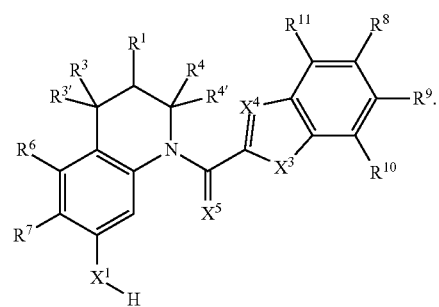

(IIa)

In one embodiment, R$^6$ and R$^7$ in (Ia) or (IIa) are both H.

R$^6$ may be a sterically bulky group such that the carbon bearing R$^1$ is somewhat shielded. In one embodiment, R$^6$ is a tert-butyl group; in another embodiment, R$^6$ is an isopropyl group.

In another aspect, compounds of formulae (I) and (II) are represented by compounds of formulae (Ib) and (IIb), respectively:

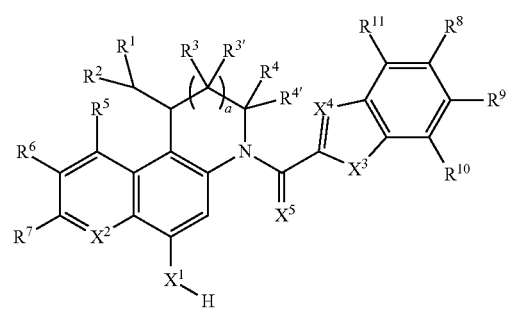

(Ib)

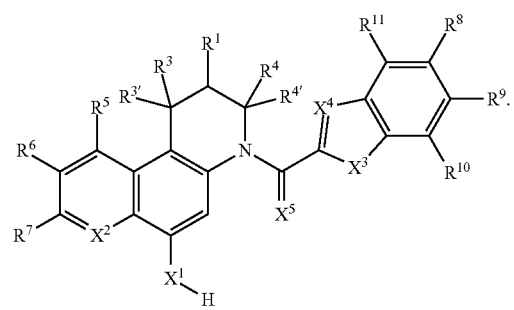

(IIb)

In one embodiment, X$^2$ in (Ib) or (IIb) is N.
In another embodiment, X$^2$ in (Ib) or (IIb) is CH.
In another embodiment, R$^5$, R$^6$, and R$^7$ in (Ib) or (IIb) are each H.
In another embodiment, R$^5$, R$^6$, and R$^7$ in (Ib) or (IIb) are each H and X$^2$ is CH.
In another embodiment, R$^5$ and R$^7$ in (Ib) or (IIb) are each H and R$^6$ is CO$_2$Me.
In another embodiment, R$^5$ and R$^7$ in (Ib) or (IIb) are each H and R$^6$ is OMe.
In another embodiment, R$^5$ and R$^7$ in (Ib) or (IIb) are each H and R$^6$ is CN.
In yet another embodiment, R$^5$ in (Ib) or (IIb) is selected from nitro, halogen, amino, hydroxy, and optionally substituted C$_{1-3}$ alkylamino, di(C$_{1-3}$ alkyl)amino, C$_{1-3}$ alkylcarbonylamino, $C_{1-3}$ alkoxycarbonylamino, $C_{1-3}$ alkyloxy, $C_{1-3}$ alkylcarbonyloxy, $C_{1-3}$ alkylaminocarbonyloxy, or $C_{1-3}$ alkyl. In yet another embodiment, $R^5$ in (Ib) or (IIb) is optionally substituted linear $C_{1-3}$ alkyl. In another embodiment, $R^5$ in (Ib) or (IIb) is unsubstituted linear $C_{1-3}$ alkyl. In another embodiment, $R^5$ in (Ib) or (IIb) is methyl. In other embodiments, $R^5$ in (Ib) or (IIb) is ethyl or propyl or isopropyl.

In yet another aspect, compounds of formulae (I) and (II) are represented by compounds of formulae (Ic) and (IIc), respectively:

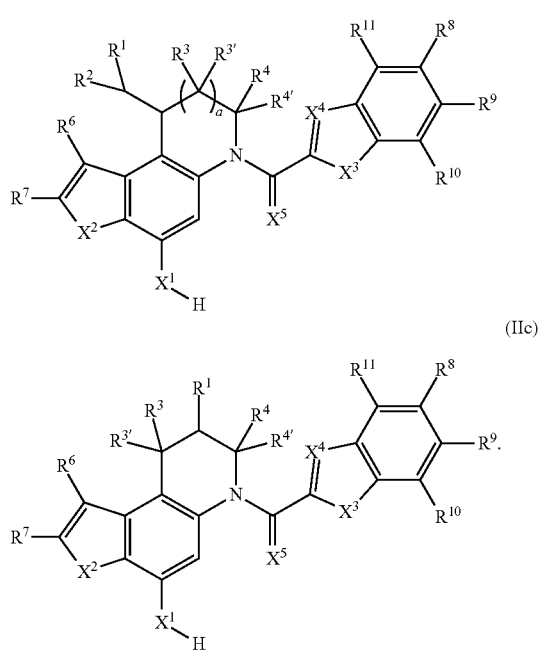

In one embodiment, $X^2$ in (Ic) or (IIc) is NH.

In another embodiment, $R^6$ and $R^7$ in (Ic) or (IIc) are H and $CO_2CH_3$, respectively, and $X^2$ is NH.

In another embodiment, $R^7$ and $R^6$ in (Ic) or (IIc) are H and $CO_2CH_3$, respectively, and $X^2$ is NH.

In another embodiment, $R^6$ in (Ic) or (IIc) is $CH_3$ and $X^2$ is NH.

In yet another aspect, compounds of formulae (I) and (II) are represented by compounds of formulae (Id) and (IId), respectively:

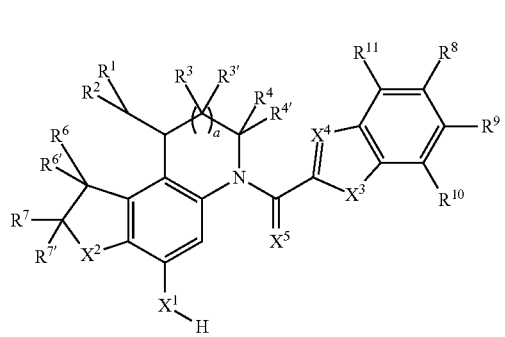

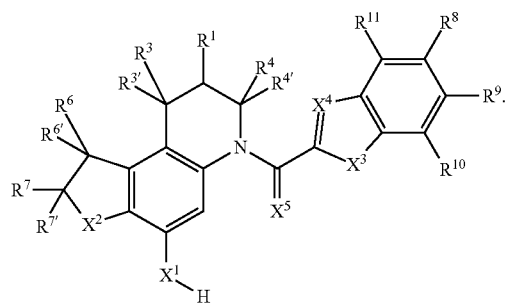

In one embodiment, $X^2$ in (Id) or (IId) is NH.

In another embodiment, $R^6$ and $R^{6'}$ in (Id) or (IId) together are $=O$.

In another embodiment, $R^7$ and $R^{7'}$ in (Id) or (IId) are $CO_2CH_3$ and $CH_3$, respectively.

In another embodiment, in a compound of formula (Id) or (IId), $X^2$ is NH, $R^6$ and $R^{6'}$ together are $=O$, and $R^7$ and $R^{7'}$ are $CO_2CH_3$ and $CH_3$, respectively.

In one embodiment, c=1 and b=1. In another embodiment, c=1 and b=0. In another embodiment, a=0.

In one embodiment, $R^2$ in a compound of formula (I) is optionally substituted $C_{1-3}$ alkyl and $R^3$, $R^{3'}$, $R^4$, $R^{4'}$, $R^5$, $R^{5'}$, $R^6$, and $R^{6'}$ present are hydrogen. In another embodiment, $R^2$ in a compound of formula (I) is selected from methyl, ethyl, propyl, and isopropyl, and $R^3$, $R^{3'}$, $R^4$, $R^{4'}$, $R^5$, $R^{5'}$, $R^6$, and $R^{6'}$ present are each hydrogen. In a further embodiment, $R^2$ in a compound of formula (I) is selected from $N_3$, halogen, $OS(O)_2R^a$, $CF_3$, $NO_2$, $N(R^b)R^c$, $OR^b$, $C(O)R^a$, $C(O)OR^a$, $OC(O)R^a$, $OC(O)OR^a$, $OC(O)N(R^a)R^{a'}$, and $C(O)N(R^a)R^{a'}$ and $R^3$, $R^{3'}$, $R^4$, $R^{4'}$, $R^5$, $R^{5'}$, $R^6$, and $R^{6'}$ present are each hydrogen. In another embodiment, $R^2$ in a compound of formula (I) is selected from chloride and bromide and $R^3$, $R^{3'}$, $R^4$, $R^{4'}$, $R^5$, $R^{5'}$, $R^6$. and $R^{6'}$ present are each hydrogen.

In one embodiment, $R^2$, $R^5$, $R^{5'}$, $R^6$, and $R^{6'}$ present are each hydrogen and one of $R^3$, $R^{3'}$, $R^4$, and $R^{4'}$ is selected from $C_{1-3}$ alkyl. In another embodiment, $R^2$, $R^5$, $R^{5'}$, $R^6$, and $R^{6'}$ present are each hydrogen and one of $R^3$, $R^{3'}$, $R^4$, and $R^{4'}$ is selected from methyl. In another embodiment, $R^2$, $R^5$, $R^{5'}$, $R^6$, and $R^{6'}$ present are each hydrogen and two of $R^3$, $R^{3'}$, $R^4$, and $R^{4'}$ are independently selected from $C_{1-3}$ alkyl. In yet another embodiment, $R^2$, $R^5$, $R^{5'}$, $R^6$ and $R^{6'}$ present are each hydrogen and two of $R^3$, $R^{3'}$, $R^4$, and $R^{4'}$ are methyl.

In yet another embodiment, $R^5$ is selected from nitro, halogen, amino, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkyloxy, $C_{1-3}$ alkylcarbonyloxy, $C_{1-3}$ alkylaminocarbonyloxy, or $C_{1-3}$ alkyl, and $R^2$, $R^3$, $R^{3'}$, $R^4$, $R^{4'}$, $R^{5'}$, $R^6$ . . . and $R^{6'}$ present are each H. In yet another embodiment, $R^5$ is optionally substituted linear $C_{1-3}$ alkyl and $R^2$, $R^3$, $R^{3'}$, $R^4$, $R^{4'}$, $R^{5'}$, $R^6$, and $R^{6'}$ present are each hydrogen. In another embodiment, $R^5$ is unsubstituted linear $C_{1-3}$ alkyl and $R^2$, $R^3$, $R^{3'}$, $R^4$, $R^{4'}$, $R^{5'}$, $R^6$, and $R^{6'}$ present are each hydrogen. In another embodiment, $R^5$ is selected from methyl, ethyl, propyl, isopropyl, nitro, $CF_3$, F, Cl, Br, methoxy, amino, methylamino, formyl, hydroxymethyl, and dimethylamino, and $R^2$, $R^3$, $R^{3'}$, $R^4$, $R^{4'}$, $R^{5'}$, $R^6$, and $R^{6'}$ present are each hydrogen. In another embodiment, $R^5$ is not methyl when $R^8$ is N,N-dimethylaminoethoxy, $R^9$, $R^{10}$, and $R^{11}$ are hydrogen, $X^3$ is NH, $X^4$ is CH, and $X^5$ is O.

In another embodiment, $R^6$ is a sterically bulky group and $R^2$, $R^3$, $R^{3'}$, $R^4$, $R^{4'}$, $R^5$, $R^{5'}$, and $R^{6'}$ present are each hydrogen. In one embodiment, $R^6$ is tert-butyl and $R^2$, $R^3$, $R^{3'}$, $R^4$, $R^{4'}$, $R^5$, $R^{5'}$, and $R^{6'}$ present are each hydrogen. In another embodiment, $R^6$ is isopropyl and $R^2$, $R^3$, $R^{3'}$, $R^4$, $R^{4'}$, $R^5R^{5'}$, and $R^{6'}$ present are each hydrogen. In yet another embodiment, $R^6$ is selected from tert-butyl and isopropyl, and b=0. In yet another embodiment, $R^6$ is selected from tert-butyl and isopropyl, and c=0.

Steric hindrance may be introduced by choosing $R^5$ to be other than hydrogen. In one embodiment, a compound of formula (I) is represented by a compound of formula (Ie):

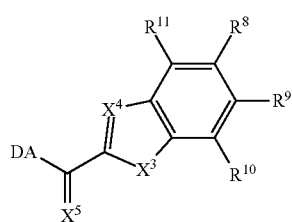

(Ie)

wherein DA is

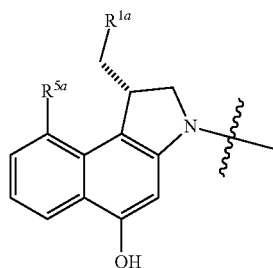

or by an isomer, or by a mixture of isomers, wherein $R^{1a}$ is selected from Cl and Br and $R^{5a}$ is selected from nitro, halogen, amino, hydroxy, and optionally substituted $C_{1-3}$ alkylamino, di($C_{1-3}$ alkyl)amino, $C_{1-6}$ alkylcarbonylamino, $C_{1-3}$ alkoxycarbonylamino, $C_{1-3}$ alkyloxy, $C_{1-3}$ alkylcarbonyloxy, $C_{1-3}$ alkylaminocarbonyloxy, or $C_{1-3}$ alkyl.

In a further embodiment, a compound of formula (I) is represented by a compound of formula (Ie) wherein DA is

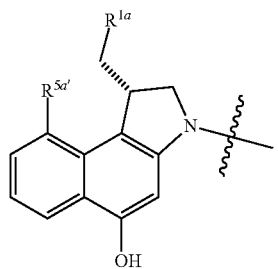

or by an isomer, or by a mixture of isomers, wherein $R^{1a}$ is selected from Cl and Br and $R^{5a'}$ is selected from methyl, ethyl, propyl, isopropyl, nitro, $CF_3$, F, Cl, Br, methoxy, amino, methylamino, formyl, hydroxymethyl, and dimethylamino.

In further embodiments, a compound of formula (I) is represented by a compound of formula (Ie) wherein DA is

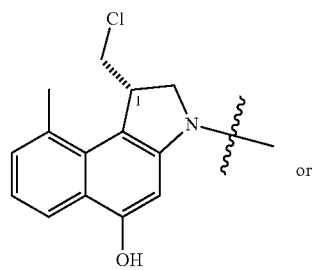

or

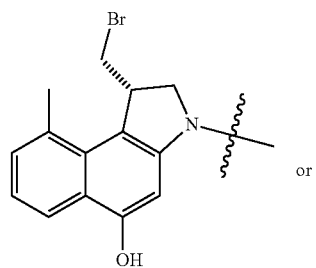

or

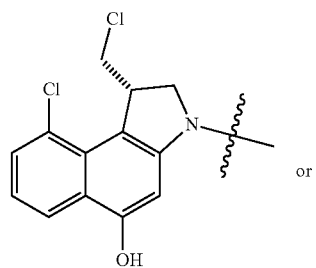

or

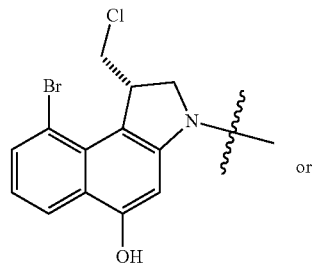

or

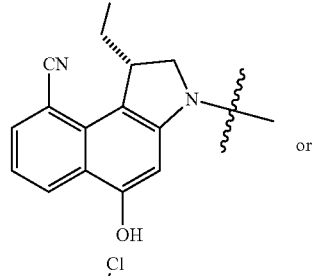

or

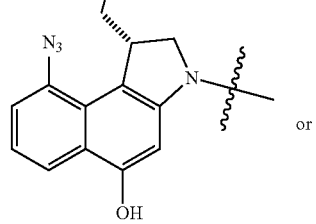

or

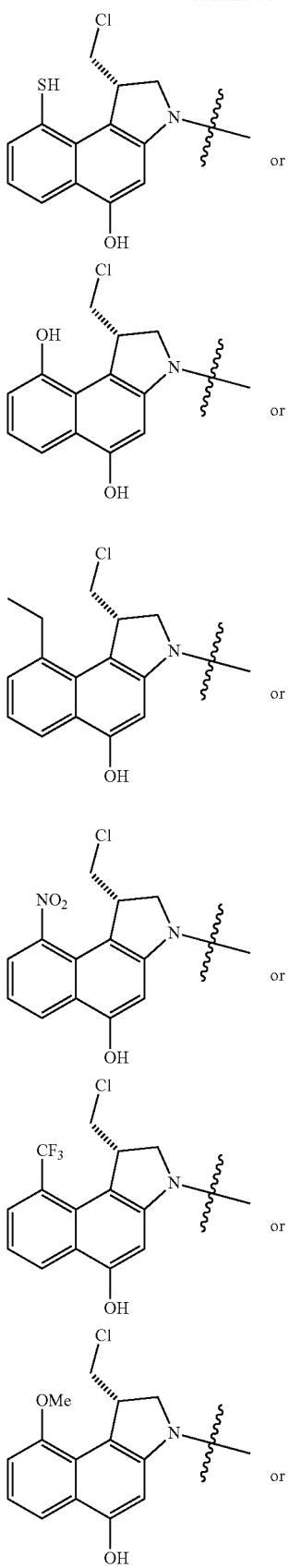
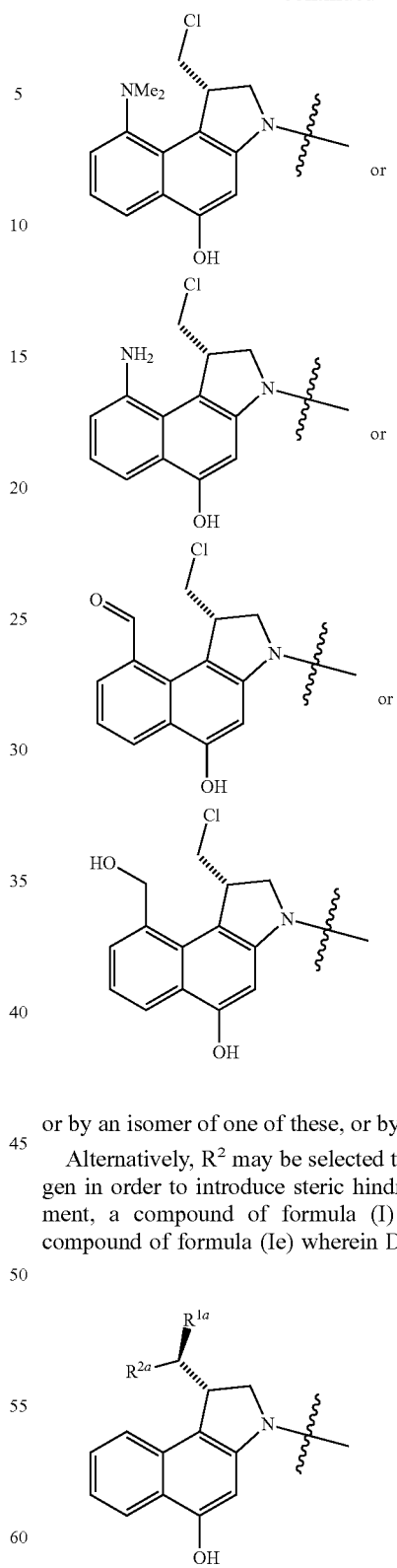

or by an isomer of one of these, or by a mixture of isomers.

Alternatively, $R^2$ may be selected to be other than hydrogen in order to introduce steric hindrance. In one embodiment, a compound of formula (I) is represented by a compound of formula (Ie) wherein DA is or by an isomer, or by a mixture of isomers, wherein $R^{1a}$ is selected from Cl and Br and $R^{2a}$ is selected from Cl and Br.

In further embodiments, a compound of formula (I) is represented by a compound of formula (Ie) wherein DA is

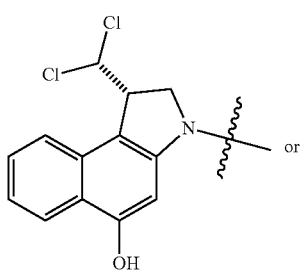

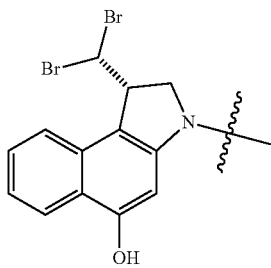

or by an isomer of one of these, or by a mixture of isomers.

Alternatively again, steric hindrance may also be created by choosing $R^6$ to be a relatively bulky substituent. In one embodiment, a compound of formula (I) is represented by a compound of formula (Ie) wherein DA is

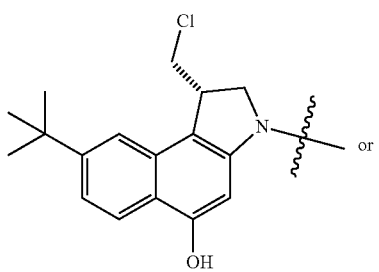

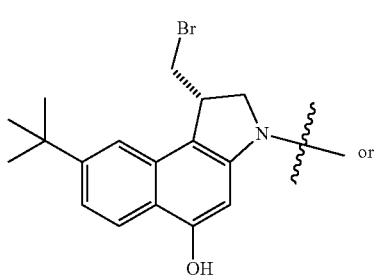

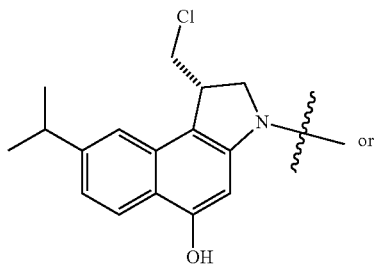

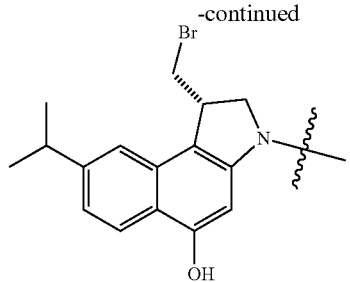

or by an isomer of one of these, or by a mixture of isomers.

More than one of $R^2$, $R^3$, $R^{3'}$, $R^4$, $R^{4'}$, $R^5$, $R^{5'}$, $R^6$, and $R^{6'}$ present may be other than hydrogen. For example, $R^2$ and $R^5$ may be selected to be other than hydrogen. Alternatively, $R^2$ and $R^6$, or $R^6$ and $R^5$, or $R^2$ and $R^4$, or $R^2$ and $R^{4'}$ may for example be selected to be other than hydrogen. All other combinations of two or more substituents from the group of $R^2$, $R^3$, $R^{3'}$, $R^4$, $R^{4'}$, $R^5$, $R^{5'}$, $R^6$, and $R^{6'}$ may be selected to be other than hydrogen as well.

In distinct embodiments, a compound of formula (I) is represented by a compound of formula (Ie) wherein DA is

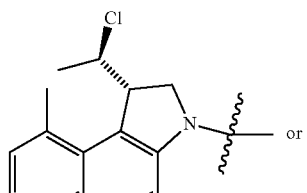

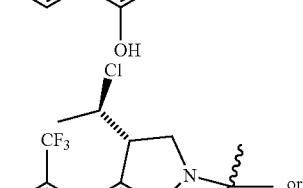

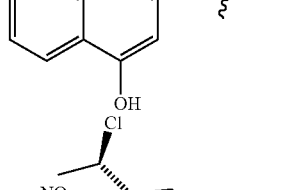

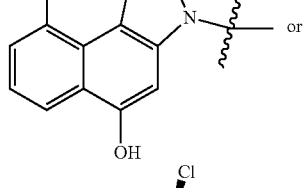

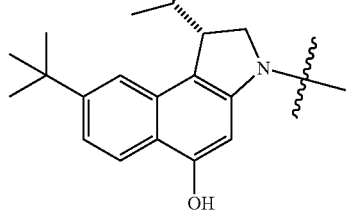

-continued

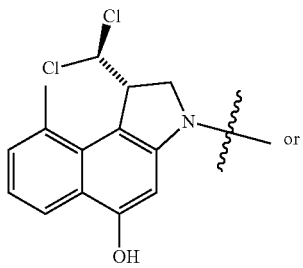
or

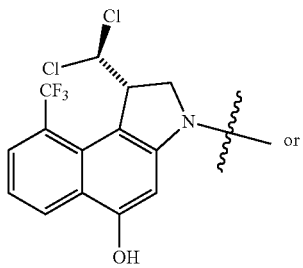
or

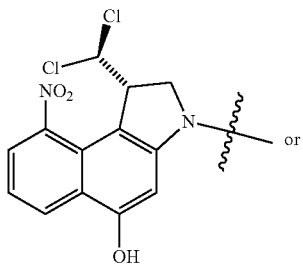
or

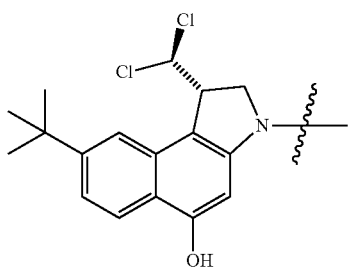

or by an isomer of one of these, or by a mixture of isomers.

In another aspect, this invention relates to a DNA alkylating compound that comprises the moiety

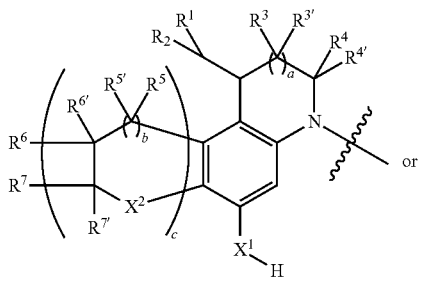

-continued

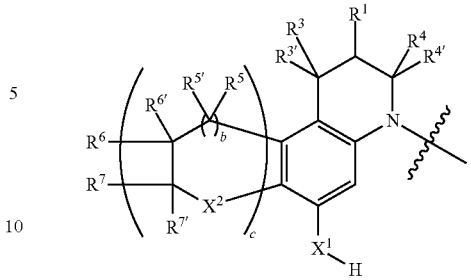

wherein $R^1$, $R^2$, $R^3$, $R^{3'}$, $R^4$, $R^{4'}$, $R^{5'}$, $R^6$, $R^{6'}$, $R^7$, $R^{7'}$, $X^1$, $X^2$, a, b, and c are as defined for a compound of formula (I) or (II) hereinabove, and wherein $R^5$ is selected from OH, SH, $NH_2$, $N_3$, $NO_2$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles.

The DNA-binding unit of compounds of formulae (I) and (II) is considered to assist in efficient binding of these compounds to DNA. It comprises one (hetero)aromatic structure or more (hetero)aromatic structures fused or coupled together. The heteroaromatic moiety can for example be an optionally substituted indole or benzofuran moiety. Such a moiety may be coupled to a DNA-alkylating moiety via, for instance, an amide bond. In one embodiment, $X^3$ is NH. In another embodiment, $X^3$ is O. In another embodiment, $X^4$ is CH. In another embodiment, $X^5$ is O. In another embodiment, $X^3$ is NH, $X^4$ is CH, and $X^5$ is O.

Substituents $R^8$, $R^9$, $R^{10}$, and $R^{11}$ may help improve the binding affinity of a compound of formula (I) or (II) for DNA. This may for example occur by selecting one of these substituents to be a (hetero)aromatic moiety. Thus, in one embodiment, $R^8$ is selected from

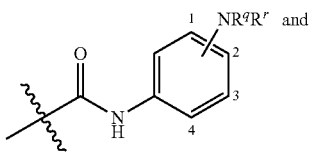

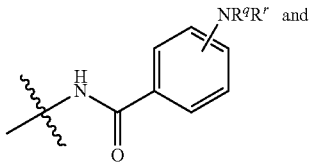

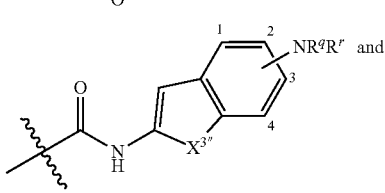

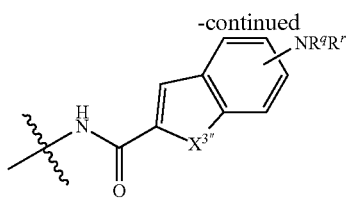

wherein $X^{3'''}$ is selected from O, S, and $NR^{15'}$, wherein $R^{15'}$ is selected from the same pool of substituents as $R^{15}$, $R^q$ and $R^r$ are selected from H and optionally substituted $C_{1-3}$ alkyl, and $NR^qR^r$ is connected to the phenyl ring through any one of carbon atoms 1-4. In another embodiment, $NR^qR^r$ is connected to the phenyl ring through carbon atom 2 or 4.

In another embodiment, $R^8$ is a substituent of the formula:

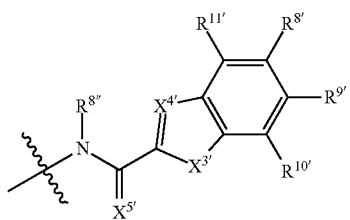

wherein $X^{3'}$, $X^{4'}$, $X^{5'}$, $R^{8'}$, $R^{9'}$, $R^{10'}$, and $R^{11'}$ are selected from the same pool of substituents as defined above for $X^3$, $X^4$, $X^5$, $R^8$, $R^9$, $R^{10}$, and $R^{11}$, respectively, and wherein $R^{8''}$ is selected from H and optionally substituted $C_{1-5}$ alkyl or $C_{1-5}$ heteroalkyl and optionally joined with $R^9$ or $R^{11}$ to form an optionally substituted heterocycle.

All embodiments for $R^8$, $R^9$, $R^{10}$, and $R^{11}$ specified in this document are also applicable to $R^{8'}$, $R^{9'}$, $R^{10'}$, and $R^{11'}$, respectively.

In one embodiment, $R^8$ or $R^{8'''}$ and $R^{11}$, and/or $R^{8'}$ and $R^{11'}$ are joined to form together with the linking atoms an optionally substituted dihydropyrrole moiety.

Substituents $R^8$, $R^9$, $R^{10}$, and $R^{11}$ may also assist in improving the pharmacokinetic properties of a compound of formula (I) or (II) or its conjugate, for example, its water solubility. This may for example occur by selecting one or more of the substituents $R^8$, $R^9$, $R^{10}$, and $R^{11}$ to comprise or be a water-soluble group. Furthermore, such a water-soluble group may prevent a compound of formula (I) or (II) from crossing a biological barrier, especially when it is an apolar barrier, such as a cell membrane. This may be advantageous, especially when a compound of formula (I) or (II) is delivered into a targeted cell through conjugation to a targeting moiety before it is released from the conjugate. When a compound of formula (I) or (II) is prematurely released from the conjugate, e.g., in the circulation, it may be unable or only moderately able to enter (non-targeted) cells aspecifically as its membrane translocation capabilities may be impaired. This may lead to increased selectivity and therefore to fewer side effects. In addition, at least in some instances, for example when the water-soluble group is positively charged under physiological conditions, the water-soluble group may also improve the binding affinity for DNA by means of favorable electrostatic interactions.

A water-soluble group is a group that imparts increased solubility on a compound of formula (I) or (II) and/or a conjugate thereof. In one embodiment, water solubility of a compound of this invention carrying a water-soluble group is increased by more than 100% compared to the compound lacking said water-soluble group. In other embodiments, water solubility of a compound of this invention carrying a water-soluble group is increased by more than 75% or 50% or 25% or 10% compared to the compound lacking said water-soluble group. The water-soluble group may also contribute to prevent or reduce aggregation of compounds of this invention or to reduce side effects. Examples of water-soluble groups include, but are not limited to, $-NH_2$, $-NH-$, $-NHR^s$, $-NR^s-$, $-N(R^s)(R^t)$, $-^+N(R^s)(R^t)-$, $-^+N(R^s)(R^t)(R^u)$, $-COOH$, $-OP(O)(OH)_2$, $-OP(O)(OH)O-$, $-OP(O)(OR^s)O-$, $-OP(O)(OH)OR^s)$, $-OP(O)(OR^s)OR^t$, $-P(O)(OH)_2$, $-P(O)(OH)O-$, $-P(O)(OR^s)OH$, $-P(O)(OR^s)O-$, $-P(O)(OR^s)(OR^t)$, $-OS(O)_2OH$, $-OS(O)_2O-$, $-OS(O)_2OR^s$, $-S(O)_2OH$, $-S(O)_2O-$, $-S(O)_2OR^s$, $-OS(O)OH$, $-OS(O)O-$, $-OS(O)OR^s$, $-S(O)OH$, $-S(O)O-$, $-OS(O)-$, $-S(O)OR^s$, $-OS(O)_2-$, $-OS(O)_2R^s$, $-S(O)_2-$, $-S(O)_2R^s$, $-OS(O)R^s$, $-S(O)-$, $-S(O)R^s$, $-(OCH_2CH_2)_{v'}OH$, $-(OCH_2CH_2)_{v'}O-$, $-(OCH_2CH_2)_{v'}OR^s$, a sugar moiety, an oligosaccharide moiety, and an oligopeptide moiety, or a protonated or deprotonated form thereof and further any combination thereof, wherein $R^s$, $R^t$, and $R^u$ are independently selected from H and optionally substituted $C_{1-3}$ alkyl, two or more of $R^s$, $R^t$, and $R^u$ optionally being joined by one or more bonds to form one or more carbocycles and/or heterocycles, and v' is an integer selected from 1 to 100. The water-soluble group may be at any position within $R^8$, $R^9$, $R^{10}$, and/or $R^{11}$ or may constitute the whole $R^8$, $R^9$, $R^{10}$, or $R^{11}$ moiety. The water-soluble group may for example be located at any interior position, be part of the main chain, be part of a ring structure, be a functional group pending to the main chain or a ring, or be placed at the position at which the $R^8$, $R^9$, $R^{10}$, or $R^{11}$ substituent is attached to the remainder of the agent.

In one embodiment, none of $R^8$, $R^9$, $R^{10}$, and $R^{11}$ contains a water-soluble group.

In another embodiment, at least one of $R^8$, $R^9$, $R^{10}$, and $R^{11}$ contains a water-soluble group.

In another embodiment, at least one of $R^8$, $R^9$, and $R^{10}$ contains a water-soluble group.

In yet another embodiment, $R^8$ contains a water-soluble group.

In yet another embodiment, $R^9$ contains a water-soluble group.

In yet another embodiment, $R^{10}$ contains a water-soluble group.

In one embodiment, the water-soluble group is a carboxylic acid group.

In another embodiment, the water-soluble group is an amino group.

In a further embodiment, the water-soluble group is a primary amino group.

In another embodiment, the water-soluble group is a secondary amino group.

In another embodiment, the water-soluble group is a tertiary amino group.

In another embodiment, the water-soluble group is a quaternary amino (ammonium) group.

In other embodiments, the water-soluble group is a primary or secondary or tertiary or quaternary aliphatic amino group.

In other embodiments, the water-soluble group is a dimethylamino group or a methylamino group or an amino ($NH_2$) group.

In another embodiment, the water-soluble group is an N-methyl-N-(carboxymethyl)amino group.

In yet another embodiment, the water-soluble group is an N-methyl-N-(2-methoxy-2-oxoethyl)amino group.

In another embodiment, at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, $R^{17}$, and $R^{18}$ contains or is the moiety COOH.

In another embodiment, at least one of the substituents $R^8$, $R^9$, and $R^{10}$ contains or is the moiety COOH and there is at least another water-soluble group present in $R^8$, $R^9$, or $R^{10}$.

In another embodiment, at least one of the water-soluble groups in $R^8$, $R^9$, and $R^{10}$ is an aliphatic secondary, tertiary, or quaternary amine moiety not being conjugated to an aromatic moiety or a carbonyl group.

In yet another embodiment, at least one of the water-soluble groups in $R^8$, $R^9$, $R^{10}$, and $R^{11}$ is an aliphatic secondary amine moiety not being conjugated to an aromatic moiety or a carbonyl group and at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, $R^{17}$, and $R^{18}$ contains or is the moiety COOH.

In yet another embodiment, at least one of the water-soluble groups in $R^8$, $R^9$, and $R^{10}$ is an aliphatic secondary amine moiety not being conjugated to an aromatic moiety or a carbonyl group and at least one of the substituents $R^8$, $R^9$, and $R^{10}$ contains or is the moiety COOH.

In yet another embodiment at least one of the substituents $R^8$, $R^9$, and $R^{10}$ contains a COOH moiety and an aliphatic secondary amine moiety not being conjugated to an aromatic moiety or a carbonyl group.

In one embodiment, $R^8$, $R^9$, or $R^{10}$ is selected from —O—$C_{1-6}$ alkylene-N($R^{100}$)$_2$, —N($R^{100}$)C(O)—$C_{1-5}$ alkylene-N($R^{100}$)$_2$, (1-($R^{100}$)piperidin-4-yl)-$C_{1-5}$ is alkylene-O—, (morpholin-4-yl)-$C_{1-8}$ alkylene-O—, —C(O)N($R^{100}$)—$C_{1-6}$ alkylene-N($R^{100}$)$_2$, and —CO$_2$$R^{100}$, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^8$ is selected from —O—$C_{1-6}$ alkylene-N($R^{100}$)$_2$, —N($R^{100}$)C(O)—$C_{1-5}$ alkylene-N($R^{100}$)$_2$, (1-($R^{100}$)piperidin-4-yl)-$C_{1-5}$ alkylene-O—, (morpholin-4-yl)-$C_{1-8}$ alkylene-O—, —C(O)N($R^{100}$)—$C_{1-6}$ alkylene-N($R^{100}$)$_2$, and —CO$_2$$R^{100}$, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^9$ is selected from —O—$C_{1-6}$ alkylene-N($R^{100}$)$_2$, —N($R^{100}$)C(O)—$C_{1-5}$ alkylene-N($R^{100}$)$_2$, (1-($R^{100}$)piperidin-4-yl)-$C_{1-5}$ alkylene-O—, (morpholin-4-yl)-$C_{1-8}$ alkylene-O—, —C(O)N($R^{100}$)—$C_{1-6}$ alkylene-N($R^{100}$)$_2$, and —CO$_2$$R^{100}$, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^{10}$ is selected from —O—$C_{1-6}$ alkylene-N($R^{100}$)$_2$, —N($R^{100}$)C(O)—$C_{1-5}$ alkylene-N($R^{100}$)$_2$, (1-($R^{100}$)piperidin-4-yl)-$C_{1-5}$ alkylene-O—, (morpholin-4-yl)-$C_{1-8}$ alkylene-O—, —C(O)N($R^{100}$)—$C_{1-6}$ alkylene-N($R^{100}$)$_2$, and —CO$_2$$R^{100}$, wherein each $R^{100}$ is independently selected from H and $C_{1-3}$ alkyl, the latter being optionally substituted with COOH or COOR$^{300}$, $R^{300}$ being $C_{1-4}$ alkyl.

In one embodiment, $R^8$, $R^9$, or $R^{10}$ is selected from

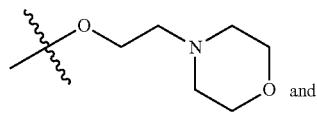
and

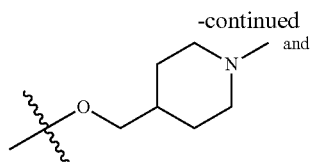
and

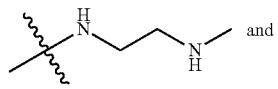
and

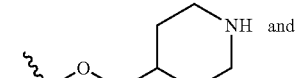
and

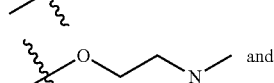
and

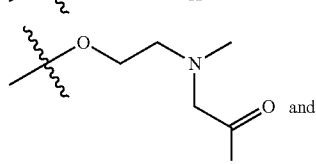
and

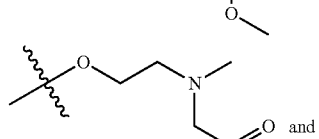
and

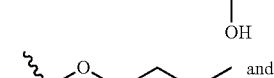
and

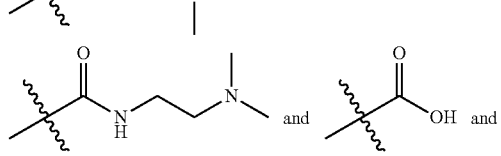
and

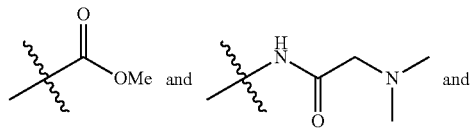
and

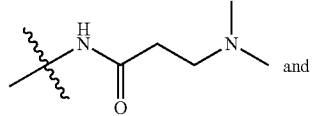

In another embodiment, $R^8$ is selected from

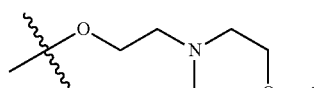
and

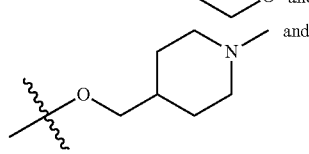
and

-continued
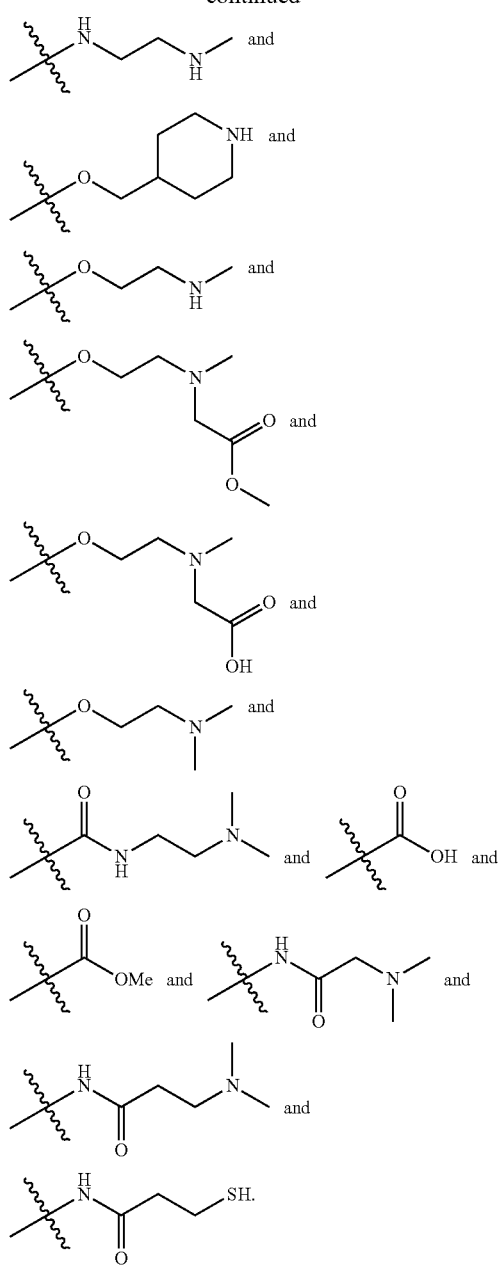
In yet another embodiment, $R^9$ is selected from
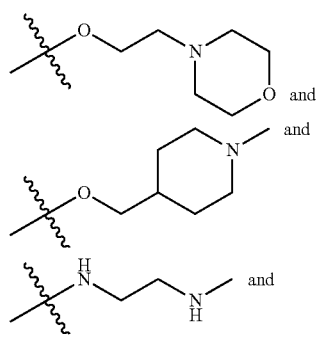
-continued
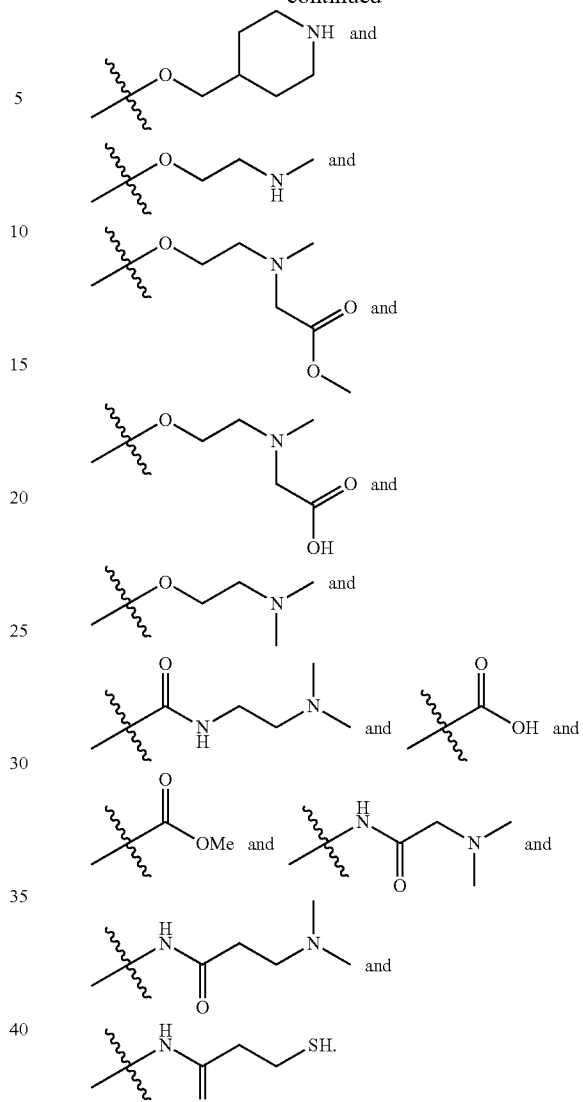
In another embodiment, $R^8$ is selected from
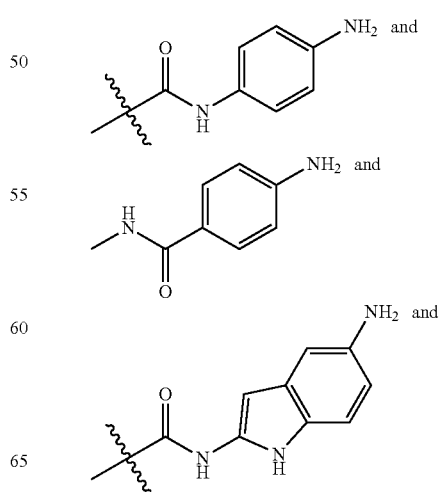

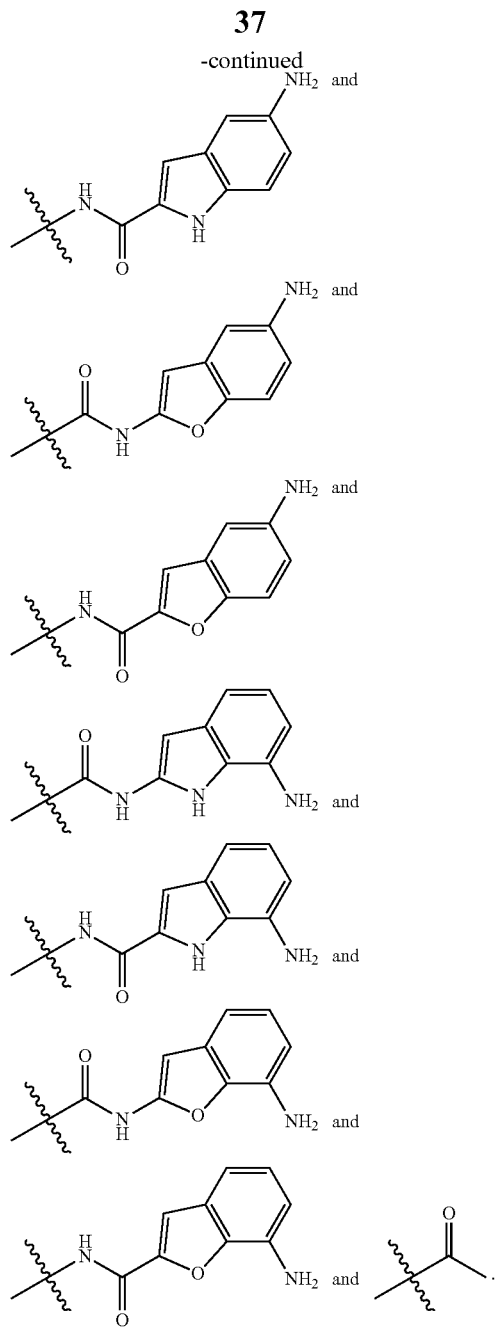

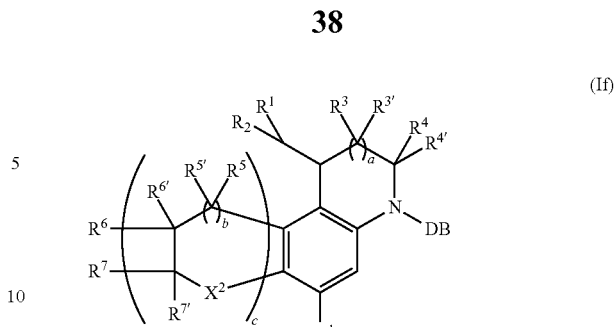

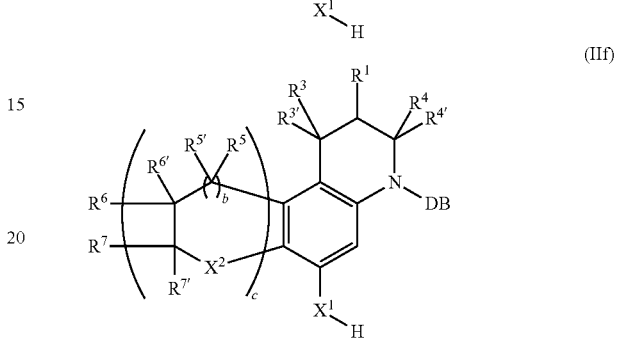

wherein DB is

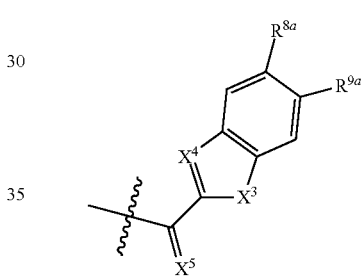

wherein $X^3$, $X^4$, and $X^5$ are as defined hereinabove, $R^{8a}$ is selected from —O—$C_{1-5}$ alkylene-N($R^{100}$)$_2$, —N($R^{100}$)C(O)—$C_{1-5}$ alkylene-N($R^{100}$)$_2$, (1-($R^{100}$)piperidin-4-yl)-$C_{1-5}$ alkylene-O—, (morpholin-4-yl)—$C_{1-8}$ alkylene-O—, —C(O)N($R^{100}$)—$C_{1-6}$ alkylene-N($R^{100}$)$_2$, and —CO$_2$R$^{100}$, wherein each $R^{100}$ is independently selected from H and $C_{1-3}$ alkyl, the latter being optionally substituted with COOH or COOR$^{300}$, $R^{300}$ being $C_{1-4}$ alkyl, and $R^{9a}$ is selected from H, $C_{1-3}$ alkyloxy, $C_{1-3}$ alkylcarbonyl. In another embodiment of this invention, a compound of formula (I) and (II) is represented by a compound of formula (If) and (IIf), respectively, wherein DB is

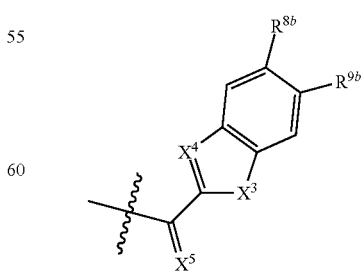

wherein $X^3$, $X^4$, and $X^5$ are as defined hereinabove, $R^{9b}$ is selected from —O—$C_{1-6}$ alkylene-N($R^{100}$)$_2$, —N($R^{100}$)C Either none or one or more of $R^8$, $R^9$, $R^{10}$, and $R^{11}$ may be selected to be other than hydrogen. For example, one of $R^8$, $R^9$, $R^{10}$, and $R^{11}$ may be other than hydrogen. In one embodiment, $R^8$ is other than hydrogen and $R^9$, $R^{10}$, and $R^{11}$ are hydrogen. In another embodiment, $R^9$ is other than hydrogen and $R^8$, $R^{10}$, and $R^{11}$ are hydrogen. Alternatively, two of $R^8$, $R^9$, $R^{10}$, and $R^{11}$ may be other than hydrogen. In one embodiment, $R^8$ and $R^9$ are other than hydrogen and $R^{10}$ and $R^{11}$ are hydrogen. In another embodiment, $R^8$ and $R^{10}$ are other than hydrogen and $R^9$ and $R^{11}$ are hydrogen. As another alternative, three of $R^8$, $R^9$, $R^{10}$, and $R^{11}$ are other than hydrogen. In one embodiment, $R^8$, $R^9$, and $R^{10}$ are other than hydrogen and $R^1$ is hydrogen.

In one embodiment of this invention, a compound of formula (I) or (II) is represented by a compound of formula (If) or (IIf), respectively:

(O)—C$_{1-5}$ alkylene-N(R$^{100}$)$_2$, (1-(R$^{100}$)piperidin-4-yl)-C$_{1-5}$ alkylene-O—, (morpholin-4-yl)-C$_{1-8}$ alkylene-O—, —C(O)N(R$^{100}$)—C$_{1-6}$ alkylene-N(R$^{100}$)$_2$, and —CO$_2$R$^{100}$, wherein each R$^{100}$ is independently selected from H and C$_{1-3}$ alkyl, the latter being optionally substituted with COOH or COOR$^{300}$, R$^{300}$ being C$_{1-4}$ alkyl, and R$^{8b}$ is selected from H, C$_{1-3}$ alkyloxy, and C$_{1-3}$ alkylcarbonyl.

In another embodiment of this invention, a compound of formula (I) or (II) is represented by a compound of formula (If) or (IIf), respectively, wherein DB is

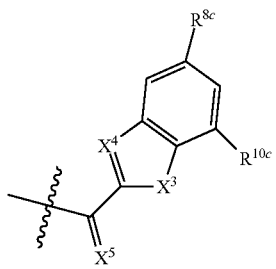

wherein X$^3$, X$^4$, and X$^5$ are as defined hereinabove, R$^{8c}$ is selected from —O—C$_{1-6}$ alkylene-N(R$^{100}$)$_2$, —N(R$^{100}$)C(O)—C$_{1-5}$ alkylene-N(R$^{100}$)$_2$, (1-(R$^{100}$)piperidin-4-yl)-C$_{1-5}$ alkylene-O—, (morpholin-4-yl)-C$_{1-8}$ alkylene-O—, —C(O)N(R$^{100}$)—C$_{1-6}$ alkylene-N(R$^{100}$)$_2$, and —CO$_2$R$^{100}$, wherein each R$^{100}$ is independently selected from H and C$_{1-3}$ alkyl, the latter being optionally substituted with COOH or COOR$^{300}$, R$^{300}$ being C$_{1-4}$ alkyl, and R$^{10c}$ is selected from H, C$_{1-3}$ alkyloxy, and C$_{1-3}$ alkylcarbonyl.

In another embodiment of this invention, a compound of formula (I) or (II) is represented by a compound of formula (If) or (IIf), respectively, wherein DB is

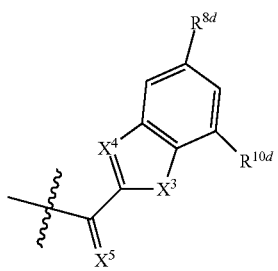

wherein X$^3$, X$^4$, and X$^5$ are as defined hereinabove, R$^{10d}$ is selected from —O—C$_1$ . . . alkylene-N(R$^{100}$)$_2$, —N(R$^{100}$)C(O)—C$_{1-5}$ alkylene-N(R$^{100}$)$_2$, (1-(R$^\Phi$)piperidin-4-yl)-C$_{1-5}$ alkylene-O—, (morpholin-4-yl)-C$_{1-8}$ alkylene-O—, —C(O)N(R$^{100}$)—C$_{1-6}$, alkylene-N(R$^{100}$)$_2$, and —CO$_2$R$^{100}$, wherein each R$^{100}$ is independently selected from H and C$_{1-3}$ alkyl, the latter being optionally substituted with COOH or COOR$^{300}$, R$^{300}$ being C$_{1-4}$ alkyl, and R$^{8d}$ is selected from H, C$_{1-3}$ alkyloxy, and C$_{1-3}$ alkylcarbonyl.

In distinct embodiments, a compound of formula (I) or (II) is represented by a compound of formula (If) or (IIf), respectively, wherein DB is

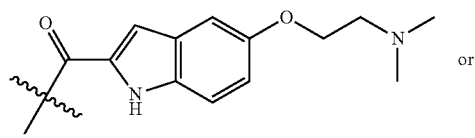

or

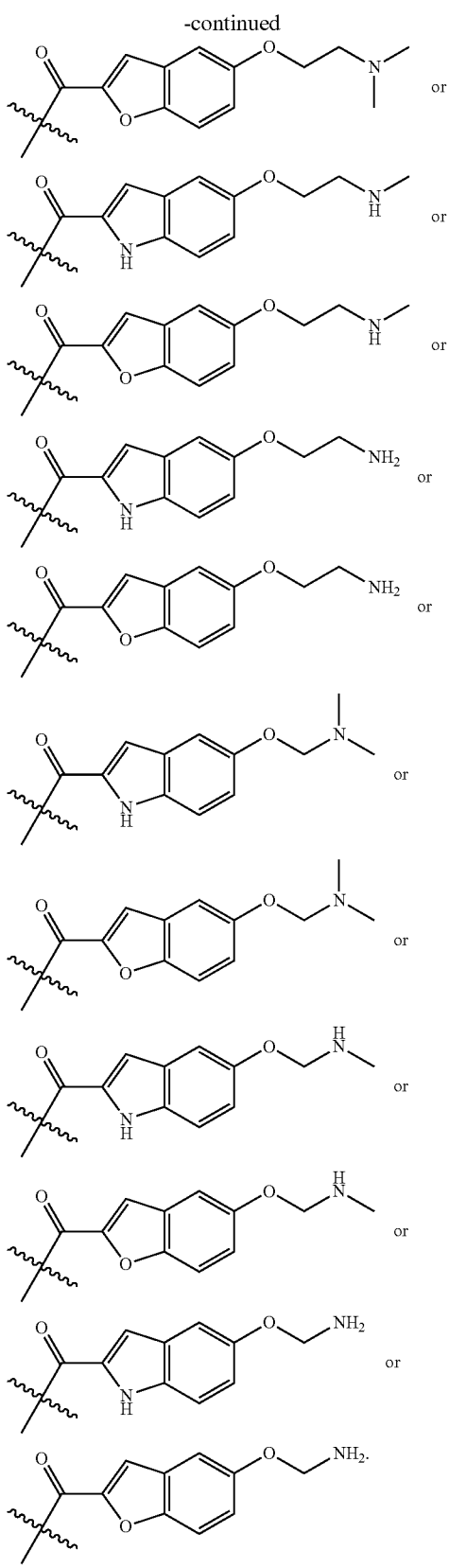

In other distinct embodiments, a compound of formula (I) or (II) is represented by a compound of formula (If) or (IIf), respectively, wherein DB is

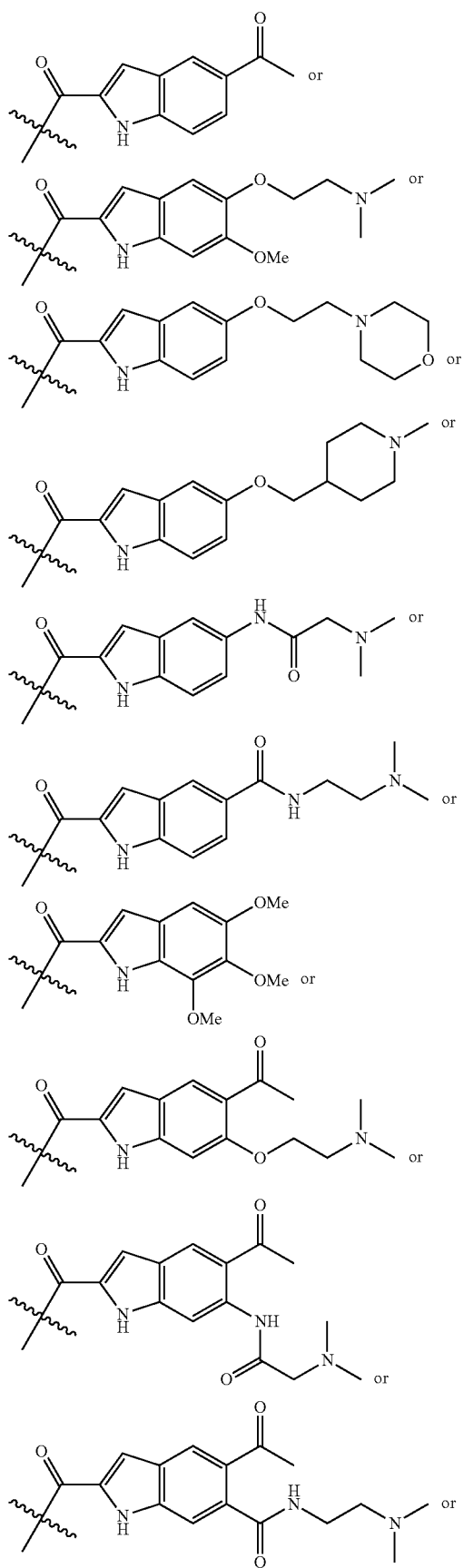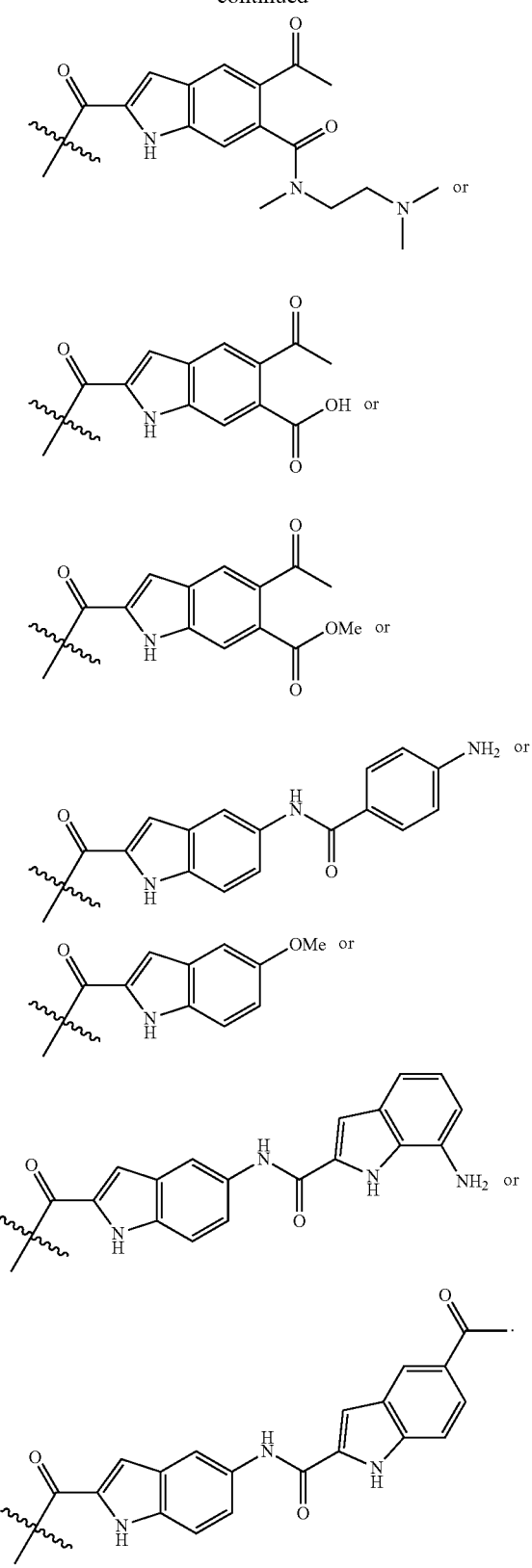
In other distinct embodiments, a compound of formula (I) or (II) is represented by a compound of formula (If) or (IIf), respectively, wherein DB is

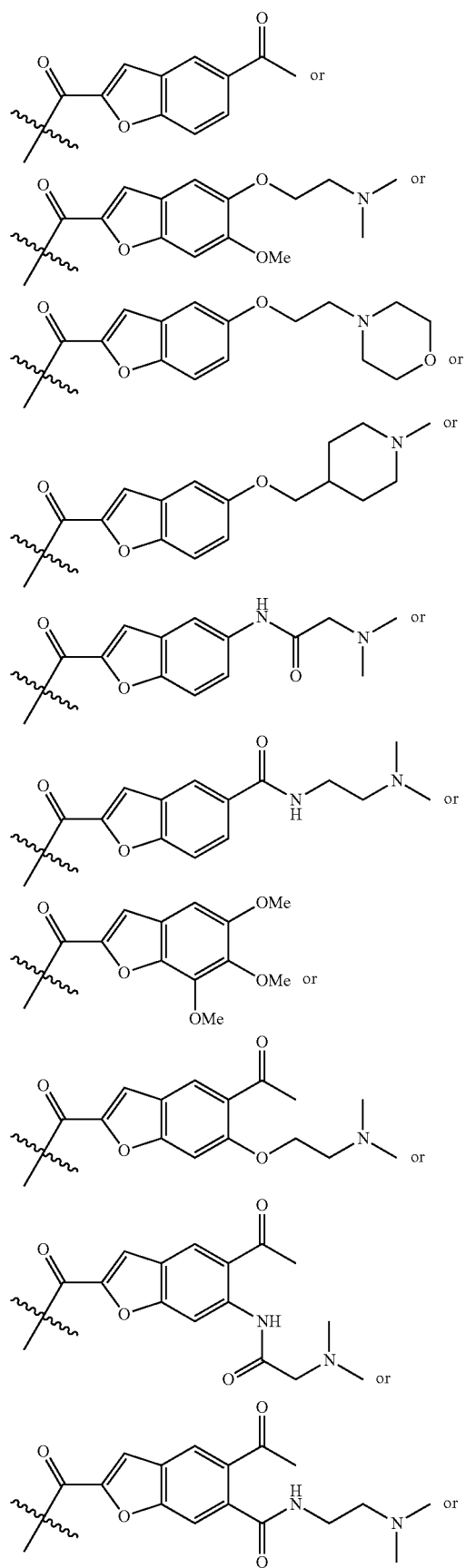
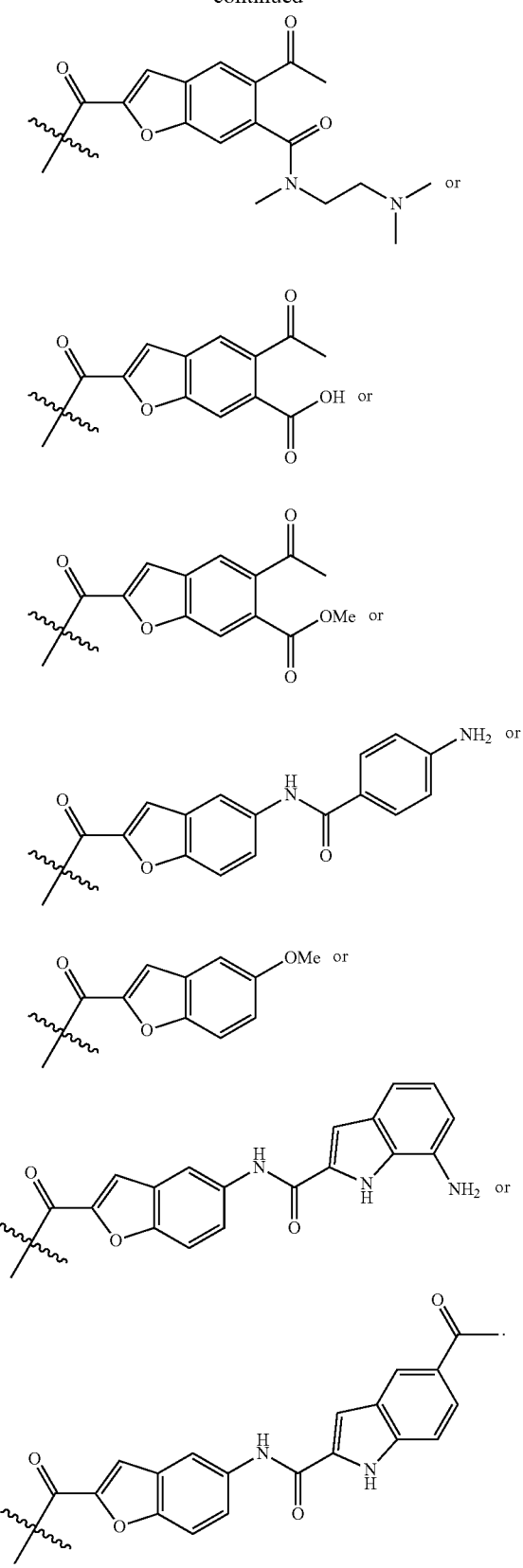
In distinct embodiments, a compound of formula (I) is represented by

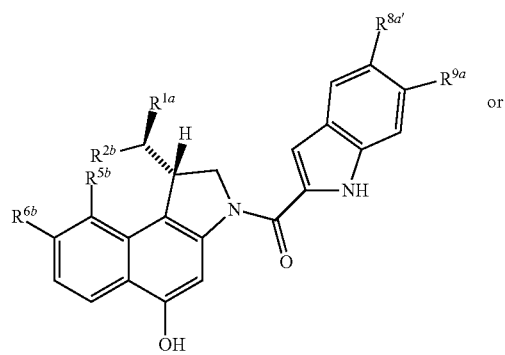

or

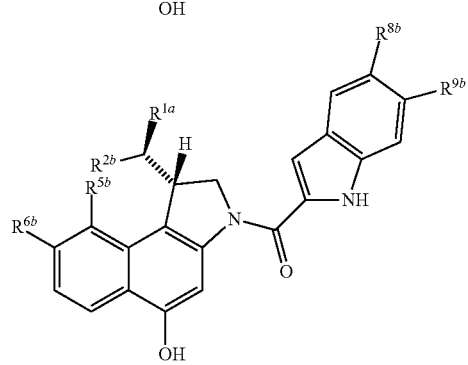

or

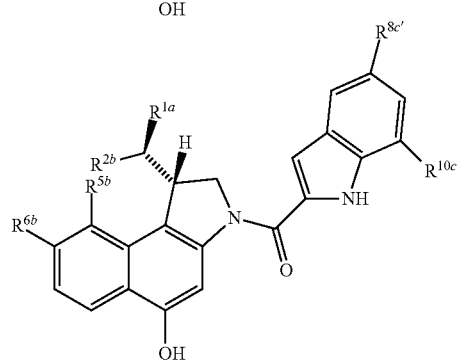

or

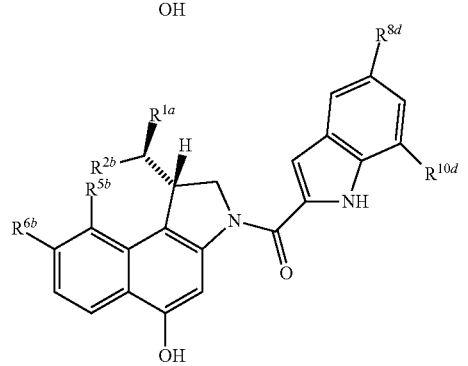

or by an isomer of one of these, or by a mixture of isomers, wherein $R^{5b}$ is selected from the same pool as $R^{5a'}$, except that it may be selected to be hydrogen as well, $R^{6b}$ is selected from hydrogen, tert-butyl, and isopropyl, $R^{2b}$ is selected from the same pool as $R^2$, except that it may not be methyl when $R^{5b}$ and $R^{6b}$ are both hydrogen, $R^{1a}$, $R^{8b}$, $R^{8d}$, $R^{9a}$, $R^{9b}$, $R^{10c}$, and $R^{10d}$ are as defined above, and $R^{8a'}$ and $R^{8c'}$ are selected from the same pools of substituents as $R^{8a}$ and $R^{8c}$, respectively, except that $R^{8a'}$ and $R^{8c'}$ may not be N,N-dimethylaminoethoxy when $R^{9a}$ or $R^{10c}$ is H, $R^{5b}$ is methyl, $R^{1a}$ is chloride, and $R^{2b}$ and $R^{6b}$ are both hydrogen.

In distinct embodiments, a compound of formula (I) is represented by

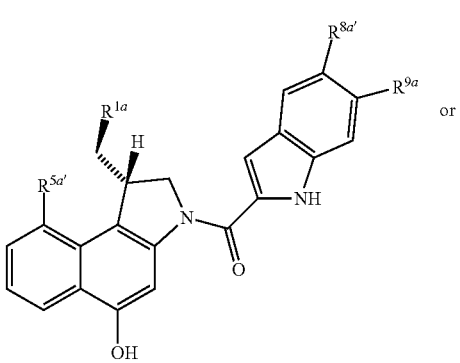

or

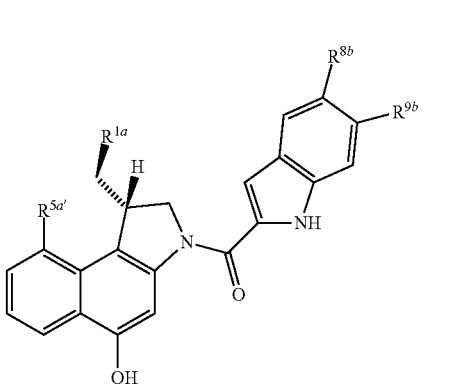

or

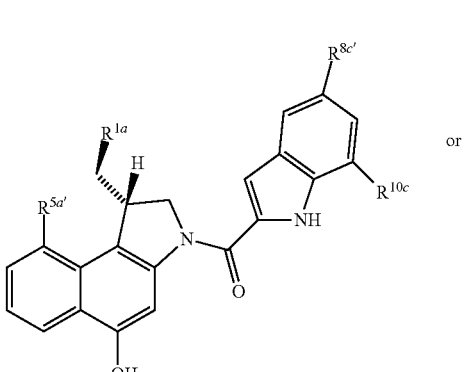

or

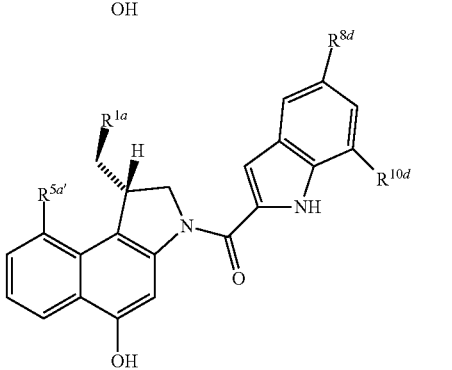

or by an isomer of one of these, or by a mixture of isomers, wherein $R^{1a}$, $R^{5a'}$, $R^{8b}$, $R^{8d}$, $R^{9a}$, $R^{9b}$, $R^{10c}$, and $R^{10d}$ are as defined above and $R^{8a'}$ is selected from the same pool of substituents as $R^{8a}$ except that $R^{8a'}$ and $R^{8c'}$ may not be N,N-dimethylaminoethoxy when $R^{9a}$ or $R^{10c}$ is H, $R^{1a}$ is chloride, and $R^{5a'}$ is methyl.

In other distinct embodiments, a compound of formula (I) is represented by

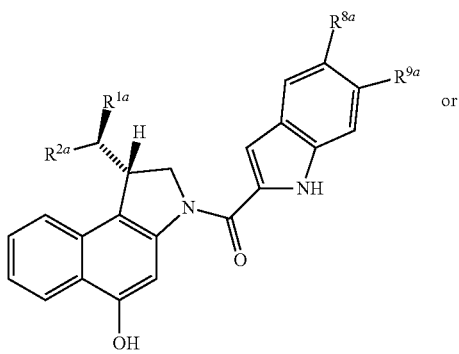

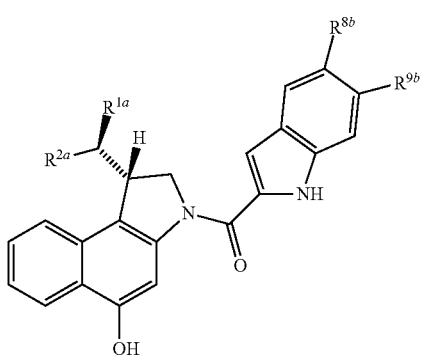

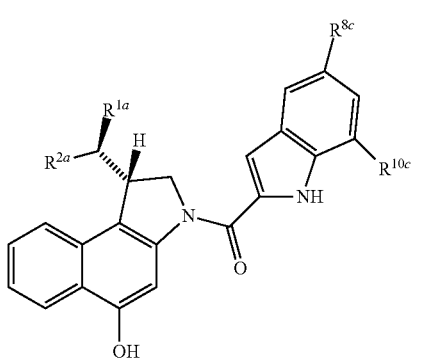

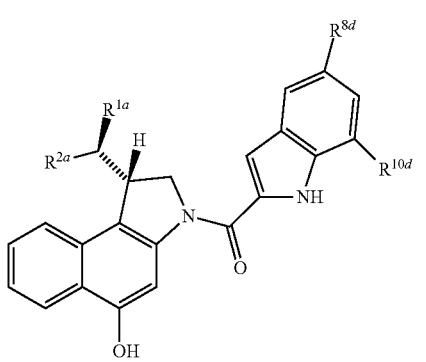

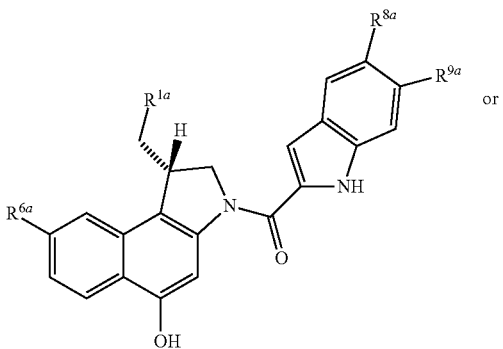

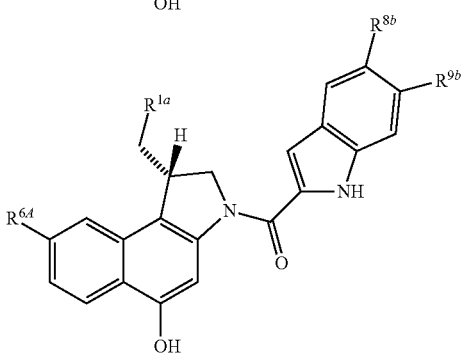

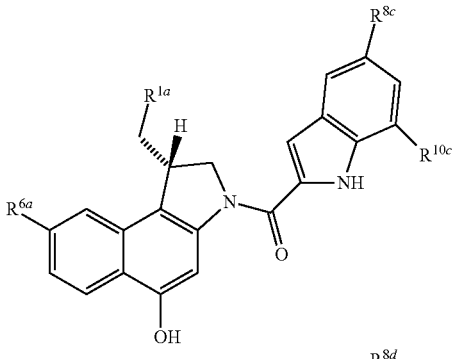

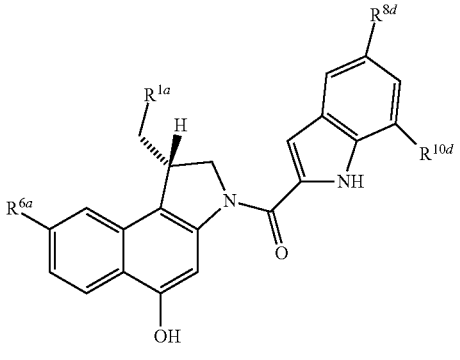

or by an isomer of one of these, or by a mixture of isomers, wherein $R^{1a}$, $R^{2a}$, $R^{8a}$, $R^{8b}$, $R^{8c}$, $R^{8d}$, $R^{9a}$, $R^{9b}$, $R^{10c}$, and $R^{10d}$ are as defined above.

In other distinct embodiments, a compound of formula (I) is represented by or by an isomer of one of these, or by a mixture of isomers, wherein $R^{1a}$, $R^{8a}$, $R^{8b}$, $R^{8c}$, $R^{8d}$, $R^{9a}$, $R^{9b}$, $R^{10c}$, and $R^{10d}$ are as defined above and $R^{6a}$ is selected from tert-butyl and isopropyl.

In one embodiment, this invention relates to a compound of formula (I) or (II) wherein $R^2$ is selected from $CF_3$, CN, $C(O)NH_2$, C(O)H, C(O)OH, $C(O)R^a$, $C(O)OR^a$, and $C(O)N(R^a)R^{a'}$, wherein $R^a$ and $R^{a'}$ are independently selected from H and optionally substituted $C_{1-3}$ alkyl or $C_{1-3}$ heteroalkyl, $R^3$, $R^{3'}$, $R^4$, and $R^{4'}$ are independently selected from hydrogen and optionally substituted $C_{1-3}$ alkyl, $R^1$ is selected from halogen and $OSO_2R^o$, and at least one of $R^8$, $R^9$, $R^{10}$, and $R^{11}$ comprises at least one water-soluble group.

In one embodiment, this invention relates to a compound of formula (Ib) or (IIb) wherein $R^2$ is selected from $CF_3$, CN, $C(O)NH_2$, $C(O)H$, $C(O)OH$, $C(O)R^a$, $C(O)OR^a$, and $C(O)N(R^a)R^{a'}$, wherein $R^a$ and $R^{a'}$ are independently selected from H and optionally substituted $C_{1-3}$ alkyl or $C_{1-3}$ heteroalkyl; $X^2$ is $CR^{14}$; $R^3$, $R^{3'}$, $R^4$, and $R^{4'}$ are independently selected from hydrogen and optionally substituted $C_{1-3}$ alkyl; $R^1$ is selected from halogen and $OSO_2R^o$, provided that at least one of $R^8$, $R^9$, $R^{10}$, and $R^{11}$ comprises at least one water-soluble group.

In another embodiment, this invention relates to a compound of formula (I) or (II) wherein $R^2$ is selected from $N_3$, $NO_2$, NO, halogen, $SR^b$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^b$, $N(R^b)R^c$, $^+N(R^b)(R^c)R^d$, $P(O)(OR^a)(OR^{a'})$, $OP(O)(OR^a)(OR^{a'})$, $SiR^aR^{a'}R^{a''}$, $OC(O)R^a$, $OC(O)OR^a$, $OC(O)N(R^a)R^{a'}$, $N(R^a)C(O)R^{a'}$, $N(R^a)C(O)OR^{a'}$, and $N(R^a)C(O)N(R^{a'})R^{a''}$, wherein $R^a$, $R^{a'}$, and $R^{a''}$ are independently selected from H and optionally substituted $C_{1-3}$ alkyl or $C_{1-3}$ heteroalkyl, and $R^b$, $R^c$, and $R^d$ are independently selected from optionally substituted $C_{1-3}$ alkyl and $C_{1-3}$ heteroalkyl.

In another embodiment, this invention relates to a compound of formula (Ib) or (IIb) wherein $R^2$ is selected from $N_3$, $NO_2$, NO, halogen, $SR^b$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^b$, $N(R^b)R^c$, $^+N(R^b)(R^c)R^d$, $P(O)(OR^a)(OR^{a'})$, $OP(O)(OR^a)(OR^{a'})$, $SiR^aR^{a'}R^{a''}$, $OC(O)R^a$, $OC(O)OR^a$, $OC(O)N(R^a)R^{a'}$, $N(R^a)C(O)R^{a'}$, $N(R^a)C(O)OR^{a'}$, and $N(R^a)C(O)N(R^{a'})R^{a''}$, wherein $R^a$, $R^{a'}$, and $R^{a''}$ are independently selected from H and optionally substituted $C_{1-3}$ alkyl or $C_{1-3}$ heteroalkyl, and $R^b$, $R^c$, and $R^d$ are independently selected from optionally substituted $C_{1-3}$ alkyl and $C_{1-3}$ heteroalkyl, and $X^2$ is $CR^{14}$.

In another embodiment, this invention relates to a compound of formula (I) or (II) wherein $R^2$, $R^3$, $R^{3'}$, $R^4$, and $R^{4'}$ are H, $R^5$ and $R^{5'}$ are independently selected from OH, SH, $NH_2$, $N_3$, $NO_2$, NO, halogen, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $OC(O)R^e$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles, and $R^{5'}$ may in addition be absent; $R^1$ is selected from halogen and $OSO_2R^o$; $X^4$ is CH; $X^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, $OR^h$, and $O(CH_2)_{bb}N(R^{101})(R^{101})$, wherein $R^{101}$ and $R^{102}$ are independently H or unsubstituted $C_{1-3}$ alkyl, bb is an integer from 1 to 20, and $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group.

In another embodiment, this invention relates to a compound of formula (Ib) wherein $R^2$, $R^4$, and $R^{4'}$ are H, $R^5$ is selected from OH, SH, $NH_2$, $N_3$, $NO_2$, NO, halogen, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $OC(O)R^e$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles; $X^2$ is $CR^{14}$; $R^1$ is selected from halogen and $OSO_2R^o$; $X^4$ is CH; a is 0; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, $OR^h$, and $O(CH_2)_{bb}N(R^{100})(R^{102})$, wherein $R^{101}$ and $R^{102}$ are independently H or unsubstituted $C_{1-3}$ alkyl, bb is an integer from 1 to 20, and $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group.

In another embodiment, this invention relates to a compound of formula (I) or (II) wherein $R^2$, $R^3$, $R^{3'}$, $R^4$, and $R^{4'}$ are H, $R^5$ and $R^{5'}$ are independently selected from OH, SH, $NH_2$, $N_3$, $NO_2$, NO, halogen, $SR^e$, $S(O)R^e$, $S(O)_2R^e$, $S(O)OR^e$, $S(O)_2OR$, $OS(O)R^e$, $OS(O)_2R^e$, $OS(O)OR$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $OC(O)R^e$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles, and $R^{5'}$ may in addition be absent; $R^1$ is selected from halogen and $OSO_2R^o$; $X^4$ is CH; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, $OR^b$, and $O(CH_2)_{bb}N(R^{101})(R^{102})$, wherein $R^{101}$ and $R^{102}$ are independently H or unsubstituted $C_{1-3}$ alkyl, bb is an integer from 1 to 20, and $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group.

In another embodiment, this invention relates to a compound of formula (Ib) wherein $R^2$, $R^4$, and $R^{4'}$ are H, $R^5$ is selected from OH, SH, $NH_2$, $N_3$, $NO_2$, NO, halogen, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $OC(O)R^e$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^e$, $R^f$, and $R^g$ optionally being joined by one or more bonds to form one or more optionally substituted carbocycles and/or heterocycles; $R^1$ is selected from halogen and $OSO_2R^o$; $X^4$ is CH; $X^2$ is $CR^{14}$; a is 0; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, $OR^h$, and $O(CH_2)_{bb}N(R^{101})(R^{102})$, wherein $R^{101}$ and $R^{102}$ are independently H or unsubstituted $C_{1-3}$ alkyl, bb is an integer from 1 to 20, and $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group.

In another embodiment, this invention relates to a compound of formula (I) or (II) wherein $R^2$, $R^3$, $R^{3'}$, $R^4$, and $R^{4'}$ are H, $R^5$ and $R^{5'}$ are independently selected from $R^{e1}$, $C(O)N(R^{e2})R^{f2}$, $C(O)OR^{e2}$, $OC(O)N(R^{e2})R^{f2}$, $OC(O)OR^{e2}$, wherein $R^{e1}$ is optionally substituted $C_{1-3}$ alkyl and $R^{e2}$ and $R^{f2}$ are independently selected from H and optionally substituted $C_{1-3}$ alkyl, and $R^{5'}$ may in addition be absent; $R^6$ and $R^{6'}$ are independently selected from H and optionally substituted $C_{1-6}$ alkyl, unsubstituted $C_{1-6}$ heteroalkyl, cyano, or $C_{1-6}$ alkoxy, and $R^{6'}$ may in addition be absent; $R^7$ and $R^{7'}$ are independently selected from H and optionally substituted $C_{1-6}$ alkyl or unsubstituted $C_{1-6}$ heteroalkyl, and $R^{7'}$ may in addition be absent; $R^1$ is selected from halogen and $OSO_2R^o$; $X^4$ is CH; $X^2$ is $C(R^{14})(R^{14'})$; $R^{14}$ and $R^{14'}$ are independently H or optionally substituted $C_{1-6}$ alkyl, and $R^{14'}$ may in addition be absent; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, and $OR^h$, wherein $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group and that none of $R^5$, $R^9$, $R^{10}$, and $R^{11}$ is $O(CH_2)_{bb}N(R^{101})(R^{102})$, wherein $R^{100}$ and $R^{102}$ are independently H or unsubstituted alkyl and bb is an integer from 1 to 20.

In another embodiment, this invention relates to a compound of formula (Ib) wherein $R^2$, $R^4$, and $R^{4'}$ are H, $R^5$ is selected from $R^{e1}$, $C(O)N(R^{e2})R^{f2}$, $C(O)OR^{e2}$, $OC(O)N(R^{e2})R^{f2}$, $OC(O)OR^{e2}$, wherein $R^{e1}$ is optionally substituted $C_{1-3}$ alkyl and $R^{e2}$ and $R^{f2}$ are independently selected from H and optionally substituted $C_{1-3}$ alkyl; $R^6$ is selected from H and optionally substituted $C_{1-6}$ alkyl, unsubstituted $C_{1-6}$ heteroalkyl, cyano, or $C_{1-6}$ alkoxy; $R^7$ is selected from H and optionally substituted $C_{1-6}$ alkyl or unsubstituted $C_{1-6}$ heteroalkyl; $R^1$ is selected from halogen and $OSO_2R^o$; $X^4$ is CH; $X^2$ is $CR^{14}$; $R^{14}$ is H or optionally substituted $C_{1-6}$ alkyl; a is 0; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, and $OR^h$, wherein $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ comprises at least one water-soluble group and that none of $R^8$, $R^9$, $R^{10}$, and $R^{11}$ is $O(CH_2)_{bb}N(R^{101})(R^{102})$, wherein $R^{100}$ and $R^{102}$ are independently H or unsubstituted alkyl and bb is an integer from 1 to 20.

In another embodiment, this invention relates to a compound of formula (I) or (II) wherein $R^2$, $R^3$, $R^{3'}$, $R^4$, and $R^{4'}$ are H, $R^5$ and $R^{5'}$ are independently selected from $R^{e1}$, $C(O)N(R^{e2})R^{f2}$, $C(O)OR^{e2}$, $OC(O)N(R^{e2})R^{f2}$, $OC(O)OR^{e2}$, wherein $R^{e1}$ is substituted methyl or optionally substituted $C_{2-3}$ alkyl, and $R^{e2}$ and $R^{f2}$ are independently selected from H and optionally substituted $C_{1-3}$ alkyl; $R^6$ and $R^{6'}$ are independently selected from H and optionally substituted $C_{1-6}$ alkyl, unsubstituted $C_{1-6}$ heteroalkyl, cyano, or $C_{1-6}$ alkoxy, and $R^{6'}$ may in addition be absent; $R^7$ and $R^{7'}$ are independently selected from H and optionally substituted $C_{1-6}$ alkyl or unsubstituted $C_{1-6}$ heteroalkyl, and $R^{7'}$ may in addition be absent; $R^1$ is selected from halogen and $OSO_2R^o$; $X^4$ is CH; $X^2$ is $C(R^{14})(R^{14'})$; $R^{14}$ and $R^{14'}$ are independently H or optionally substituted $C_{1-6}$ alkyl, and $R^{14'}$ may in addition be absent; $X^3$ is NH; $X^s$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, and $OR^h$, wherein $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that at least one of $R^8$, $R^9$, $R^{10}$, and $R^{11}$ is $O(CH_2)_{bb}N(R^{101})(R^{102})$, wherein $R^{101}$ and $R^{102}$ are independently H or unsubstituted $C_{1-3}$ alkyl and bb is an integer from 1 to 20.

In another embodiment, this invention relates to a compound of formula (I) or (II) wherein $R^2$, $R^3$, $R^{3'}$, $R^4$, and $R^{4'}$ are H, $R^5$ and $R^{5'}$ are independently selected from $R^{e1}$, $C(O)N(R^{e2})R^{f2}$, $C(O)OR^{e2}$ $OC(O)N(R^{e2})R^{f2}$, $OC(O)OR^{e2}$, wherein $R^{e1}$ is optionally substituted $C_{1-3}$ alkyl and $R^{e2}$ and $R^{f2}$ are independently selected from H and optionally substituted $C_{1-3}$ alkyl; $R^6$ and $R^{6'}$ are independently selected from H and optionally substituted $C_{1-6}$ alkyl, unsubstituted $C_{1-6}$ heteroalkyl, cyano, or $C_{1-6}$ alkoxy, and $R^{6'}$ may in addition be absent; $R^7$ and $R^{7'}$ are independently selected from H and optionally substituted $C_{1-6}$ alkyl or unsubstituted $C_{1-6}$ heteroalkyl, and $R^{7'}$ may in addition be absent; $X^2$ is $C(R^{14})(R^{14'})$; $R^{14}$ and $R^{14'}$ are independently H or optionally substituted $C_{1-6}$ alkyl, and $R^{14'}$ may in addition be absent; $R^1$ is selected from halogen and $OSO_2R^o$; $X^4$ is CH; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, and $OR^h$, wherein $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that none of $R^8$, $R^9$, $R^{10}$, and $R^{11}$ comprises a water-soluble group.

In another embodiment, this invention relates to a compound of formula (Ib) wherein $R^2$, $R^4$, and $R^{4'}$ are H, $R^5$ is selected from $R^{e1}$, $C(O)N(R^{e2})R^{f2}$, $C(O)OR^{e2}$, $OC(O)N(R^{e2})R^f$, $OC(O)OR^{e2}$, wherein $R^{e1}$ is optionally substituted $C_{1-3}$ alkyl and $R^{e2}$ and $R^{f2}$ are independently selected from H and optionally substituted $C_{1-3}$ alkyl; $R^6$ is selected from H and optionally substituted $C_{1-6}$ alkyl, unsubstituted $C_{1-6}$ heteroalkyl, cyano, or $C_{1-6}$ alkoxy; $R^7$ is selected from H and optionally substituted $C_{1-6}$ alkyl or unsubstituted $C_{1-6}$ heteroalkyl; $X^2$ is $CR^{14}$; $R^{14}$ is H or optionally substituted $C_{1-6}$ alkyl; a is 0; $R^1$ is selected from halogen and $OSO_2R^o$; $X^4$ is CH; $X^3$ is NH; $X^5$ is O; $R^8$, $R^9$, $R^{10}$, and $R^{11}$ are each independently selected from H, $R^h$, $NO_2$, halogen, $N(R^h)R^i$, $N(R^h)C(O)R^i$, $OC(O)N(R^h)R^i$, $OC(O)OR^h$, $C(O)R^h$, $SR^h$, and $OR^h$, wherein $R^h$ and $R^i$ are independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, provided that none of $R^8$, $R^9$, $R^{10}$, and $R^{11}$ comprises a water-soluble group.

In one embodiment, a compound of this invention is represented by

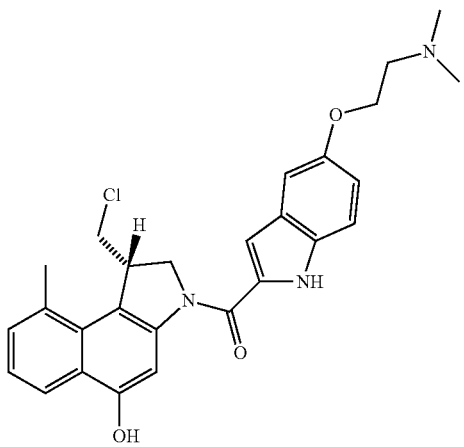 [SMILES: Cc1cccc2c(O)cc3c(c12)[C@H](CCl)CN3C(=O)c1cc2cc(OCCN(C)C)ccc2[nH]1]

or by an isomer, or by a mixture of isomers.

In another embodiment, a compound of this invention is represented by

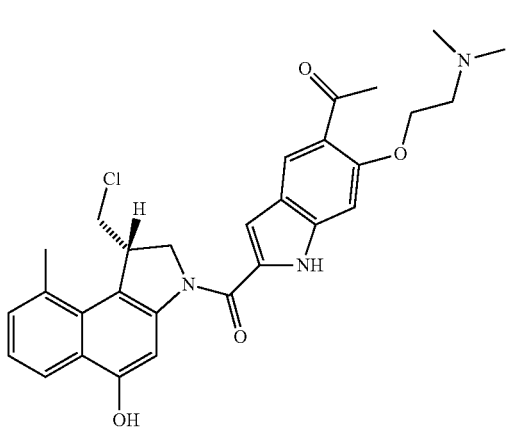 [SMILES: CC(=O)c1cc2cc(C(=O)N3C[C@@H](CCl)c4c3cc(O)c3cccc(C)c43)[nH]c2cc1OCCN(C)C]

or by an isomer, or by a mixture of isomers.

In another embodiment, a compound of this invention is represented by

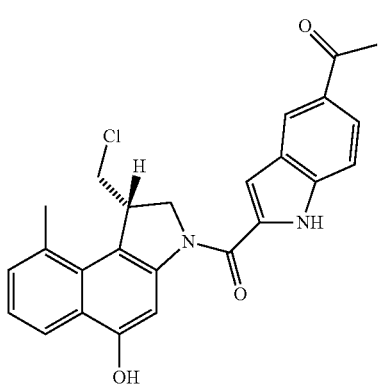 [SMILES: CC(=O)c1ccc2[nH]c(C(=O)N3C[C@@H](CCl)c4c3cc(O)c3cccc(C)c43)cc2c1]

or by an isomer, or by a mixture of isomers.

In another embodiment, a compound of this invention is represented by

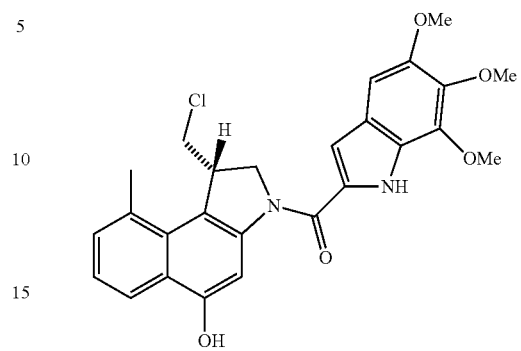

or by an isomer, or by a mixture of isomers.

In another embodiment, a compound of this invention is represented by

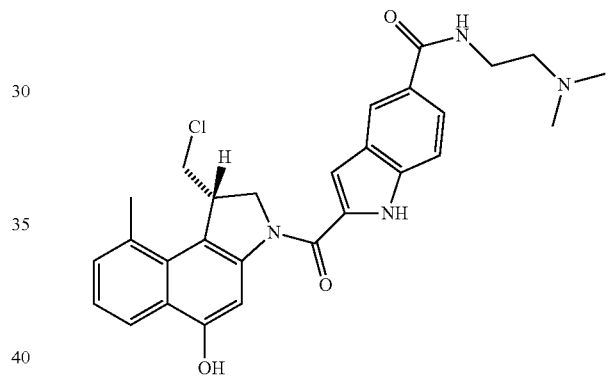

or by an isomer, or by a mixture of isomers.

In another embodiment, a compound of this invention is represented by

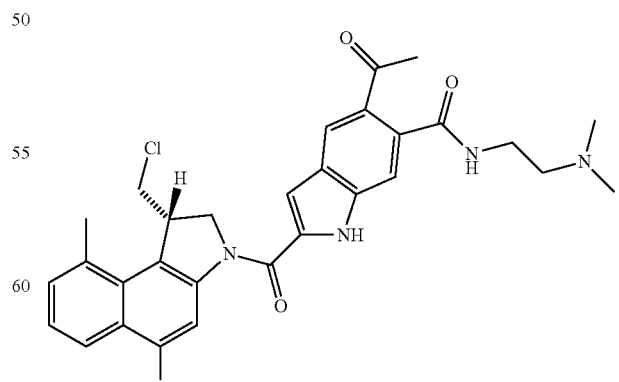

or by an isomer, or by a mixture of isomers.

In another embodiment, a compound of this invention is represented by

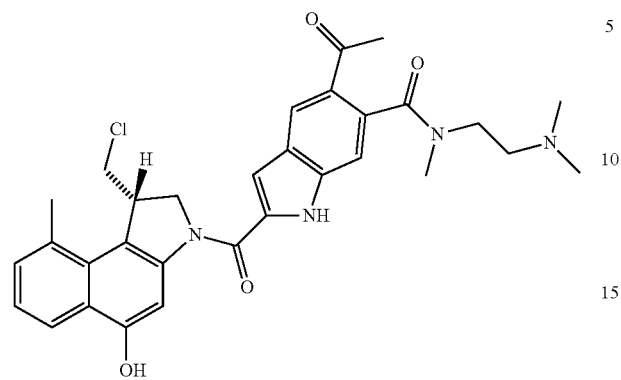

or by an isomer, or by a mixture of isomers.

In another embodiment, a compound of this invention is represented by

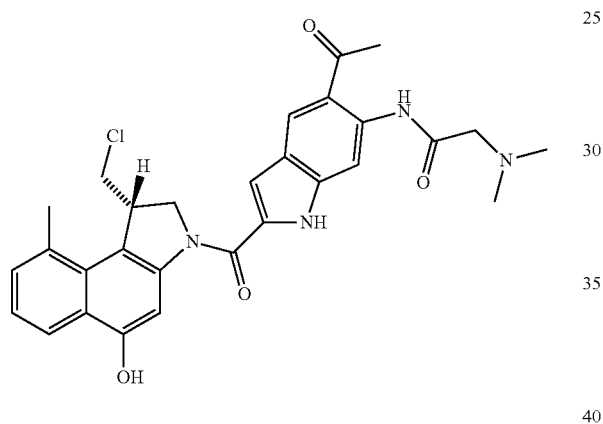

or by an isomer, or by a mixture of isomers.

In another embodiment, a compound of this invention is represented by

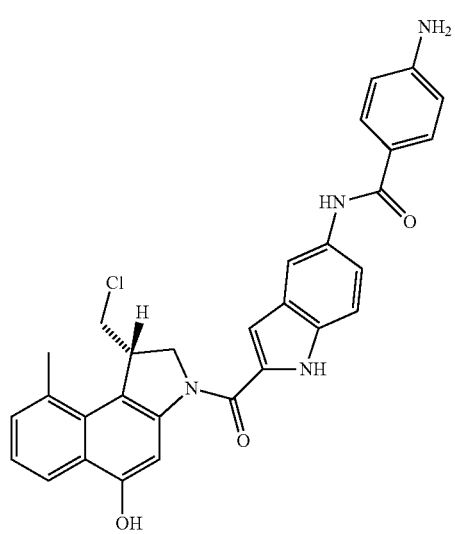 [SMILES: Cc1cccc2c(O)cc3c(c12)[C@H](CCl)CN3C(=O)c1cc2cc(NC(=O)c3ccc(N)cc3)ccc2[nH]1]

or by an isomer, or by a mixture of isomers.

In one embodiment, a compound of this invention is represented by

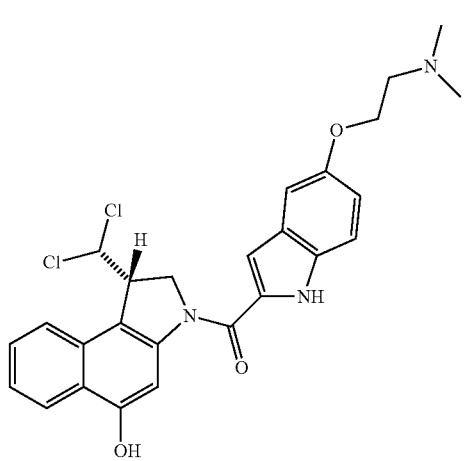 [SMILES: CN(C)CCOc1ccc2[nH]c(C(=O)N3C[C@@H](C(Cl)Cl)c4c3cc(O)c3ccccc43)cc2c1]

or by an isomer, or by a mixture of isomers.

In one embodiment, a compound of this invention is represented by

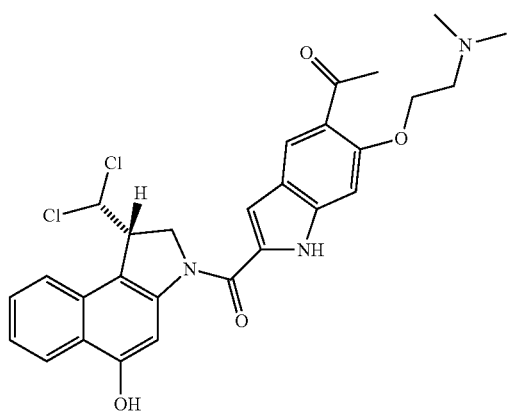 [SMILES: CC(=O)c1cc2cc(C(=O)N3C[C@@H](C(Cl)Cl)c4c3cc(O)c3ccccc43)[nH]c2cc1OCCN(C)C]

or by an isomer, or by a mixture of isomers.

In another embodiment, a compound of this invention is represented by or by an isomer, or by a mixture of isomers.

In another embodiment, a compound of this invention is represented by

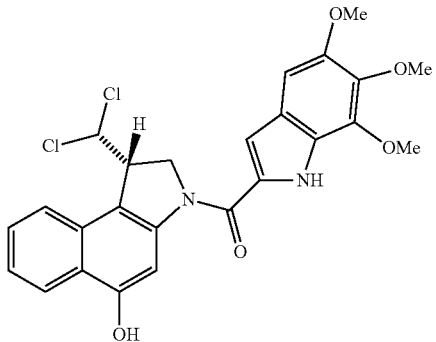 [SMILES: COc1cc2cc(C(=O)N3C[C@@H](C(Cl)Cl)c4c3cc(O)c3ccccc43)[nH]c2c(OC)c1OC]

or by an isomer, or by a mixture of isomers.

Conjugates and Linker-Agent Conjugates

In another aspect, this invention relates to a conjugate of a compound of formula (I) or (II) that can be converted in vivo and in one or more steps to a compound of formula (I) or (II), respectively.

These conjugates may favorably affect the pharmacokinetic properties and other characteristics of a compound of formula (I) or (II). In one embodiment, this invention relates to a conjugate comprising a compound of formula (I) or (II) conjugated to at least one promoiety, i.e., a moiety that can be removed in vivo to release a compound of formula (I) or (II). In another embodiment, this invention relates to a conjugate comprising a compound of formula (I) or (II) conjugated to one promoiety.

In a further embodiment, this invention relates to a compound of formula (III):

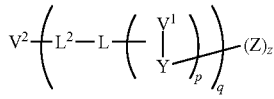

(III)

or a pharmaceutically acceptable salt, hydrate, or solvate thereof, wherein $V^2$ is either absent or a functional moiety;

each $L^2$ is independently absent or a linking group linking $V^2$ to L;

each L is independently absent or a linking group linking $L^2$ to one or more $V^1$ and/or Y;

each $V^1$ is independently absent or a conditionally-cleavable or conditionally-transformable moiety, which can be cleaved or transformed by a chemical, photochemical, physical, biological, or enzymatic process;

each Y is independently absent or a self-eliminating spacer system which is comprised of 1 or more self-elimination spacers and is linked to $V^1$, optionally L, and one or more Z;

each p and q are numbers representing a degree of branching and are each independently a positive integer;

z is a positive integer equal to or smaller than the total number of attachment sites for Z;

each Z is independently a compound of formula (I) or (II) as defined hereinabove wherein one or more of $X^1$, $R^6$, $R^7$, $R^8$, $R^9$, $R^{10}$, and $R^{11}$ may optionally in addition be substituted by a substituent of formula (V):

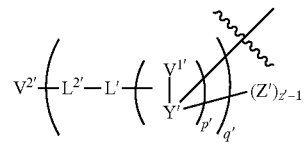

(V)

wherein each $V^{2'}$, $L^{2'}$, $L'$, $V^{1'}$, $Y'$, $Z'$, $p'$, $q'$, and $z'$ has the same meaning as defined for $V^2$, $L^2$, L, $V^1$, Y, Z, p, q, and z, respectively, the one or more substituents of formula (V) being independently connected to one or more of $X^1$, $R^6$, $R^7$, $R^8$, $R^9$, $R^{10}$, and $R^{11}$ via $Y'$, each Z being independently connected to Y through either $X^1$ or an atom in $R^6$, $R^7$, $R^8$, $R^9$, $R^{10}$, or $R^{11}$.

It should be understood from formula (III) that L can either be connected to $V^1$ and/or to Y. If L is connected to Y, this means that both $V^1$ and L, as well as one or more Z, are connected to Y. If L is connected to $V^1$, this means that $V^1$ and one or more Z are connected to Y. L may also be connected to both $V^1$ and Y at the same time. If Y is absent, L is connected to $V^1$ or, if $V^1$ is absent, L is directly connected to Z.

The $V^2(-L^2-L(-(V^1—Y))_p)_q(Z)_{z-1}$ and one or more $V^{2'}(-L^{2'}-L'(-(V^{1'}—Y'))_{p'})_{q'}(Z')_{z'-1}$ moieties connected to a compound of formula (I) or (II) are herein referred to as promoieties.

The present invention also relates to a compound of formula (IV):

(IV)

or a pharmaceutically acceptable salt, hydrate, or solvate thereof, wherein

RM is a reactive moiety and L, $V^1$, Y, Z, p, and z are as defined above, except that L is now linking RM to one or more $V^1$ and/or Y, and $V^1$, Y, and Z may contain protecting groups, and the one or more $V^{2'}$-$L^{2'}$ moieties optionally present in Z as defined hereinabove may optionally and independently be replaced by RM', which is a reactive moiety, and wherein, if there is more than 1 reactive moiety in (IV), some or all reactive moieties are the same or different. These linker-agent conjugates of formula (IV) may or may not be considered intermediates for compounds of formula (III).

The RM-L(-($V^1$—Y))$_p$(Z)$_{z-1}$ and one or more RM'-L'(-($V^{1'}$—Y'))$_{p'}$(Z')$_{z'-1}$ moieties connected to a compound of formula (I) or (II) are herein referred to as promoieties.

It should be understood that this invention relates to enantiomerically pure and/or diastereomerically pure compounds of formulae (III) and (IV) as well as to enantiomeric and/or diastereomeric mixtures of compounds of formulae (III) and (IV).

When a compound of formula (III) or (IV) contains attachment sites for Z that are not coupled to Z, for instance as a consequence of an incomplete coupling reaction during synthesis, these attachment sites are considered to be attached to H, OH, or a leaving group instead. If all of said attachment sites are connected to Z, then z equals the number of said attachment sites; otherwise, z is lower. Compounds of this invention may exist as a mixture, wherein each component of the mixture has a different z value. For example, the compound may exist as a mixture of two separate compounds, one compound wherein z is 4 and another compound wherein z is 3. Furthermore, for a given z, the compound may exist as a mixture of (constitutional) isomers as Z may be connected to distinct sets of attachment sites.

For reasons of clarity, when referring to the connections of one first moiety to other moieties within formula (III) or (IV), in general only those said other moieties are mentioned that are directly next to said first moiety in formula (III) or (IV). It should be understood that if one of said other moieties is not present, said first moiety is actually connected to the moiety first in line that is present, unless explicitly stated otherwise. For example, if it is stated that "$V^1$ is cleaved from Y", this phrase actually means "$V^1$ is cleaved from Y, or from Z if Y is absent" and should be read as "$V^1$ is cleaved from Z" when reference is made to a compound lacking Y.

In a compound of formula (III) or (IV), a compound of formula (I) or (II) may be conjugated to a promoiety through its water-soluble group. In this way, the water-soluble group may contribute less to the water solubility of the compound of formula (III) or (IV), but may contribute again to the water solubility of Z upon removal of said promoiety.

In this document, whenever $V^2$, $L^2$, L, $V^1$, Y, Z, RM, p, q, or z is mentioned, it should be understood that the same can apply for each $V^{2'}$, $L^{2'}$, L', $V^{1'}$, Y', Z', RM', p', q', or z', respectively.

The $V^1$ Moiety

In a compound of formula (III) or (IV), the $V^1$ moiety can be a group that is conditionally cleavable or transformable. In other words, it is designed to be transformed and/or cleaved from Y by a chemical, photochemical, physical, biological, or enzymatic process upon being brought in or under a certain condition. This condition may for example be bringing a compound of the invention in an aqueous environment, which leads to hydrolysis of $V^1$, or bringing a compound of the invention in an environment that contains an enzyme that recognizes and cleaves $V^1$, or bringing a compound of the invention under reducing conditions, which leads to reduction and/or removal of $V^1$, or bringing a compound of the invention under oxidizing conditions, which leads to oxidation and/or removal of $V^1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may be met after administrating a compound of this invention to an animal, e.g., a mammal, for example a human: the condition may be met when the compound localizes to for example a specific organ, tissue, cell, subcellular target, or microbial target, for example by the presence of internal factors (e.g., target-specific enzymes or hypoxia) or application of external factors (e.g., radiation, magnetic fields) or the condition may already be met directly upon administration (e.g., ubiquitous enzymes).

In general, transformation of $V^1$ will directly or indirectly lead to cleavage of $V^1$ from Y. Alternatively, transformation of $V^1$ may lead to formation of a $V^1$—Y moiety which is a self-immolative linker. For example, oxidation of $V^1$ being a hydrogen atom to a hydroxyl group may lead to a para- or ortho-hydroxybenzyl moiety that self-eliminates.

Alternatively again, $V^1$ may be absent. In this instance, the promoiety is intended to be non-removable from Z and the whole promoiety or a part thereof (due to degradation of a compound of formula (III) or (IV) at one or more other sites in the molecule) will stay connected to the one or more moieties Z.

A compound of this invention may contain more than one $V^1$ moiety per promoiety (p and/or q>1). These $V^1$ moieties may or may not be the same and may or may not require the same conditions for transformation and/or cleavage.

In one aspect of this invention, a conjugate is used to target one or more moieties Z to target cells. In this instance, a $V^1$ moiety may for example contain a substrate molecule that is cleaved by an enzyme present in the vicinity of the target cells or inside the target cells, for example tumor cells. $V^1$ can for example contain a substrate that is cleaved by an enzyme present at elevated levels in the vicinity of or inside the target cells as compared to other parts of the body, or by an enzyme that is present only in the vicinity of or inside the target cells.

It is important to recognize that if target cell specificity is achieved solely based upon the selective transformation and/or cleavage of said $V^1$ at the target site, the condition causing the cleavage should preferably, at least to a certain degree, be target cell-specific, whereas the presence of another target-specific moiety in the compound of the invention, for instance in a $V^2$ moiety, reduces or takes away this requirement. For example, when $V^2$ causes selective internalization into a target cell, an enzyme also present in other cells may transform and/or cleave $V^1$. In one embodiment, transformation and/or cleavage of $V^1$ occur intracellularly. In another embodiment, transformation and/or cleavage of $V^1$ occur extracellularly.

In one embodiment, $V^1$ contains a di-, tri-, tetra-, or oligopeptide which consists of an amino acid sequence recognized by a proteolytic enzyme, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment, $V^1$ is a peptide. In another embodiment, $V^1$ is a dipeptide. In another embodiment, $V^1$ is a tripeptide. In another embodiment, $V^1$ is a tetrapeptide. In yet another embodiment, $V^1$ is a peptidomimetic.

In another embodiment, $V^1$ contains a β-glucuronide that is recognized by β-glucuronidase present in the vicinity of or inside tumor cells.

In one embodiment, $V^1$ contains a substrate for an enzyme.

In one embodiment, $V^1$ contains a substrate for an extracellular enzyme.

In another embodiment, $V^1$ contains a substrate for an intracellular enzyme.

In yet another embodiment, $V^1$ contains a substrate for a lysosomal enzyme.

In yet another embodiment, $V^1$ contains a substrate for the serine protease plasmin.

In yet another embodiment, $V^1$ contains a substrate for one or more of the cathepsins, for example cathepsin B.

In yet another embodiment, $V^1$ contains a substrate for a galactosidase.

When $V^1$ is cleaved extracellularly, the one or more Z moieties may be released extracellularly. This may provide the advantage that these Z moieties are not only able to affect the cell(s) directly surrounding the site of activation (e.g., target-positive cells), but also cells somewhat further away from the site of activation (e.g., target-negative cells) due to diffusion (bystander effect).

An enzyme to cleave $V^1$ can also be transported to the vicinity of or inside target cells or target tissue via for example antibody-directed enzyme prodrug therapy (AD-EPT), polymer-directed enzyme prodrug therapy (PDEPT) or macromolecular-directed enzyme prodrug therapy (MD-EPT), virus-directed enzyme prodrug therapy (VDEPT), or gene-directed enzyme prodrug therapy (GDEPT). In one embodiment, transformation and/or cleavage of $V^1$ occur through an enzyme linked to an antibody.

In again another embodiment $V^1$ contains a moiety, for example a nitro (hetero)aromatic moiety, that can be transformed and/or cleaved by reduction under hypoxic conditions or by reduction by a nitroreductase. After reduction of the nitro group and cleavage of the resulting moiety, elimination of the spacer system Y, if present, leads to release of one or more moieties Z.

In one embodiment the invention relates to a conjugate wherein $V^1$ is a dipeptide, tripeptide, tetrapeptide, or oligopeptide moiety comprised of natural L amino acids, unnatural D amino acids, or synthetic amino acids, or a peptidomimetic, or any combination thereof.

In another embodiment the invention relates to a compound wherein $V^1$ comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan, and proline, and the N-terminal amino acid residue of the tripeptide is selected from any natural or unnatural amino acid.

In another embodiment the invention relates to a compound wherein $V^1$ comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid.

In one embodiment, when the α-amino group of the N-terminal amino acid of $V^1$ is not coupled to L, this amino acid may be functionalized with a suitable blocking group coupled to the α-amino group or may be an unnatural amino acid such that undesired premature degradation of $V^1$ by for example ubiquitous enzymes or exopeptidases is prevented.

In a further embodiment $V^1$ is selected from D-alanylphenylalanyllysine, D-valylleucyllysine, D-alanylleucyllysine, D-valylphenylalanyllysine, D-valyltryptophanyllysine, D-alanyltryptophanyllysine, alanylphenylalanyllysine, valylleucyllysine, alanylleucyllysine, valylphenylalanyllysine, valyltryptophanyllysine, alanyltryptophanyllysine, D-alanylphenylalanylcitrulline, D-valylleucylcitrulline, D-alanylleucylcitrulline, D-valylphenylalanylcitrulline, D-valyltryptophanylcitrulline, D-alanyltryptophanylcitrulline, alanylphenylalanylcitrulline, valylleucylcitrulline, alanylleucylcitrulline, valylphenylalanylcitrulline, valyltryptophanylcitrulline, and alanyltryptophanylcitrulline.

In yet another embodiment, $V^1$ is selected from phenylalanyllysine, valyllysine, valylalanine, D-phenylalanylphenylalanyllysine, phenylalanylphenylalanyllysine, glycylphenylalanyllysine, alanyllysine, valylcitrulline, N-methylvalylcitrulline, phenylalanylcitrulline, isoleucylcitrulline, tryptophanyllysine, tryptophanylcitrulline, phenylalanylarginine, phenylalanylalanine, glycylphenylalanylleucylglycine, alanylleucylalanylleucine, alanylarginylarginine, phenylalanyl-$N^9$-tosylarginine, phenylalanyl-$N^9$-nitroarginine, leucyllysine, leucylcitrulline, and phenylalanyl-O-benzoylthreonine.

In a further embodiment, $V^1$ is selected from phenylalanyllysine, valyllysine, and valylcitrulline.

Therefore, in one embodiment this invention relates to a compound wherein $V^1$ contains a substrate that can be cleaved by a proteolytic enzyme, plasmin, a cathepsin, cathepsin B, β-glucuronidase, a galactosidase, prostate-specific antigen (PSA), urokinase-type plasminogen activator (u-PA), a member of the family of matrix metalloproteinases, or an enzyme localized by means of directed enzyme prodrug therapy, such as ADEPT, VDEPT, MDEPT, GDEPT, or PDEPT, or wherein $V^1$ contains a moiety that can be cleaved or transformed through reduction under hypoxic conditions, through reduction by a nitroreductase, or through oxidation.

In another aspect of this invention, a conjugate of this invention is used to (also) improve the (pharmacokinetic) properties of Z. When a promoiety does not need to be selectively removed at a target site, $V^1$ of said promoiety may for example be or contain a group that is cleaved by ubiquitous enzymes, e.g., esterases that are present in the circulation or intracellular enzymes, such as for example proteases and phosphatases, by pH-controlled intramolecular cyclization, or by acid-catalyzed, base-catalyzed, or non-catalyzed hydrolysis, or $V^1$ may for example be or contain a disulfide or form a disulfide with a neighboring moiety. $V^1$ may therefore, optionally together with the connecting atom(s) of L and/or Y, for example form a carbonate, carbamate, ureum, ester, amide, imine, hydrazone, oxime, disulfide, acetal, or ketal group that can be cleaved in vivo. This means that $V^1$, optionally together with the connecting atom(s) of L and/or Y, can for example also represent —OC(O)—, —C(O)O—, —OC(O)O—, —OC(O)N($R^v$)—, —N($R^v$)C(O)—, —C(O)N($R^v$)—, —N($R^v$)C(O)O—, —N($R^v$)C(O)N($R^w$)—, —C(O)—, —OC($R^v$)($R^w$)—, —C($R^v$)($R^w$)O—, —OC($R^v$)($R^w$)O—, —C($R^v$)($R^w$)—, —S—, —S—S—, —C=, =C—, —N=, =N—, —C=N—, —N=C—, —O—N=, =N—O—, —C=N—O—, —O—N=C—, —N($R^v$)—N=, =N—N($R^v$)—, —N($R^v$)—N=C—, or —C=N—N($R^v$)—, wherein $R^v$ and $R^w$ are independently selected from H and optionally substituted $C_{1-10}$ alkyl or $C_{6-10}$ aryl, $R^v$ and $R^w$ optionally being joined by one or more bonds to form one or more optionally substituted carbocycles and/or heterocycles.

If $V^1$ or $V^1$—Y represents a whole promoiety or L is connected to Y and not to $V^1$, $V^1$ may in this case for example be selected from $R^p$—[O($R^{p'}$O)P(O)]$_{pp}$—, $R^p$—C(O)—, $R^p$—OC(O)—, and $R^p$—N($R^p$)C(O)—, wherein pp is selected from 1 to 3 and each $R^p$ and $R^{p'}$ is independently selected from H and optionally substituted $C_{1-15}$ alkyl, $C_{1-15}$ heteroalkyl, $C_{3-15}$ cycloalkyl, $C_{1-15}$ heterocycloalkyl, $C_{6-15}$ aryl, or $C_{1-15}$ heteroaryl, $R^p$ and $R^{p'}$ optionally being joined by a bond to form an optionally substituted carbocycle or heterocycle.

In one embodiment, $V^1$ is selected from phosphono, phenylaminocarbonyl, 4-(piperidino)piperidinocarbonyl, piperazinocarbonyl, and 4-methylpiperazinocarbonyl. $V^1$ itself may contribute to favorable (pharmacokinetic) properties of the conjugate, for example through the presence of polar functional groups in $V^1$.

It should be noted that $V^1$, either in the form of a di-, tri-, tetra-, or oligopeptide, or in any other form, may contain protecting groups. Compounds of the invention comprising such a protected $V^1$ may not release any Z moiety when put under conditions that will transform and/or cleave the corresponding unprotected $V^1$. However, when said compounds are deprotected, such compounds will release one or more Z moieties when put under the appropriate conditions. Compounds comprising such a protected $V^1$ also fall under the scope of this invention. In particular the above can be envisioned for compounds of formula (IV). Suitable protecting groups for functional groups, in particular for amino acids, are well-known to the organic chemist and may for example be found in T. W. Greene, *Protective Groups in Organic Synthesis*, John Wiley & Sons, New York, 1981.

Compounds of formulae (III) and (IV) can be designed to eventually release a compound of formula (I) or (II), or a compound of formula (I') or (II'), after transformation and/or cleavage of the one or more $V^1$ and $V^{1'}$ moieties. Release of a compound of formula (I) or (II), a compound of formula (I') or (II'), or a derivative thereof, from a conjugate of this invention via another mechanism is however not excluded from this invention.

In another aspect of this invention, a compound of formula (III) represents an intermediate for the preparation of a compound of formula (I) or (II) or another compound of formula (III). In this instance, for example, $V^2$, $L^2$, L, and Y are absent, p, q, and z all are 1, and the $V^1$ moiety may be a protecting group. There may or may not be one or more $V^{2'}(-L^{2'}-L'(-(V^{1'}-Y'))_{p'})_{q'}(Z')_{z'-1}$ moieties, in which $V^{2'}$, $L^{2'}$, L', and Y' may or may not be absent, and p', q', and z' all may or may not be 1. In one embodiment, a compound of formula (III) is a compound of formula (I) or (II) to which a $V^1$ moiety is attached. In another embodiment, a compound of formula (III) is a compound of formula (I) or (II) to which a $V^1$ moiety and a $V^{2'}(-L^{2'}-L'(-(V^{1'}-Y'))_{p'})_{q'}(Z')_{z'-1}$ moiety are attached. In yet another embodiment, a compound of formula (III) is a compound of formula (I) or (II) to which a $V^1$ moiety and a $V^{1'}$ moiety are attached.

In one embodiment, $V^1$ is not a protecting group.

In another embodiment, $V^2$, $L^2$, L, and Y are absent, and p, q, and z all are 1.

In a further embodiment, $V^1$ is a chemically removable group.

In yet a further embodiment, $V^1$ is a chemically removable group connected to Z via $X^1$.

In yet another further embodiment, $V^1$ is a benzyl group connected to Z via $X^1$.

In another embodiment, $V^1$ is tert-butoxycarbonyl(methylamino)ethyl(methylamino)carbonyl.

In another embodiment, $V^1$ is 4-(tert-butoxycarbonyl)piperazine-1-carbonyl.

In one embodiment, $V^1$ is connected to L via more than one functional group on $V^1$.

In another embodiment, $V^1$ is connected to L via one functional group on $V^1$.

In another embodiment, $V^1$ is connected to L via a functional group in the side chain of one of the natural or unnatural amino acids of $V^1$.

In another embodiment, the N-terminal amino acid of $V^1$ is connected via its α amino group to L.

In another embodiment, $V^1$ is absent.

The Self-Eliminating Spacer System Y

The self-elimination spacer system Y, if present, links $V^1$ and optionally L to one or more moieties Z.

A self-elimination spacer system Y may be incorporated in a conjugate of this invention to for example improve the properties of Z or the conjugate in general, to provide for suitable coupling chemistries, and/or to create space between $V^1$ and Z.

A compound of this invention may contain more than one spacer system Y per promoiety. These moieties Y may or may not be the same.

After cleavage or transformation of $V^1$, the left-hand side of Y may become unblocked or a $V^1$—Y self-elimination moiety is formed, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art.

In one aspect the invention is related to compounds wherein Y is selected from $(W-)_w(X-)_x(A-)_s$
$(W-)_w(X-)_xC((A)_s-)_r$ or
$(W-)_w(X-)_xC(D((A)_s-)_d)_r$ or
$(W-)_w(X-)_xC(D(E((A)_s-)_e)_d)_r$, or
$(W-)_w(X-)_xC(D(E(F((A)_s-)_f)_e)_d)_r$ wherein
W and X are each a single-release 1,2+2n electronic cascade spacer (n≥1), being the same or different;
A is an ω-amino aminocarbonyl cyclization spacer that forms a cyclic ureum derivative upon cyclization;
C, D, E, and F are each a self-eliminating multiple-release spacer or spacer system that upon activation can maximally release r, d, e, and f groups, respectively;
s is 0 or 1;
r, d, e, and f are numbers representing degree of branching;
w and x are numbers representing degree of polymerization;
r, d, e, and f are independently an integer from 2 (included) to 24 (included);
w and x are independently an integer from 0 (included) to 5 (included).

In a further aspect of the invention, the self-elimination multiple-release spacer systems C, D, E, and F are independently selected from a moiety having the formula:

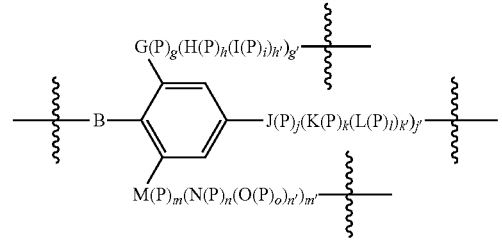

wherein
B is selected from $NR^{21}$, O, and S;
P is $C(R^{22})(R^{23})Q-(W-)_w(X-)_x$;
Q is absent or is —O—CO—;
W and X are each a single-release 1,2+2n electronic cascade spacer (n≥1), being the same or different;
G, H, I, J, K, L, M, N, and O are independently selected from moieties having the formula:

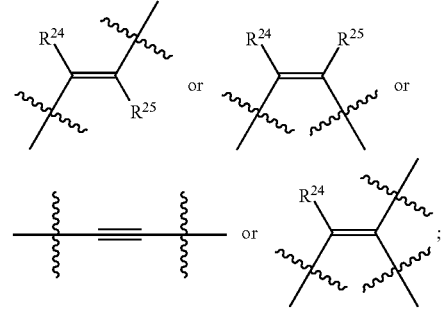

G, J, and M may in addition be selected from the group of P and hydrogen with the proviso that if two of G, J, and M are hydrogen, the remaining group must be

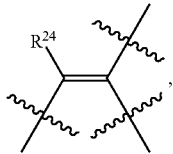

or be

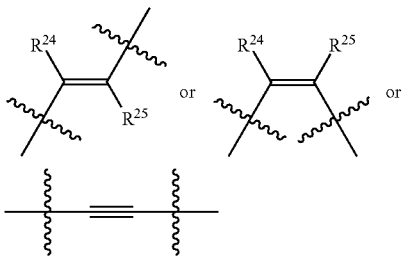

and at the same time be conjugated to

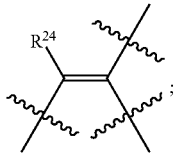

$R^{21}$ is selected from H and optionally substituted $C_1$, alkyl;

$R^{22}$, $R^{23}$, $R^{24}$, and $R^{25}$ are independently selected from H, OH, SH, $NH_2$, $N_3$, $NO_2$, NO, $CF_3$, CN, $C(O)NH_2$, C(O)H, C(O)OH, halogen, $R^x$, $SR^x$, $S(O)R^x$, $S(O)_2R^x$, $S(O)OR^x$, $S(O)_2OR^x$, $OS(O)R^x$, $OS(O)_2R^x$, $OS(O)OR^x$, $OS(O)_2OR^x$, $OR^x$, $NHR^x$, $N(R^x)R^x$, $N(R^x)(R^{x1})R^{x2}$, $P(O)(OR^x)(OR^{x1})$, $OP(O)(OR^x)(OR^{x1})$, $C(O)R^x$, $C(O)OR^x$, $C(O)N(R^{x1})R^x$, $OC(O)R^x$, $OC(O)OR^x$, $OC(O)N(R^x)R^{x1}$, $N(R^{x1})C(O)R^x$, $N(R^{x1})C(O)OR^x$, and $N(R^{x1})C(O)N(R^{x2})R^x$, wherein $R^x$, $R^{x1}$, and $R^{x2}$ are independently selected from H and optionally substituted $C_{1-6}$ alkyl, $C_{1-5}$ heteroalkyl, $C_{3-20}$ cycloalkyl, $C_{1-20}$ heterocycloalkyl, $C_{6-20}$ aryl, or $C_{1-20}$ heteroaryl, $R^x$, $R^{x1}$, and $R^{x2}$ optionally being joined by one or more bonds to form one or more optionally substituted carbocycles and/or heterocycles, two or more of the substituents $R^{21}$, $R^{22}$, $R^{23}$, $R^{24}$, and $R^{25}$ optionally being joined by one or more bonds to form one or more optionally substituted carbocycles and/or heterocycles; g, h, i, j, k, l, m, n, o, h', g', k', j', n', m' are numbers representing degree of branching and are independently 0, 1, or 2 with the provisos that if G=hydrogen or P, g, h, i, h', and g' all equal 0;

if J=hydrogen or P, j, k, l, k', and j' all equal 0;

if M=hydrogen or P, m, n, o, n', and m' all equal 0;

if G, H, I, J, K, L, M, N, or O is

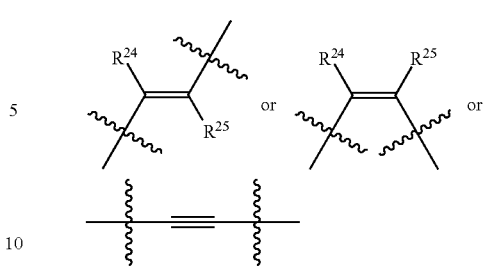

then g+g'=1, h+h'=1, i=1, j+j'=1, k+k'=1, l=1, m+m'=1, n+n'=1, or o=1, respectively;

if G, H, I, J, K, L, M, N, or O is

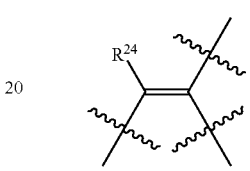

then g+g'=2, h+h'=2, i=2, j+j'=2, k+k'=2, l=2, m+m'=2, n+n'=2, or o=1, respectively;

if g'=0 and G is not hydrogen or P, then h, h', and i equal 0 and g>0;

if g=0 and G is not hydrogen or P, then g>0;

if g'>0 and h'=0, then i=0 and h>0;

if g'>0 and h=0, then h'>0 and i>0;

if j'=0 and J is not hydrogen or P, then k, k', and l equal 0 and j>0;

if j=0 and J is not hydrogen or P, then j>0;

if j'>0 and k'=0, then l=0 and k>0;

if j'>0 and k=0, then k'>0 and l>0;

if m'=0 and M is not hydrogen or P, then n, n', and o equal 0 and m>0;

if m=0 and M is not hydrogen or P, then m'>0;

if m'>0 and n'=0, then o=0 and n>0;

if m'>0 and n=0, then n'>0 and o>0;

w and x are numbers of polymerization and are independently an integer from 0 (included) to 5 (included).

According to a further embodiment of this invention, the 1,2+2n electronic cascade spacers W and X are independently selected from a moiety having the formula:

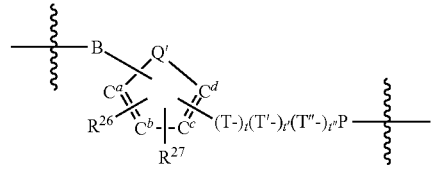

wherein $Q'$=$R^{30}C$=$CR^{31}$—, S, O, $NR^{31}$, —$R^{31}C$=N—, or —N=$CR^{31}$—;

B=$NR^{32}$, O, S;

P=$C(R^{28})(R^{29})Q$;

$R^{26}$, $R^{27}$, B, and (T-)$_t$(T'-)$_{t'}$(T''-)$_{t''}$P are connected to $C^a$, $C^b$, $C^c$, and $C^d$ in such a way that B and (T-)$_t$(T'-)$_{t'}$(T''-)$_{t''}$P are connected to two adjacent carbon atoms or to $C^a$ and $C^d$;

Q is absent or —O—CO—;

t, t', and t'' are numbers representing degree of polymerization and are independently an integer from 0 (included) to 5 (included);

T, T', and T" are independently selected from moieties having the formula:

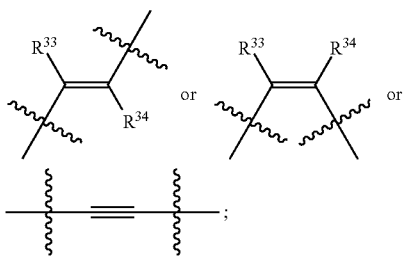

$R^{26}$, $R^{27}$, $R^{28}$, $R^{29}$, $R^{30}$, $R^{31}$, $R^{32}$, $R^{33}$, and $R^{34}$ are independently selected from H, OH, SH, $NH_2$, $N_3$, $NO_2$, NO, $CF_3$, CN, $C(O)NH_2$, C(O)H, C(O)OH, halogen, $R^y$, $SR^y$, $S(O)R^y$, $S(O)_2R^y$, $S(O)OR^y$, $S(O)_2OR^y$, $OS(O)R^y$, $OS(O)_2R^y$, $OS(O)OR^y$, $OS(O)_2OR^y$, $OR^y$, $NHR^y$, $N(R^y)R^{y1}$, $^+N(R^y)(R^{y1})R^{y2}$, $P(O)(OR^y)(OR^{y1})$, $OP(O)(OR^y)(OR^{y1})$, $C(O)R^y$, $C(O)OR^y$, $C(O)N(R^{y1})R^y$, $OC(O)R^y$, $OC(O)OR^y$, $OC(O)N(R^y)R^{y1}$, $N(R^{y1})C(O)R^y$, $N(R^{y1})C(O)OR^y$, and $N(R^{y1})C(O)N(R^{y2})R^y$, wherein $R^y$, $R^{y1}$, and $R^{y2}$ are independently selected from H and optionally substituted $C_{1-6}$ alkyl, $C_{1-6}$ heteroalkyl, $C_{3-20}$ cycloalkyl, $C_{1-20}$ heterocycloalkyl, $C_{6-20}$ aryl, or $C_{1-20}$ heteroaryl, $R^y$, $R^{y1}$, and $R^{y2}$ optionally being joined by one or more bonds to form one or more optionally substituted carbocycles and/or heterocycles, two or more of the substituents $R^{26}$, $R^{27}$, $R^{28}$, $R^{29}$, $R^{30}$, $R^{31}$, $R^{32}$, $R^{33}$ and $R^{34}$ optionally being joined by one or more bonds to form one or more optionally substituted carbocycles and/or heterocycles.

In the formulae above, Q may be O—CO, but it may also be absent. For example, a compound with a benzyl ether linkage between self-elimination spacer and the group that leaves, the oxycarbonyl function being absent (Q is absent), has been reported to undergo self-elimination[11].

According to a further embodiment of the invention, the ω-amino aminocarbonyl cyclization elimination spacer A is a moiety having the formula:

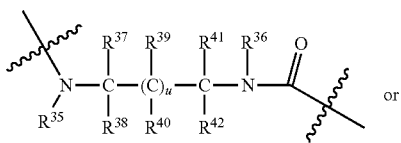

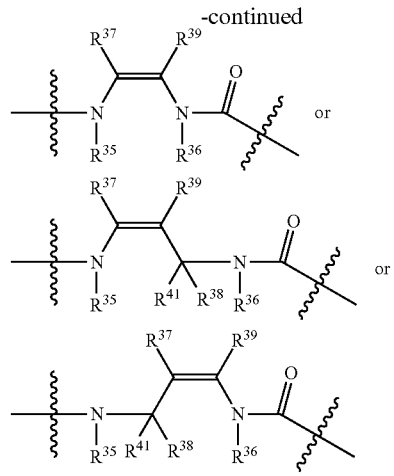

wherein
u is an integer of 0 or 1;
$R^{35}$ and $R^{36}$ are independently selected from H and optionally substituted $C_{1-6}$ alkyl;
$R^{37}$, $R^{38}$, $R^{39}$, $R^{40}$, $R^{41}$, and $R^{42}$ are independently selected from H, OH, SH, $NH_2$, $N_3$, $NO_2$, NO, $CF_3$, CN, $C(O)NH_2$, C(O)H, C(O)OH, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$, wherein $R^z$, $R^{z1}$, and $R^{z2}$ are independently selected from H and optionally substituted $C_{1-6}$ alkyl, $C_{1-6}$ heteroalkyl, $C_{3-20}$ cycloalkyl, $C_{1-20}$ heterocycloalkyl, $C_{6-20}$ aryl, or $C_{1-20}$ heteroaryl, $R^z$, $R^{z1}$, and $R^{z2}$ optionally being joined by one or more bonds to form one or more optionally substituted carbocycles and/or heterocycles, two or more of the substituents $R^{35}$, $R^{36}$, $R^{37}$, $R^{38}$, $R^{39}$, $R^{40}$, $R^{41}$, and $R^{42}$ optionally being joined by one or more bonds to form one or more optionally substituted carbocycles and/or heterocycles.

In one embodiment, Y is absent.
In another embodiment, this invention relates to a compound of formula (II) or (IV) wherein $X^1$ is O and Y is connected to $X^1$ via an ω-amino aminocarbonyl cyclization spacer being part of Y.
In one embodiment, the spacer system Y is selected from

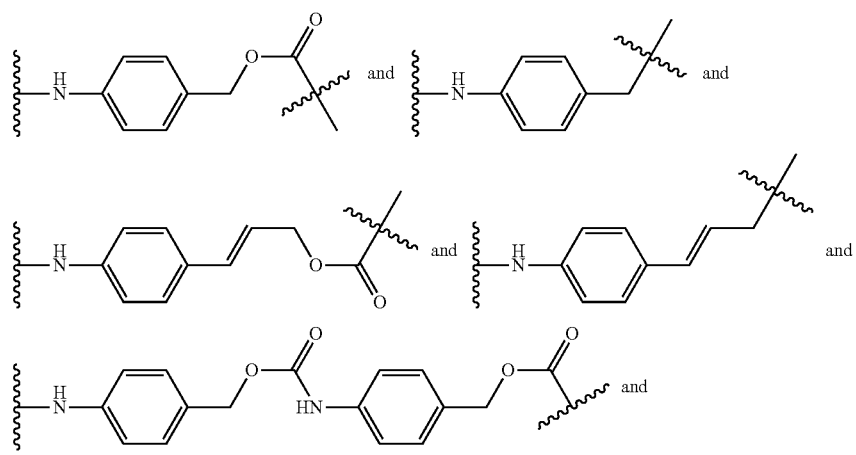

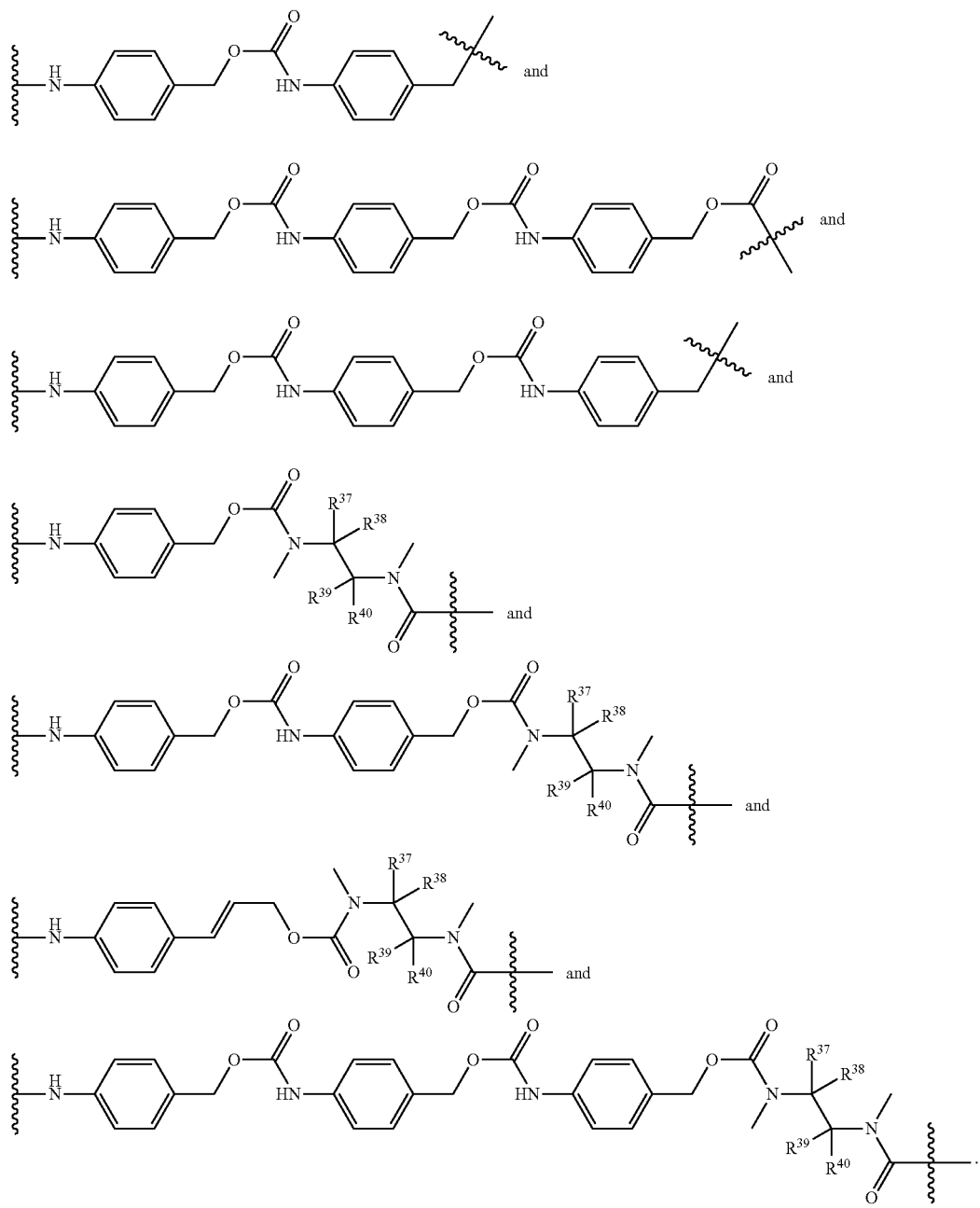
In another embodiment, the spacer system Y is
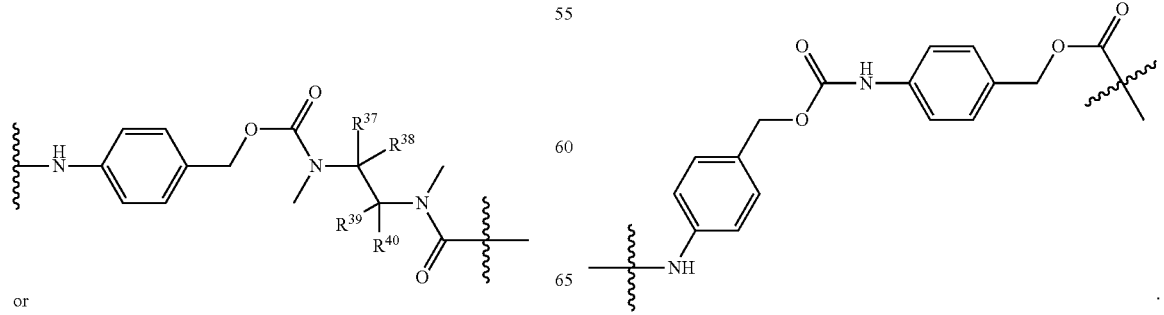

In another embodiment, the spacer system Y is

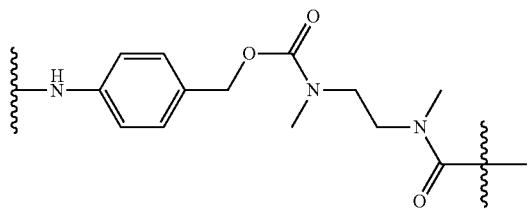

Other examples of self-eliminating spacers include, but are not limited to, spacers that can undergo cyclization[12], such as optionally substituted 4-aminobutyric acid amides, appropriately substituted bicyclo[2.2.1] and bicyclo[2.2.2] ring systems, and 2-aminophenylpropionic acid amides and "trimethyl-lock" cyclization spacers[13]. A glycine spacer in which an amine-containing leaving group is connected at the α-position is another useful spacer for the compounds of the invention.[14]

In a conjugate of this invention, a spacer system Y may be connected to more than one $V^1$ moiety. In this case, transformation and/or cleavage of one of these $V^1$ moieties may trigger the release of one or more Z moieties. When $V^1$ moieties that are transformed or cleaved under different conditions are connected to the same Y, release of one or more Z moieties may occur when a conjugate of this invention is brought under one of several distinct conditions. Alternatively, a spacer system Y may be used that requires to be triggered twice or even more times in order to self-eliminate. An example of such a self-elimination spacer is a bicine spacer.[15] When such a spacer is used in combination with different, selectively cleavable $V^1$ moieties connected to said spacer, selectivity of release of Z may be increased as two different conditions must be met before Z is released.

The Linking Group L

The linking group L links one or more $V^1$ and/or Y moieties to $L^2$ or RM. Synthesis may be more straightforward when L is connected to $V^1$ instead of Y and the compound may be less prone to premature degradation. Connection of L to Y may have the advantage that $V^1$ may be transformed and/or cleaved with more ease. Other reasons to connect L to Y may for example be that (part of) Y remains bound to L upon cleavage of $V^1$, which prevents the release of reactive small molecules, or that the compound displays improved (pharmacokinetic) properties, solubility, or aggregation behavior. L may be absent such that $V^1$ or Y is directly connected to either $L^2$ or RM. In another aspect, however, L is a linking group that functionally links or spaces the one or more $V^1$ and/or Y moieties and the $L^2$ or RM moiety. In a compound of formula (IV), spacing may make the reactive moiety RM more accessible to the reaction partner, for example when the functional moiety is being coupled. In a compound of formula (III), spacing may provide for a better accessibility of $V^1$, because $V^2$ is further removed, which, especially in the case of enzymatic cleavage or transformation of $V^1$, may improve the rate at which $V^1$ is transformed and/or cleaved. The linking group L may be a water-soluble moiety or contain one or more water-soluble moieties, such that L contributes to the water solubility of a compound of formula (III) or (IV). L may also be a moiety or contain one or more moieties that reduce(s) aggregation of a compound of formula (III) or (IV), which may or may not be a moiety/moieties that also increase(s) the water solubility of a compound of formula (III) or (IV). The linking group L must contain suitable functional groups at both of its ends to provide for selective coupling with the one or more $V^1$ and/or Y moieties and $L^2$ or RM.

In one aspect, the L moiety is a linear, branched, or dendritic moiety, so that it can optionally be connected to more than one $V^1$ and/or Y moiety. Branching can occur via one or more cyclic structures or at one or more branching atoms that may for example be carbon, nitrogen, silicon, or phosphorus.

The number of branches in L that are connected to $V^1$ and/or Y does not necessarily equal the total number of branches as in the coupling reaction with $V^1$ and/or Y not all branches may be coupled to $V^1$ and/or Y moieties due to incomplete chemical conversion. This means that L may contain branches that are not coupled to $V^1$ or Y, but instead end in for example a functional group, H, OH, or a leaving group.

Therefore, when L is branched, compounds of this invention may exist as a mixture, wherein each component of the mixture has a different p value. For example, the compound may exist as a mixture of two separate compounds, one compound wherein p is 2 and another compound wherein p is 3. Furthermore, for a given p, the compound may exist as a mixture of (constitutional) isomers as $V^1$ and/or Y may be connected to distinct sets of branches on L.

In one embodiment, L is absent.

In another embodiment, L is a linear linker.

In another embodiment, L is a linear linker built up through a cycloaddition reaction between a molecule containing an azide group and one containing an acetylene group.

In another embodiment, L is a branched linker.

In another embodiment, L is a dendritic linker. The dendritic structure may for example be built up through cycloaddition reactions between molecules containing an azide group and ones containing an acetylene group.

In one embodiment, p is 1.

In other embodiments, p is 2 or 3 or 4 or 6 or 8 or 9.

In another embodiment, L is represented by the formula:

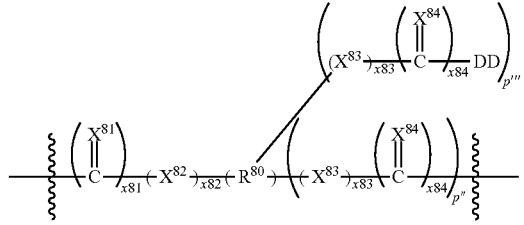

wherein
$X^{81}$ and $X^{82}$ are each independently O, $NR^{85}$, or S;
Each $X^{83}$ and $X^{84}$ is independently O, $NR^{86}$, or S;
Each x81, x82, x83, and x84 is independently 0 or 1;
p" is a number representing a degree of branching and is an integer selected from 1 (included) to 128 (included);
p''' is a number representing a degree of branching and is an integer selected from 0 (included) to 127 (included);
p"+p'''≤128;
Each DD is independently H, OH, or a leaving group;
$R^{80}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_{v'}$—, -alkylene-(CH$_2$CH$_2$O)$_{v'}$—, —(CH$_2$CH$_2$O)$_{v'}$-alkylene-, -alkylene-(CH$_2$CH$_2$O)$_{v'}$-alkylene-, -heteroalkylene-(CH$_2$CH$_2$O)$_{v'}$—, —(CH$_2$CH$_2$O)$_{v'}$-heteroalkylene-, -heteroalkylene-(CH$_2$CH$_2$O)$_{v'}$-alkylene-, -heteroalkylene-(CH$_2$CH$_2$O), -heteroalkylene-, -alkylene-(CH$_2$CH$_2$O), -heteroalkylene-, a dendritic structure, and an oligopeptide, or any combination of two or more of the above;

$R^{85}$ and $R^{86}$ are independently selected from H and C$_{1-8}$ alkyl;

v' is selected from 1 (included) to 500 (included).

For example, L may be selected from optionally substituted C$_{1-10}$ alkylene, C$_{1-10}$ alkylenecarbonyl, C$_{1-12}$ alkyleneoxycarbonyl, C$_{1-12}$ carbonylalkylene, C$_{1-12}$ carbonylalkyleneoxycarbonyl, C$_{1-12}$ alkyleneaminocarbonyl, C$_{1-12}$ alkylene(methylamino)carbonyl, and (CH$_2$CH$_2$O)$_{v'}$-carbonyl.

In one embodiment, L is selected from

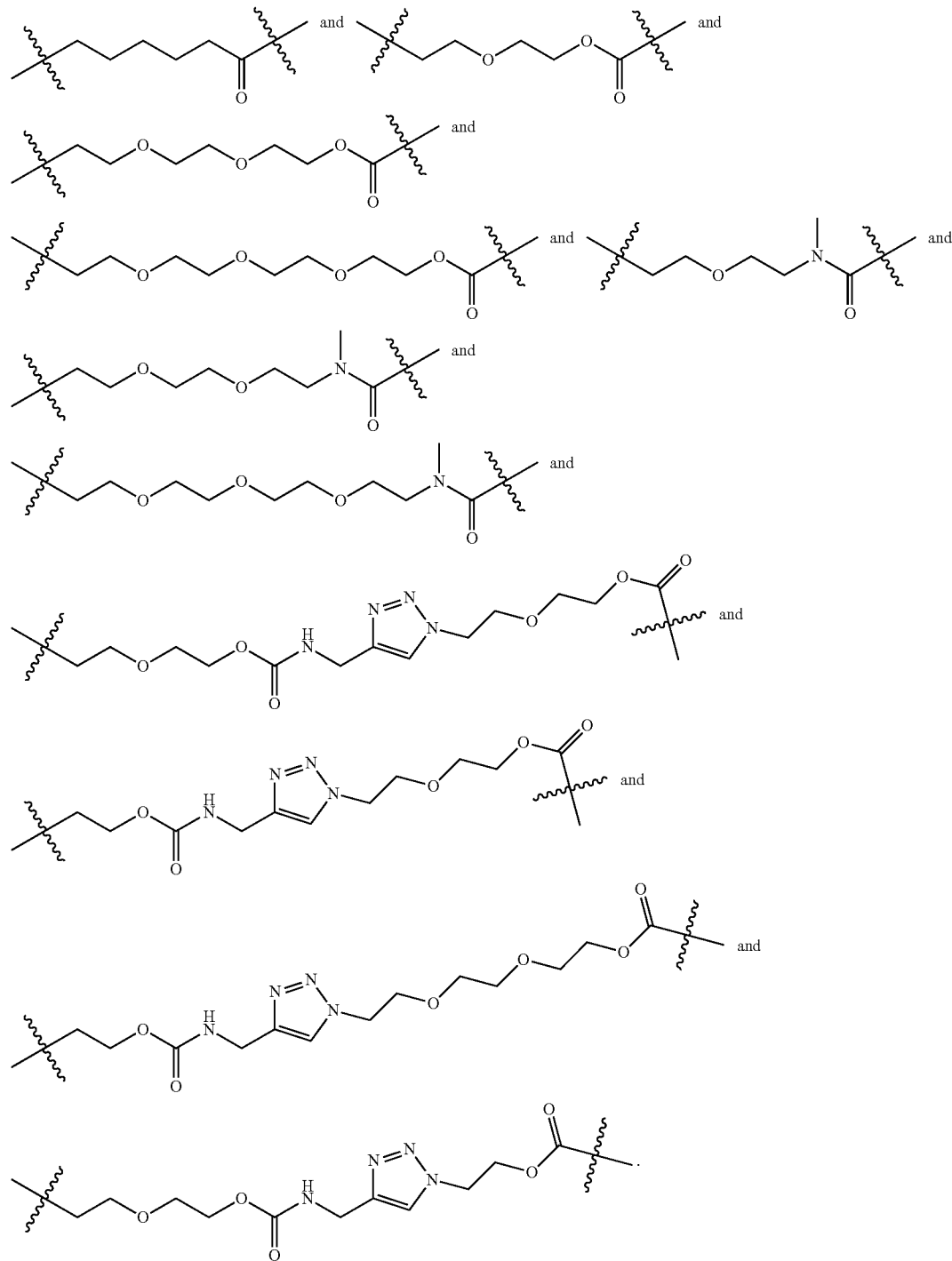

The Reactive Moiety RM and the Linking Group L²

The reactive moiety RM in a compound of formula (IV) is connected to the linking group L and is able to react with a suitable functional group on a reaction partner.

In one embodiment of this invention, the reactive moiety RM is designed to react with a functional group on the moiety V², which results in formation of a compound of formula (III). In this reaction, the moiety RM is transformed into the moiety L². In another embodiment, the reactive moiety RM is designed to react with a complementary moiety in situ, e.g., in vivo, to give a compound that may or may not be a compound of formula (III).

In one aspect of this invention, the reactive moiety RM contains an electrophilic group that reacts with a nucleophilic group on the reaction partner, for example V², e.g., a thiol group, an amino group, or a hydroxy group.

In another aspect of this invention, the reactive moiety RM contains a nucleophilic group that reacts with an electrophilic group on the reaction partner, for example V², e.g., an aldehyde group.

In another aspect of the invention, the reactive moiety RM contains a cycloaddition partner moiety, e.g., an alkene, a diene, a 1,3-dipole, or a 1,3-dipolarophile, that reacts with a suitable complementary cycloaddition partner moiety on the reaction partner, for example V², e.g., a diene, an alkene, a 1,3-dipolarophile, or a 1,3-dipole.

In another aspect of the invention, the reactive moiety RM contains a group that can be coupled with a suitable complementary group on the reaction partner, for example V², under metal-catalyzed, biocatalyzed, or enzyme-catalyzed conditions, e.g., palladium-catalyzed conditions.

In one aspect of the invention, the reactive moiety RM is, without limitation,

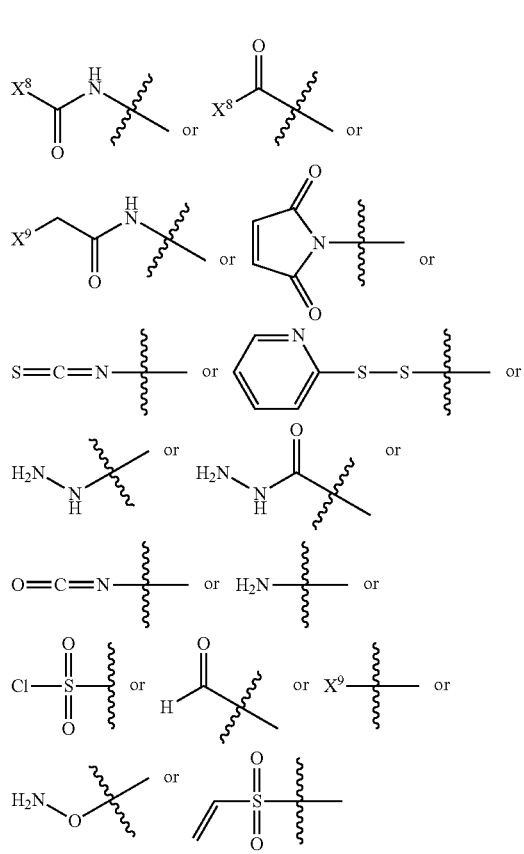

wherein $X^8$ is selected from —Cl, —Br, —I, —F, —OH, —O—N-succinimide, —O-(4-nitrophenyl), —O-pentafluorophenyl, —O-tetrafluorophenyl, —O—C(O)—R$^{50}$, and —O—C(O)—OR$^{50}$;

$X^9$ is selected from —Cl, —Br, —I, —O-mesyl, —O-triflyl, and —O-tosyl;

$R^{50}$ is selected from $C_{1-10}$ alkyl and $C_{6-10}$ aryl.

In one embodiment, the moiety RM is selected from

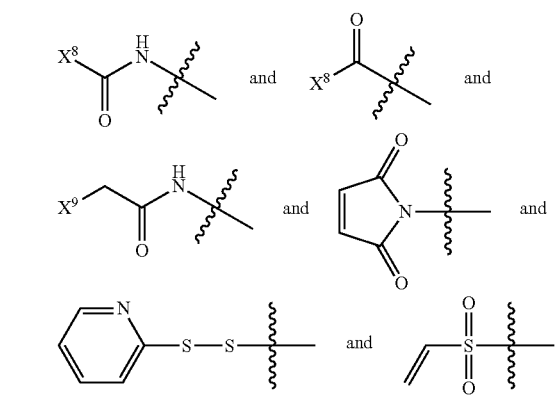

which makes it able to react with a thiol group on the reaction partner, for example moiety V².

In another embodiment, the moiety RM is

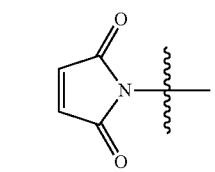 [SMILES: *N1C(=O)C=CC1=O]

which makes it able to react with a thiol group on the reaction partner, for example moiety V².

In another embodiment, the moiety RM is selected from

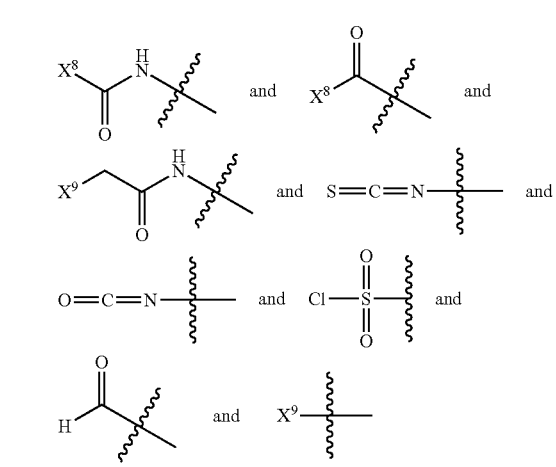

which makes it able to react with an amino group, e.g., a primary or secondary amino group, on the reaction partner, for example moiety V².

In another embodiment, the moiety RM is selected from

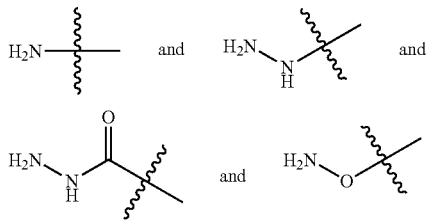

which makes it able to react with an aldehyde group on the reaction partner, for example moiety $V^2$.

The linking group $L^2$ in a compound of formula (III) represents the remainder of RM when the reactive moiety RM has reacted with $V^2$. This group then links the moiety $V^2$ with L. The group that remains may be a bond, meaning that $L^2$ is absent. Typically, however, $L^2$ is a linking group. When a compound of formula (III) is formed other than via a compound of formula (IV), $L^2$ does not represent the remainder of RM, but may represent a similar or the same moiety and in addition be selected from for example optionally substituted $C_{1-6}$ alkylene, $C_{1-6}$ heteroalkylene, $C_{3-7}$ cycloalkylene, $C_{1-7}$ heterocycloalkylene, $C_{6-10}$ arylene, and $C_{1-10}$ heteroarylene.

In one embodiment, the moiety $L^2$ is absent.

In another embodiment, the moiety $L^2$ is, without limitation,

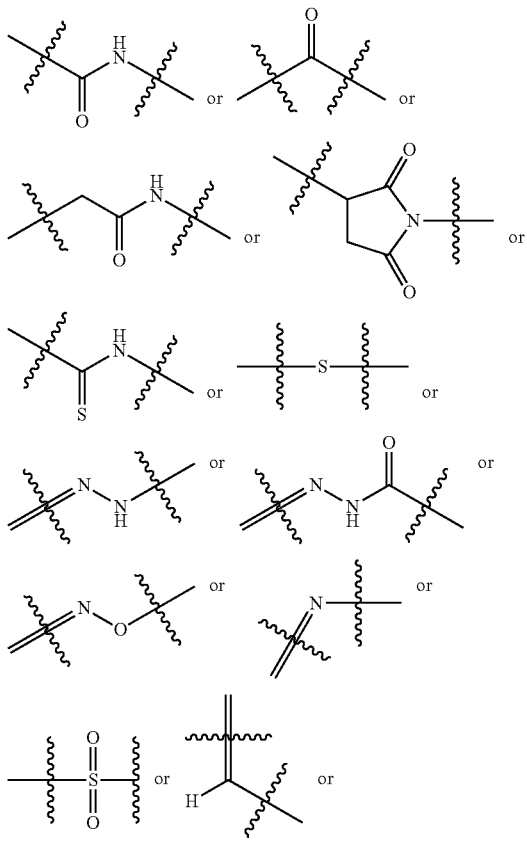

-continued

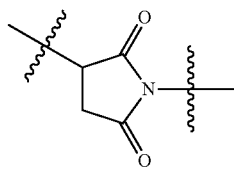

In a further embodiment, the moiety $L^2$ is

The Moiety $V^2$

The moiety $V^2$ is a functional moiety, which means that it adds additional functionality to a compound of the invention.

In one embodiment, $V^2$ is a targeting moiety. In another embodiment, the $V^2$ moiety is a moiety that improves the pharmacokinetic properties of a compound of the invention. In yet another embodiment, the $V^2$ moiety is a moiety that causes accumulation of a compound of the invention at a target site. In yet another embodiment, the $V^2$ moiety is a moiety that improves the aqueous solubility of a compound of the invention. In yet another embodiment, the $V^2$ moiety is a moiety that increases the hydrophobicity of a compound of the invention. In yet another embodiment, the $V^2$ moiety is a moiety that reduces extravasation of a compound of the invention. In yet another embodiment, the $V^2$ moiety is a moiety that reduces excretion of a compound of the invention. In yet another embodiment, the $V^2$ moiety is a moiety that reduces the immunogenicity of a compound of the invention. In yet another embodiment, the $V^2$ moiety is a moiety that enhances the circulation time of a compound of the invention. In yet another embodiment, the $V^2$ moiety is a moiety that enhances the ability of a compound of the invention to cross a biological barrier, e.g., a membrane, cell wall, or the blood-brain barrier. In yet another embodiment, the $V^2$ moiety is a moiety that enhances the ability of a compound of the invention to internalize. In yet another embodiment, the $V^2$ moiety is a moiety that causes the compounds of the invention to aggregate. In yet another embodiment, the $V^2$ moiety is a moiety that reduces aggregation of a compound of the invention. In yet another embodiment, the $V^2$ moiety is a moiety that causes a compound of the invention to form micelles or liposomes. In yet another embodiment, the $V^2$ moiety is a moiety that causes complexation of a compound of the invention to another molecule, e.g., a biomolecule. In yet another embodiment, the $V^2$ moiety is a polynucleotide moiety that complexes with a complementary nucleotide sequence, for example RNA or DNA. In yet another embodiment, the $V^2$ moiety is a moiety that causes a compound of the invention to bind, associate, interact, or complex to another moiety, for example a (functionalized) surface or solid support.

In another embodiment, $V^2$ exhibits two or more different functions.

In one aspect of the invention, the moiety $V^2$ includes within its scope any unit that binds or reactively associates or complexes with a receptor, a receptor complex, antigen, or other receptive moiety associated with a given target cell population. $V^2$ can be any molecule that binds to, complexes with, or reacts with a moiety of a cell population sought to be therapeutically or otherwise biologically modified. The $V^2$ moiety acts to deliver the one or more moieties Z to the particular target cell population with which $V^2$ reacts or to which $V^2$ binds. Such $V^2$ moieties include, but are not limited to, aptamers, full-length antibodies and antibody fragments, lectins, biologic response modifiers, enzymes, vitamins, growth factors, steroids, nutrients, sugar residues, oligosaccharide residues, hormones, and any derivatives thereof, or any combination of any of these. Upon binding, reactively associating, or complexing, the compounds of the invention may or may not be internalized. If internalization occurs, transformation and/or cleavage of $V^1$ preferably occur inside the target cell.

Useful non-immunoreactive protein, polypeptide, or peptide $V^2$ moieties include, but are not limited to, transferrin, epidermal growth factors ("EGF"), bombesin, gastrin and its derivatives, gastrin-releasing peptide, platelet-derived growth factor, IL-2, IL-6, transforming growth factors ("TGF"), such as TGF-a and TGF-P, tumor growth factors, vaccinia growth factor ("VGF"), insulin and insulin-like growth factors I and II, lectins, and apoprotein from low density lipoprotein.

Useful polyclonal antibody $V^2$ moieties are heterogeneous populations of antibody molecules. Various procedures well-known in the art may be used for the production of polyclonal antibodies to an antigen-of-interest.

Useful monoclonal antibody $V^2$ moieties are homogeneous populations of antibodies to a particular antigen (e.g., a cancer cell antigen). A monoclonal antibody (mAb) to an antigen-of-interest can be prepared by using any technique known in the art which provides for the production of monoclonal antibody molecules.

Useful monoclonal antibody $V^2$ moieties include, but are not limited to, human monoclonal antibodies, humanized monoclonal antibodies, or chimeric human-mouse (or other species) monoclonal antibodies. Human monoclonal antibodies may be made by any of numerous techniques known in the art.

The $V^2$ moiety can also be a bispecific antibody. Methods for making bispecific antibodies are known in the art.

The $V^2$ moiety can be a functionally active fragment, derivative, or analog of an antibody that immunospecifically binds to an antigen on a target cell, e.g., a cancer cell antigen. In this regard, "functionally active" means that the fragment, derivative, or analog is able to elicit anti-anti-idiotype antibodies that recognize the same antigen that the antibody from which the fragment, derivative, or analog is derived, recognizes.

Other useful $V^2$ moieties comprise fragments of antibodies including, but not limited to, F(ab')$_2$ fragments, which contain the variable region, the light chain constant region, and the CHI domain of the heavy chain, which can be produced by pepsin digestion of the antibody molecule, and Fab fragments, which can be generated by reducing the disulfide bridges of the F(ab')$_2$ fragments. Other useful $V^2$ moieties are heavy chain and light chain dimers of antibodies, or any minimal fragment thereof such as Fvs or single chain antibodies (SCAs), domain antibodies, anticalins, affibodies, nanobodies, and any other molecules with the same, similar, or comparable specificity as the parent antibody.

Additionally, recombinant antibodies, such as chimeric and humanized monoclonal antibodies, comprising both human and non-human portions, which can be made using standard recombinant DNA techniques, are useful $V^2$ moieties. A chimeric antibody is a molecule in which different portions are derived from different animal species, such as those having a variable region derived from a murine monoclonal and a human immunoglobulin constant region. Humanized antibodies are antibody molecules from non-human species having one or more complementarity determining regions (CDRs) from the non-human species and a framework region from a human immunoglobulin molecule.

Completely human antibodies are particularly desirable as $V^2$ moieties. Such antibodies can for example be produced using transgenic mice that are incapable of expressing endogenous immunoglobulin heavy and light chains genes, but which can express human heavy and light chain genes. In other embodiments, the $V^2$ moiety is a fusion protein of an antibody, or a functionally active fragment or derivative thereof, for example one in which the antibody is fused via a covalent bond (e.g., a peptide bond) at either the N-terminus or the C-terminus to an amino acid sequence of another protein (or portion thereof, preferably at least a 10, 20, or 50 amino acid portion of the protein) that is not the antibody. Preferably, the antibody or fragment thereof is covalently linked to the other protein at the N-terminus of the constant domain.

The $V^2$ moiety antibodies include analogs and derivatives that are modified, i.e., by the covalent attachment of any type of molecule as long as such covalent attachment permits the antibody to retain its antigen binding immunospecificity. For example, but not by way of limitation, derivatives and analogs of antibodies include those that have been further modified, e.g., by glycosylation, acetylation, pegylation, disulfide reduction, phosphylation, amidation, derivatization by known protecting or blocking groups, proteolytic cleavage, linkage to an other protein, etc. Additionally, the analog or derivative can contain one or more unnatural amino acids.

The $V^2$ moiety antibodies include antibodies having modifications (e.g., substitutions (for example cysteine to serine), deletions, or additions) in amino acid residues that interact with Fc receptors. In particular, they include antibodies having modifications in amino acid residues identified as involved in the interaction between the Fc domain and the FcRn receptor. Modifications may also be introduced to be able to couple the antibody to linker-agent conjugates at specific positions on the antibody.

In a specific embodiment, an antibody immunospecific for a cancer or tumor antigen is used as a $V^2$ moiety in accordance with the compounds, compositions, and methods of the invention.

Antibodies immunospecific for a cancer cell antigen can be obtained commercially or produced by any method known to one of skill in the art, such as chemical synthesis or recombinant expression techniques. The nucleotide sequences encoding antibodies immunospecific for a cancer cell antigen can be obtained, e.g., from the GenBank database or a database like it, a commercial or other source, literature publications, or by routine cloning and sequencing.

Examples of antibodies available for the treatment of cancer include, but are not limited to, HERCEPTIN (trastuzumab; Genentech, CA) which is a humanized anti-HER2 monoclonal antibody for the treatment of patients with metastatic breast cancer; RITUXAN (rituximab; Genentech, CA), which is a chimeric anti-CD20 monoclonal antibody for the treatment of patients with non-Hodgkin's lymphoma; OvaRex (oregovomab; AltaRex Corporation, MA) which is a murine antibody for the treatment of ovarian cancer; Panorex (edrecolomab; Glaxo Wellcome, NC) which is a murine IgG$_{2a}$ antibody for the treatment of colorectal cancer; IMC-BEC2 (mitumomab; ImClone Systems, NY) which is a murine IgG antibody for the treatment of lung cancer; IMC-C225 (crbitux; Imclone Systems, NY) which is a chimeric IgG antibody for the treatment of head and neck cancer; Vitaxin (MedImmune, MD) which is a humanized antibody for the treatment of sarcoma; Campath I/H (alemtuzumab, Leukosite, MA) which is a humanized $IgG_1$ antibody for the treatment of chronic lymphocytic leukemia (CLL); SGN-70 (Seattle Genetics, WA) which is a humanized anti-CD70 antibody for the treatment of hematologic malignancies; Smart MI95 (Protein Design Labs, CA) which is a humanized IgG antibody for the treatment of acute myeloid leukemia (AML); LymphoCide (epratuzumab, Immunomedics, NJ) which is a humanized IgG antibody for the treatment of non-Hodgkin's lymphoma; SGN-33 (Seattle Genetics, WA) which is a humanized anti-CD33 antibody for the treatment of acute myeloid leukemia; Smart ID 10 (Protein Design Labs, CA) which is a humanized antibody for the treatment of non-Hodgkin's lymphoma; Oncolym (Techniclone, CA) which is a murine antibody for the treatment of non-Hodgkin's lymphoma; Allomune (BioTransplant, CA) which is a humanized anti-CD2 mAb for the treatment of Hodgkin's disease or non-Hodgkin's lymphoma; anti-VEGF (Genentech, CA) which is a humanized antibody for the treatment of lung and colorectal cancers; SGN-40 (Seattle Genetics, WA) which is a humanized anti-CD40 antibody for the treatment of multiple myeloma; SGN-30 (Seattle Genetics, WA) which is a chimeric anti-CD30 antibody for the treatment of Hodgkin's disease; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone Systems, NJ) which is an anti-EGFR chimeric antibody for the treatment of epidermal growth factor positive cancers.

Other antibodies useful in the treatment of cancer include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor receptors, interleukin receptors, CanAg, PEM, AFP, HER2, EGFR, VEGFR1, VEGFR2, MAGE-1, LUCA, LUCA2, MAGE-2, MAGE-3, MAGE-4, anti-transferrin receptor, Eph receptor tyrosine kinases, PSCA, CLL-1, EphA2, EphB2, FLT3, p97, MUC1-KLH, MUC18, MUC16, PSMA, EpCAM, CTLA4, CEA, GD2, gp100, GD3 ganglioside, GPC-3, MARTI, PSA, IL-2 receptor, CD2, CD4, CD20, CD44, CD30, CD55, CD19, CD79, CD52, CD25, CD46, CD56, CD7, CD74, CD133, CD80, CD140b, CD33, CD22, HLA-DR, HLA-DR10, human chorionic gonadotropin, CD38, CD40, CD70, mucin, P21, MPG, and Neu oncogene product. Many other internalizing or non-internalizing antibodies that bind to tumor-associated antigens can be used in this invention, some of which have been reviewed[16].

In some embodiments, the antibody is an anti-nuclear antibody or an antibody that can bind to a receptor or receptor complex expressed on a target cell. The receptor or receptor complex can comprise an immunoglobulin gene superfamily member, an integrin, a chemokine receptor, a TNF receptor superfamily member, a cytokine receptor, a major histocompatibility protein, a complement control protein, or a lectin.

In another specific embodiment, an antibody immunospecific for an antigen associated with an autoimmune disease is used as a $V^2$ moiety in accordance with the compounds, compositions, and methods of the invention.

In another specific embodiment, an antibody immunospecific for a viral or microbial antigen is used as a $V^2$ moiety in accordance with the compounds, compositions, and methods of the invention. As used herein, the term "viral antigen" includes, but is not limited to, any viral peptide or polypeptide protein that is capable of eliciting an immune response. As used herein, the term "microbial antigen" includes, but is not limited to, any microbial peptide, polypeptide, protein, saccharide, polysaccharide, or lipid that is capable of eliciting an immune response.

New antibodies are continually being discovered and developed, and the present invention provides that these new antibodies may also be incorporated into a compound of this invention.

$V^2$ can react with the reactive moiety RM via for example a heteroatom on $V^2$. Heteroatoms that may be present on $V^2$ include, without limitation, sulfur (in one embodiment, from a sulfhydryl group), oxygen (in one embodiment, from a carboxyl or hydroxyl group), and nitrogen (in one embodiment, from a primary or secondary amino group). $V^2$ may also react via for example a carbon atom (in one embodiment, from a carbonyl group). These atoms can be present on $V^2$ in $V^2$'s natural state, for example a naturally occurring antibody, or can be introduced into $V^2$ via (chemical) modification.

Free sulfhydryl groups can be generated in an antibody or antibody fragment by reduction of the antibody (fragment) with a reducing agent such as dithiothreitol (DTT) or tris(2-carboxyethyl)phosphinc (TCEP). In this way, modified antibodies can be obtained that can have from 1 to about 20 sulfhydryl groups, but typically between about 1 and about 9 sulfhydryl groups.

Alternatively, $V^2$ can have one or more carbohydrate groups that can be chemically modified to have one or more sulfhydryl groups. As another alternative, sulfhydryl groups can be generated by reaction of amino groups, for example from lysine moieties, on $V^2$ with 2-iminothiolane (Traut's reagent) or another sulfhydryl-generating reagent.

In one embodiment, the $V^2$ moiety is a receptor-binding moiety.

In another embodiment, the $V^2$ moiety is an antibody or an antibody fragment.

In another embodiment, the $V^2$ moiety is a monoclonal antibody or a fragment thereof.

In one embodiment, $V^2$ has one or more sulfhydryl groups and $V^2$ reacts with one or more RM moieties of compounds of formula (IV) via one or more of these sulfhydryl groups' sulfur atoms to form a compound of formula (III).

In yet another embodiment, $V^2$ contains one or more disulfide bonds that can be chemically reduced to sulfhydryl groups (two for each disulfide bond), which can then be reacted with one or more reactive moieties RM.

In another embodiment, $V^2$ contains about 1 to about 3 sulfhydryl groups, which can be reacted with one or more reactive moieties RM.

In another embodiment, $V^2$ contains about 3 to about 5 sulfhydryl groups, which can be reacted with one or more reactive moieties RM.

In another embodiment, $V^2$ contains about 7 to about 9 sulfhydryl groups, which can be reacted with one or more reactive moieties RM.

In another embodiment, $V^2$ can have one or more carbohydrate groups that can be chemically modified to have one or more sulfhydryl groups. $V^2$ reacts with RM moieties via these one or more sulfhydryl groups' sulfur atoms.

In another embodiment, $V^2$ can have one or more lysine groups that can be chemically modified to have one or more sulfhydryl groups, which can be reacted with one or more reactive moieties RM.

Reactive moieties that can react with a sulfhydryl group include, but are not limited to, carbamoyl halide, acyl halide, α-haloacetamide, halomethyl ketone, vinyl sulfone, maleimide, and 2-disulfanylpyridine.

In yet another embodiment, $V^2$ can have one or more carbohydrate groups that can be oxidized to provide one or more aldehyde groups. The corresponding aldehyde(s) can then react with one or more reactive moieties RM. Reactive moieties that can react with a carbonyl group on $V^2$ include, but are not limited to, hydrazine, hydrazide, amine, and hydroxylamine.

In yet another embodiment, $V^2$ can have one or more amino groups, e.g., from lysine residues, which can be reacted with one or more reactive moieties RM. Reactive moieties that can react with an amino group include, but are not limited to, carbamoyl halide, α-haloacetamide, acyl halide, aldehyde, sulfonyl chloride, alkyl halide, alkyl sulfonate, isocyanate, and isothiocyanate.

A conjugate of formula (III) may exist as a mixture, wherein each component of the mixture has a different q value. For example, the compound may exist as a mixture of two separate compounds, one compound wherein q is 3 and another compound wherein q is 4. When analyzing the compound of formula (III) it is understood that q may be the (rounded) average number of $L^2\text{-}L(\text{-}(V^1\text{—}Y))_p(Z)_{z/q}$ units per $V^2$ moiety. Furthermore, for a given q, the compound may exist as a mixture of (constitutional) isomers as the q $L^2\text{-}L(\text{-}(V^1\text{—}Y))_p(Z)_{z/q}$ moieties may be connected to distinct sets of functional groups on $V^2$. It should be noted that the number of Z moieties in each unit only equals z/q if all units are the same and/or contain the same number of Z moieties.

In one embodiment, the $V^2$ moiety is connected to $L^2$ via a sulfur atom of $V^2$.

In another embodiment, the $V^2$ moiety is connected to $L^2$ via a sulfur atom and q ranges from about 1 to about 20.

In another embodiment, the $V^2$ moiety is connected to $L^2$ via a sulfur atom and q ranges from about 1 to about 9.

In another embodiment, the $V^2$ moiety is connected to $L^z$ via a sulfur atom and q ranges from about 1 to about 3.

In another embodiment, the $V^2$ moiety is connected to $L^2$ via a sulfur atom and q is about 2.

In another embodiment, the $V^2$ moiety is connected to $L^2$ via a sulfur atom and q ranges from about 3 to about 5.

In another embodiment, the $V^2$ moiety is connected to $L^2$ via a sulfur atom and q is about 4.

In another embodiment, the $V^2$ moiety is connected to $L^2$ via a sulfur atom and q ranges from about 7 to about 9.

In another embodiment, the $V^2$ moiety is connected to $L^2$ via a sulfur atom and q is about 8.

In one embodiment, a compound of formula (III) exists as a mixture of separate compounds.

In one embodiment, a compound of formula (III) exists as a mixture of separate compounds wherein q for three compounds is 1, 2, and 3, respectively.

In one embodiment, a compound of formula (HI) exists as a mixture of separate compounds wherein q for three compounds is 3, 4, and 5, respectively.

In one embodiment, a compound of formula (III) exists as a mixture of separate compounds wherein q for three compounds is 5, 6, and 7, respectively.

In one embodiment, a compound of formula (III) exists as a mixture of separate compounds wherein q for three compounds is 7, 8, and 9, respectively.

In another embodiment, the $V^2$ moiety is connected to $L^2$ via a nitrogen atom of $V^2$.

In yet another embodiment, the $V^2$ moiety is connected to $L^2$ via a carbon atom of $V^2$.

In another aspect of this invention, the $V^2$ moiety includes any unit that causes accumulation of compounds of the invention at the target site or in the vicinity thereof by a mechanism other than binding or reactively associating or complexing with a receptor, antigen, or other receptive moiety associated with a given target site, e.g., a target cell population. One way to achieve this is for example to use a large macromolecule as a $V^2$ moiety, which targets to solid tumor tissue through the enhanced permeability and retention (EPR) effect. Ringsdorf reported use of polymers to target antitumor agents to tumors.[17] Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.

The $V^2$ moiety may for example be a branched or unbranched polymer, such as for example poly[N-(2-hydroxypropyl)methacrylamide](HPMA), poly(2-hydroxyethyl methacrylate) (HEMA), polyglutamic acid or poly-L-glutamic acid (PG), carboxymethyldextran (CMDex), a polyacetal, chitosan, a polypeptide, an oligoethylene glycol or polyethylene glycol (PEG), or a copolymer, such as an HPMA copolymer, an HPMA-methacrylic acid copolymer, a HEMA-methacrylic acid copolymer, a CMDex copolymer, a β-cyclodextrin copolymer, a PEG copolymer, or a poly (lactic-co-glycolic) acid copolymer.[18] In this document both polymer and copolymer are referred to as polymer.

The polymer may be connected to $L^2$ via any suitable functional group, which can be located at one or both ends of the polymer, meaning that in the conjugate q ranges from 1 to 2, or alternatively, the functional groups may (also) be located on groups pendant on the polymer such that $L^2$ is (also) connected to the polymer via these pendant groups with q typically ranging from 1 to about 1000. Optionally, the polymer may also contain an additional targeting group that can bind or reactively associate or complex with a receptive moiety, e.g., an antibody or antibody derivative, bonded to the polymer either via a pendant group or end group, such that improved targeting to the target site is achieved.

Alternatively, the $V^2$ moiety may be a dendrimer or a protein or protein fragment, e.g., albumin, which has no targeting properties except for its ability to accumulate at the target site because of its size or molecular weight.

In one embodiment, the $V^2$ moiety is a polymer.

In another embodiment, the $V^2$ moiety is a polymer and q ranges from 1 to about 1000.

In other embodiments, the $V^2$ moiety is a polymer and q ranges from 1 to about 500 or 400 or 300 or 200 or 100 or less than 100.

In another embodiment, the $V^z$ moiety is a polymer and q ranges from 1 to 2.

In a specific embodiment, the $V^2$ moiety is an oligoethylene glycol or a polyethylene glycol or a derivative thereof.

In another embodiment, the $V^2$ moiety is a dendrimer, a protein, or a protein fragment.

In another embodiment, $V^2$ is absent.

In another embodiment, the $V^2$ moiety is a moiety that is able to transport the conjugate across a biological barrier, e.g., a cell membrane, either with or without prior binding, associating, or complexing with a receptor or receptor complex. In one embodiment, the $V^2$ moiety is a Tat peptide or a derivative, fragment, or analog thereof, or a moiety that has similar transmembrane delivery properties. In another embodiment, the $V^2$ moiety is protein or protein fragment, an antibody or an antibody fragment, a receptor-binding or peptide vector moiety, or a polymeric or dendritic moiety, or any combination thereof, to which is attached a Tat peptide or a derivative, fragment, or analog thereof, or a moiety that has similar transmembrane delivery properties.

Thus, in one aspect of the invention, the moiety $V^2$ is a targeting moiety and is selected from the group consisting of a protein or protein fragment, an antibody or an antibody fragment, a receptor-binding or peptide vector moiety, and a polymeric or dendritic moiety, and any combination thereof.

In another aspect of the invention, the $V^2$ moiety is a moiety that improves the pharmacokinetic properties of a conjugate of the invention. For example, the moiety $V^2$ can be chosen such that the water solubility of the conjugate is (further) improved. This can be achieved by choosing $V^2$ to be a hydrophilic moiety. Alternatively, the $V^2$ moiety can be used to for example increase the residence time of the compound in the circulation, to reduce extravasation and/or excretion, to reduce aggregation, and/or to reduce the immunogenicity of the compound. This may for example be achieved by choosing $V^2$ to be a polyethylene glycol or oligoethylene glycol or derivative thereof. When the moiety $V^2$ is a moiety that improves the pharmacokinetic properties of a compound of the invention and $V^1$ is a moiety that can be cleaved or transformed aspecifically and there are no $V^{1'}$ and $V^{2'}$ moieties, the compound solely serves to improve the (pharmacokinetic) properties of the one or more Z moieties.

In one embodiment, $V^2$ is a moiety that improves the pharmacokinetic properties and $V^1$ is a moiety that can be cleaved or transformed specifically.

In another embodiment, $V^2$ is an oligoethylene glycol or a polyethylene glycol or a derivative thereof and $V^1$ is a moiety that can be cleaved or transformed specifically.

In another embodiment, $V^2$ is a moiety that improves the pharmacokinetic properties and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved by ubiquitous enzymes.

In another embodiment, $V^2$ is an oligoethylene glycol or a polyethylene glycol or a derivative thereof and $V^1$ is a hydrolyzable moiety.

In one aspect of this invention, the $V^2$ moiety is represented by formula (VI):

$$V^{2*}\left(L^{2*}-L^*\left(\begin{matrix}V^{1*}\\|\\Y^*\end{matrix}\right)_{p^*}\right)_{q^*}\right)_{z^*} \quad (VI)$$

wherein $V^{2*}$, $L^{2*}$, $L^*$, $V^{1*}$, $Y^*$, $p^*$, $q^*$, and $z^*$ have the same meaning as $V^2$, $L^2$, $L$, $V^1$, $Y$, $p$, $q$, and $z$, respectively, as defined in this document, except that $Y^*$ is connected to $L^2$. It should be noted that $z^*$ actually equals q. When a compound of formula (III) contains a $V^2$ moiety represented by formula (VI), the one or more $L^2$ moieties are thus connected to $Y^*$. It should be understood that in this document, whenever $V^2$, $L^2$, $L$, $V^1$, $Y$, p, q, or z is mentioned, the same can apply for each $V^{2*}$, $L^{2*}$, $L^*$, $V^{1*}$, $Y^*$, $p^*$, $q^*$, or $z^*$, respectively.

Use of a $V^2$ moiety of formula (VI) in a conjugate of formula (III) implicates that two conditionally-cleavable or conditionally-transformable moieties may be present in the same promoiety, and therefore two separate cleavages/transformations may be required to completely remove the promoiety. The requirement that two different conditions need to have been met before one or more Z are released might favorably affect the properties of the conjugate. For instance, it may increase the targeting efficiency of the conjugate. The two transformations/cleavages may occur at different extracellular/intracellular locations. The moiety to be removed by the second cleavage or as a consequence of the second transformation may be used in this instance to help transport Z from a first extracellular or intracellular location to a second extracellular or intracellular location.

It will be apparent that a $V^2$ moiety of formula (VI) cannot only be useful in conjugates of a compound of formula (I) or (II), but may be used in similar conjugates of other therapeutic agents, diagnostic moieties, and the like.

It should be understood that the functional moiety $V^2$ can have several functional properties combined. For example, $V^2$ can be a moiety that improves the pharmacokinetic properties of a compound of this invention and at the same time be or contain a targeting moiety.

Conjugates of this invention may contain one or more promoieties. These promoieties may be the same or different. The presence of two or more promoieties may favorably affect the properties of the conjugate. For instance, it may improve the water solubility and/or increase the targeting efficiency of the conjugate. In one embodiment, when there are two or more promoieties, said promoieties are different from each other. The two or more different promoieties may have different functions and may be removed under different conditions and at different extracellular/intracellular locations.

In one embodiment, there is one promoiety linked to Z.

In another embodiment, there is one promoiety linked to Z via $X^1$.

In another embodiment, there are two promoieties linked to Z.

In another embodiment, there are two promoieties linked to Z, of which one is connected via $X^1$.

In yet another embodiment, there are three promoieties linked to Z.

In yet another embodiment, there are three promoieties linked to Z, of which one is connected via $X^1$.

In one embodiment, a compound of formula (III) is represented by a compound of formula (III-1) or (III-2):

-continued

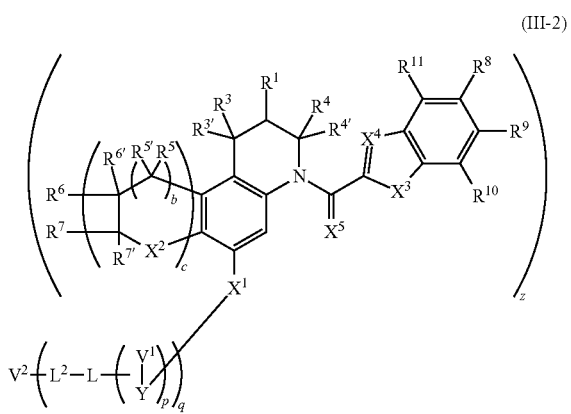
(III-2)

In another embodiment, a compound of formula (III) is represented by a compound of formula (III-3) or (III-4):

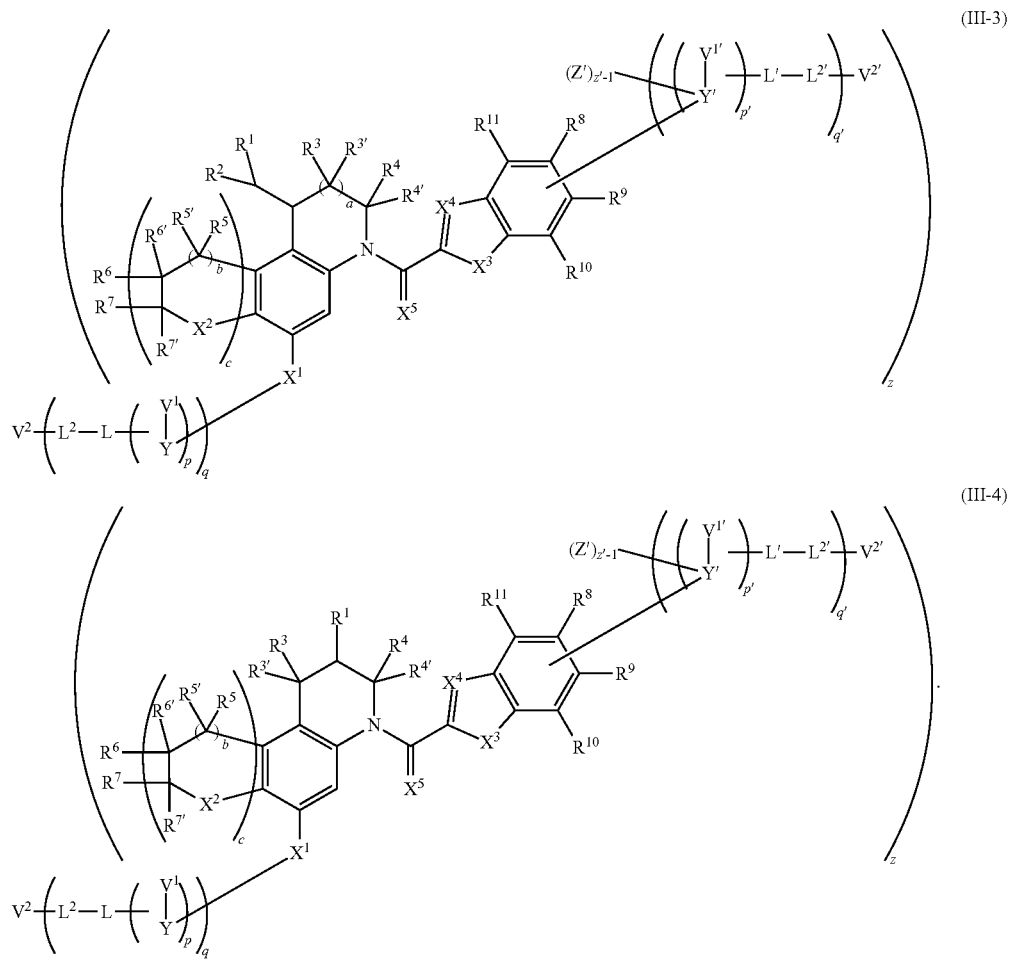
(III-3)

(III-4)

wherein Y' is connected to an atom being part of $R^8$, $R^9$, $R^{10}$, or $R^{11}$.

In one embodiment, p is an integer from 1 (included) to 128 (included). In another embodiment, q is an integer from 1 (included) to 1000 (included). In other embodiments, p is an integer from 1 (included) to 64 (included) or 32 (included) or 16 (included) or 8 (included) or 4 (included) or 2 (included). In other embodiments, q is an integer from 1 (included) to 500 (included) or 400 (included) or 300 (included) or 200 (included) or 100 (included) or 16 (included) or 8 (included) or 6 (included) or 4 (included) or 2 (included).

In one embodiment, if more than 1 promoiety is connected to a first Z and in one of the promoieties there is more than one attachment site for Z moieties, then the other ones of said promoieties connected to said first Z each contain a single attachment site for a Z moiety.

In one embodiment, a compound of formula (III) is represented by

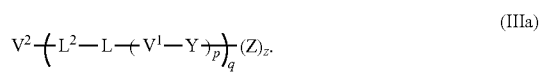
(IIIa)

In one embodiment, p in a compound of formula (IIIa) is 1.

In another embodiment, in a compound of formula (IIIa) p is 1 and z equals q.

In another embodiment, a compound of formula (IIIa) is represented by

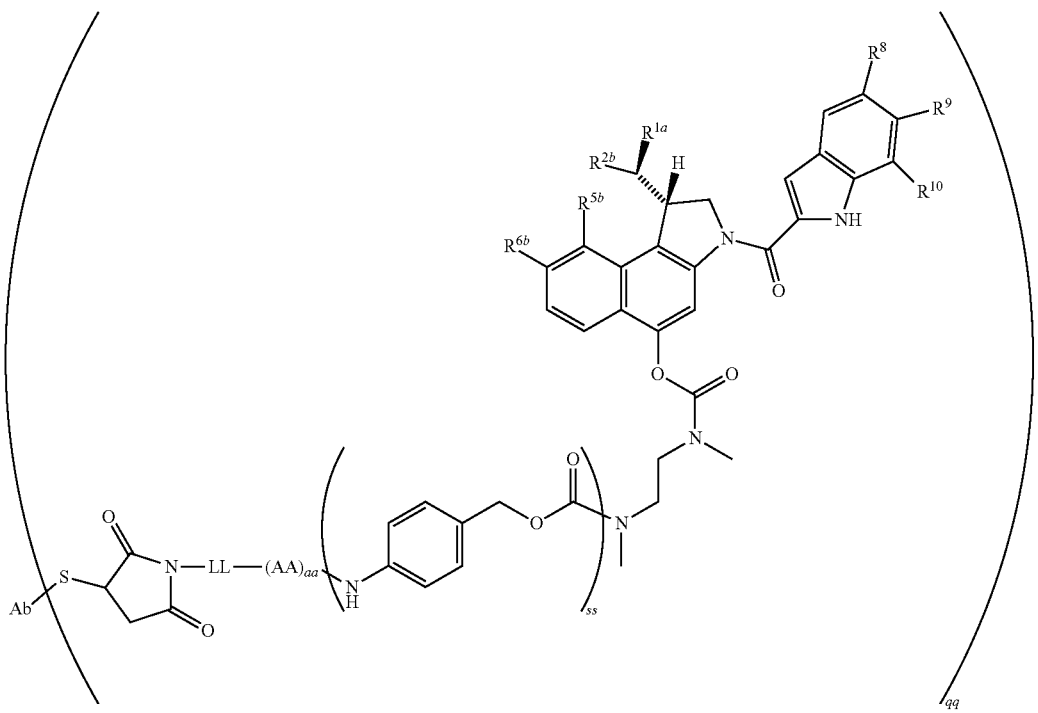

or by an isomer, or by a mixture of isomers, wherein $R^{1a}$, $R^{2b}$, $R^{5b}$, $R^{6b}$, $R^8$, $R^9$, and $R^{10}$ are as previously defined, $(AA)_{aa}$, is selected from valylcitrulline, valyllysine, phenylalanyllysine, alanylphenylalanyllysine, and D-alanylphenylalanyllysine, ss is 1 or 2, LL is selected from

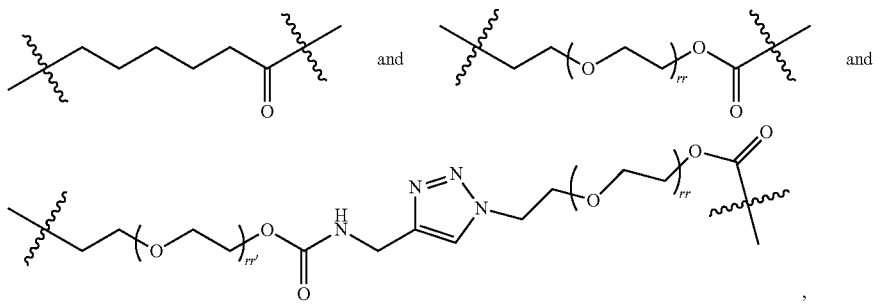

qq ranges from 1 to 20, rr and rr' each independently range from 1 to 4, and Ab is an antibody or a fragment or derivative thereof.

In another embodiment, a compound of formula (III) is represented by

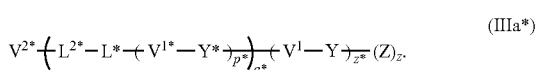
(IIIa*)

In one embodiment, p* in a compound of formula (IIIa*) is 1.

In another embodiment, in a compound of formula (IIIa*) p* is 1 and z* equals q*.

In another embodiment, a compound of formula (III) is represented by

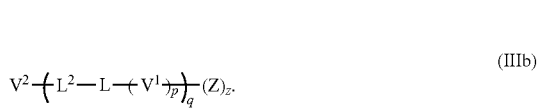
(IIIb)

In one embodiment, p in a compound of formula (IIIb) is 1.

In another embodiment, a compound of formula (III) is represented by

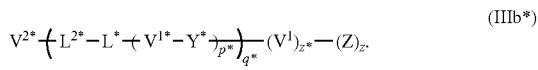
(IIIb*)

In one embodiment, p* in a compound of formula (IIIb*) is 1.

In another embodiment, in a compound of formula (IIIb*) p* is 1 and z* equals q*.

In another embodiment, $V^1$ in a compound of formula (IIIb*) is an enzyme-cleavable substrate. In a further embodiment, $V^1$ can be cleaved by an intracellular enzyme.

In another embodiment, $V^1$ is an optionally substituted N,N-dialkylaminocarbonyl group wherein the two alkyl groups may be the same or different and optionally be connected to each other to form an optionally substituted heterocycle. In yet another embodiment, $V^1$ is piperazinocarbonyl.

In another embodiment, a compound of formula (IIIb*) is represented by

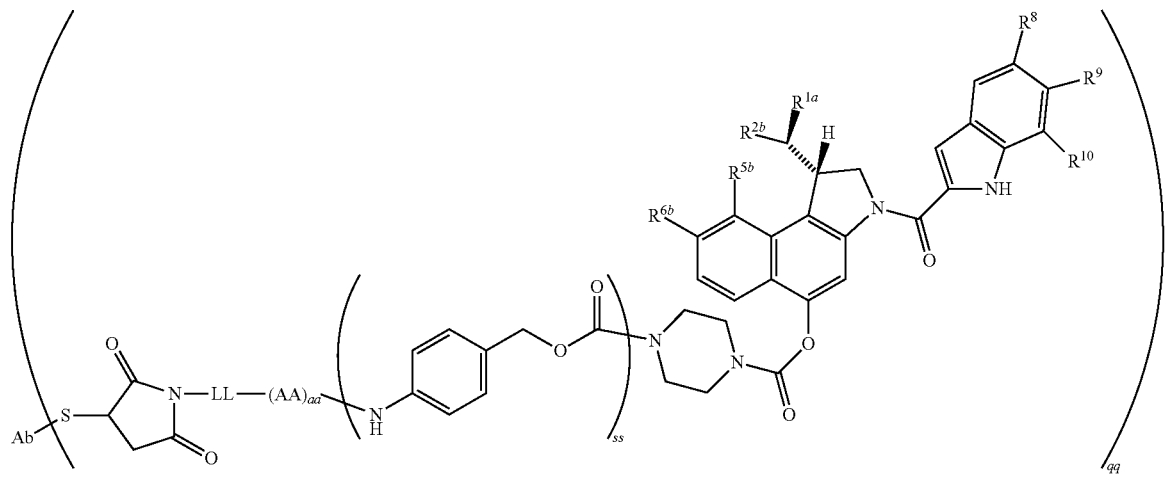

or by an isomer, or by a mixture of isomers, wherein $R^{1a}$, $R^{2b}$, $R^{5b}$, $R^{6b}$, $R^8$, $R^9$, and $R^{10}$ are as previously defined, $(AA)_{aa}$ is selected from valylcitrulline, valyllysine, phenylalanyllysine alanylphenylalanyllysine, and D-alanylphenylalanyllysine, ss is 1 or 2, LL is selected from

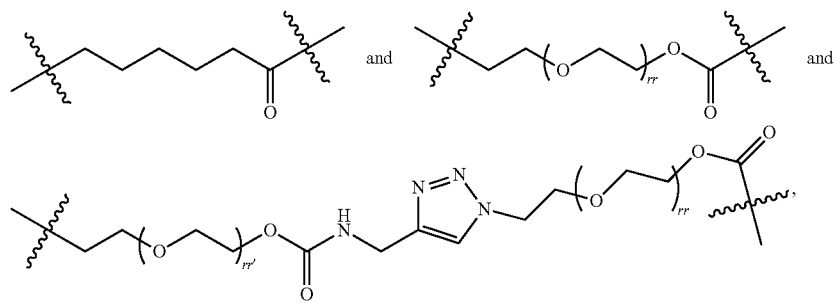

qq ranges from 1 to 20, rr and rr' each independently range from 1 to 4, and Ab is an antibody or a fragment or derivative thereof.

In another embodiment, a compound of formula (III) is represented by $$V^2 \text{---} (L^2 \text{---} L \text{---} V^1 \text{---} Z)_q. \quad \text{(IIIc)}$$

In yet another embodiment, a compound of formula (III) is represented by $$V^1 \text{---} Z \quad \text{(IIId).}$$

In one embodiment, a compound of formula (IIId) is represented by

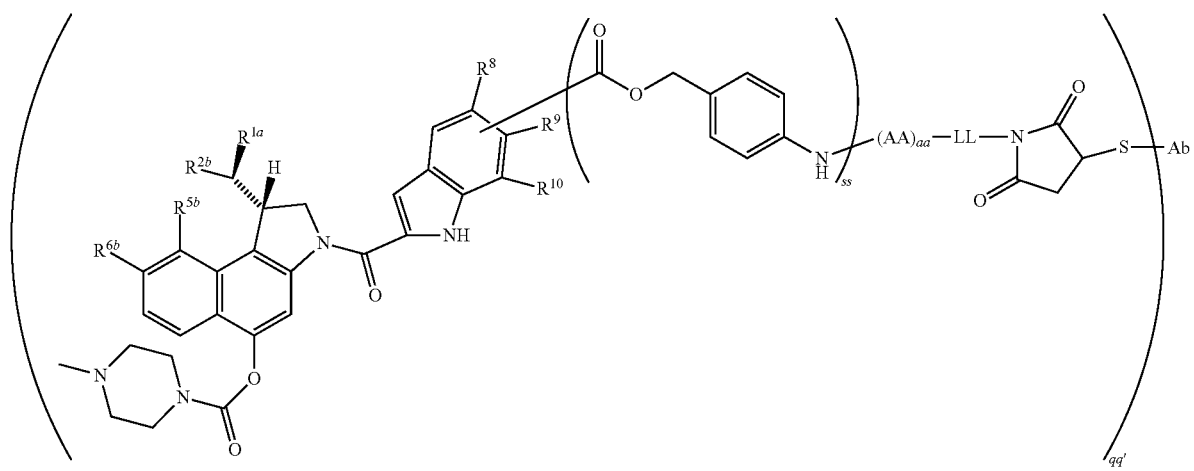

or by an isomer, or by a mixture of isomers, wherein $R^{1a}$, $R^{2b}$, $R^{5b}$, $R^{6b}$, $R^8$, $R^9$, and $R^{10}$ are as previously defined, ss is 0, 1, or 2, $(AA)_{aa}$ is selected from valylcitrulline, valyllysine, phenylalanyllysine, alanylphenylalanyllysine, and D-alanylphenylalanyllysine, the p-aminobenzyloxycarbonyl group—or the $(AA)_{aa}$ group if ss is 0—is connected to an oxygen, sulfur, or nitrogen atom in $R^8$, $R^9$ or $R^{10}$, LL is selected from

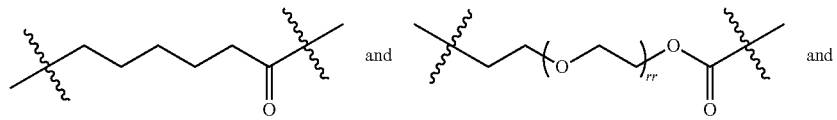

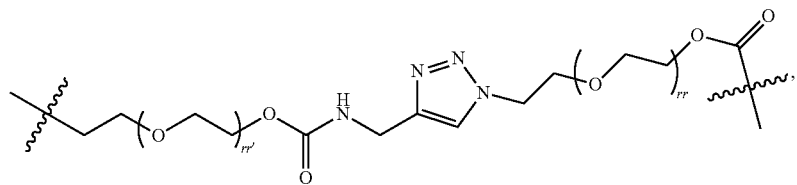

qq' ranges from 1 to 20, rr and rr' each independently range from 1 to 4, and Ab is an antibody or a fragment or derivative thereof.

In yet another embodiment, a compound of formula (III) is represented by $$V^2-L^2-L-Z \quad (IIIe).$$

In one embodiment, a compound of formula (IIIe) is represented by

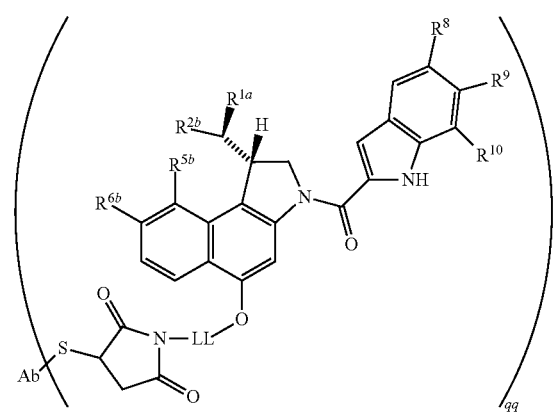

or by an isomer, or by a mixture of isomers, wherein $R^{1a}$, $R^{2b}$, $R^{5b}$, $R^{6b}$, $R^8$, $R^9$, and $R^{10}$ are as previously defined, $(AA)_{aa}$ is selected from valylcitrulline, valyllysine, phenylalanyllysine, alanylphenylalanyllysine, and D-alanylphenylalanyllysine, LL is selected from

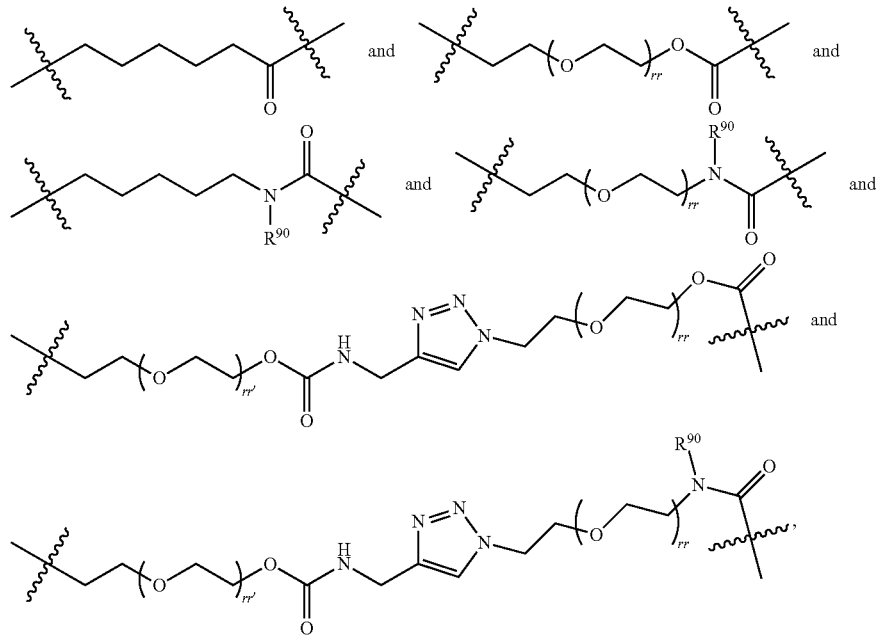

qq ranges from 1 to 20, rr and rr' each independently range from 1 to 4, $R^{90}$ is selected from H and $C_{1-3}$ alkyl, and Ab is an antibody or a fragment or derivative thereof.

In another embodiment, a compound of formula (IIIe) is represented by

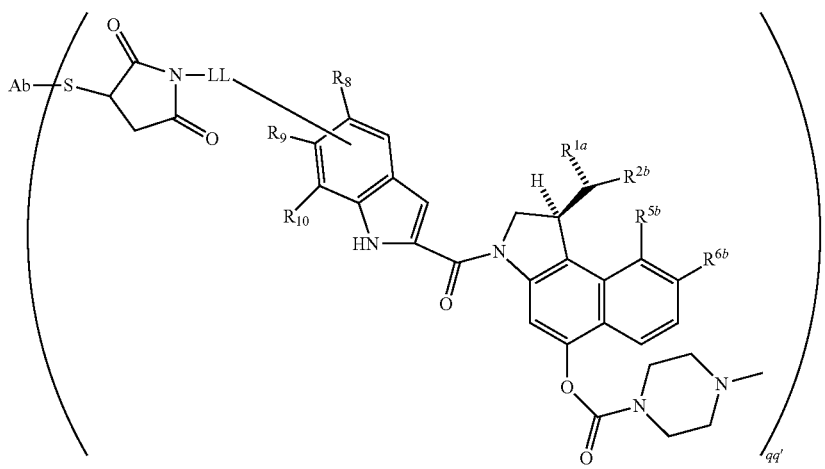

or by an isomer, or by a mixture of isomers, wherein $R^{1a}$, $R^{2b}$, $R^{5b}$, $R^{6b}$, $R^8$, $R^9$, and $R^{10}$ are as previously defined, (AA), is selected from valylcitrulline, valyllysine, phenylalanyllysine, alanylphenylalanyllysine, and D-alanylphenylalanyllysine, LL is connected to an oxygen, sulfur, or nitrogen atom in $R^8$, $R^9$ or $R^{10}$, LL is selected from

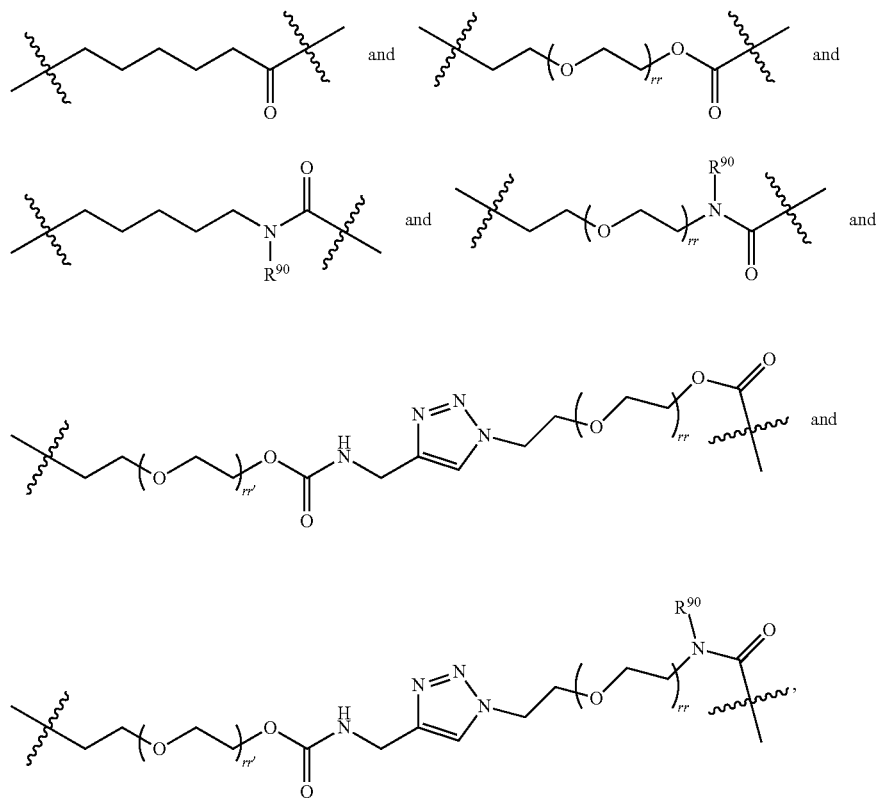
qq' ranges from 1 to 20, rr and rr' each independently range from 1 to 4, $R^{90}$ is selected from H and $C_{1-3}$ alkyl, and Ab is an antibody or a fragment or derivative thereof.
In one embodiment, a compound of formula (III) is represented by
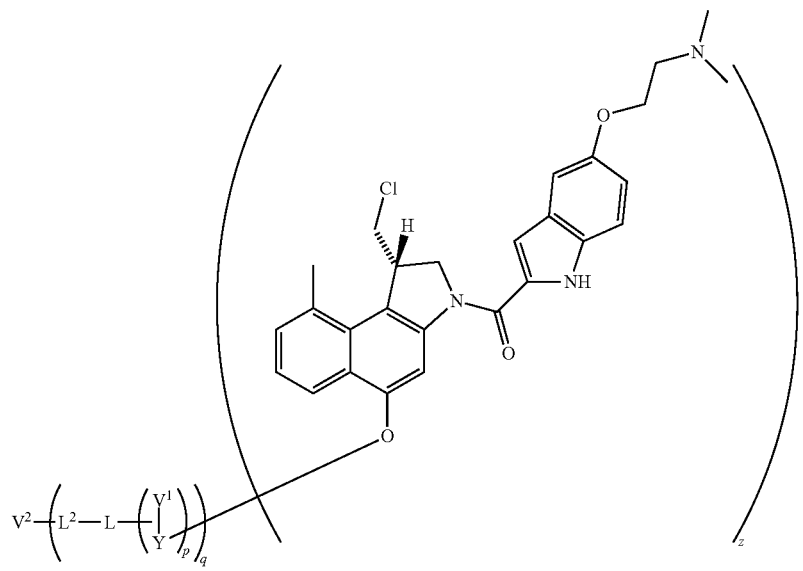
or by an isomer, or by a mixture of isomers.
In another embodiment, a compound of formula (III) is represented by

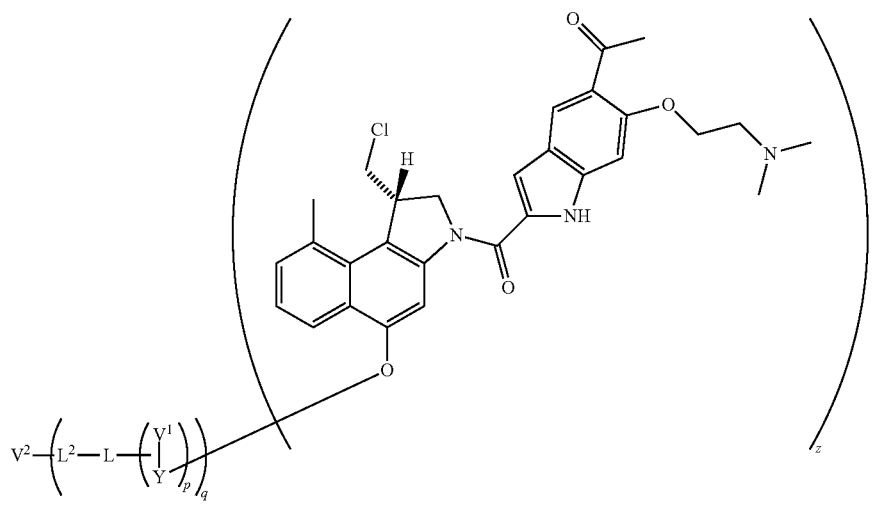
or by an isomer, or by a mixture of isomers.
In another embodiment, a compound of formula (III) is represented by
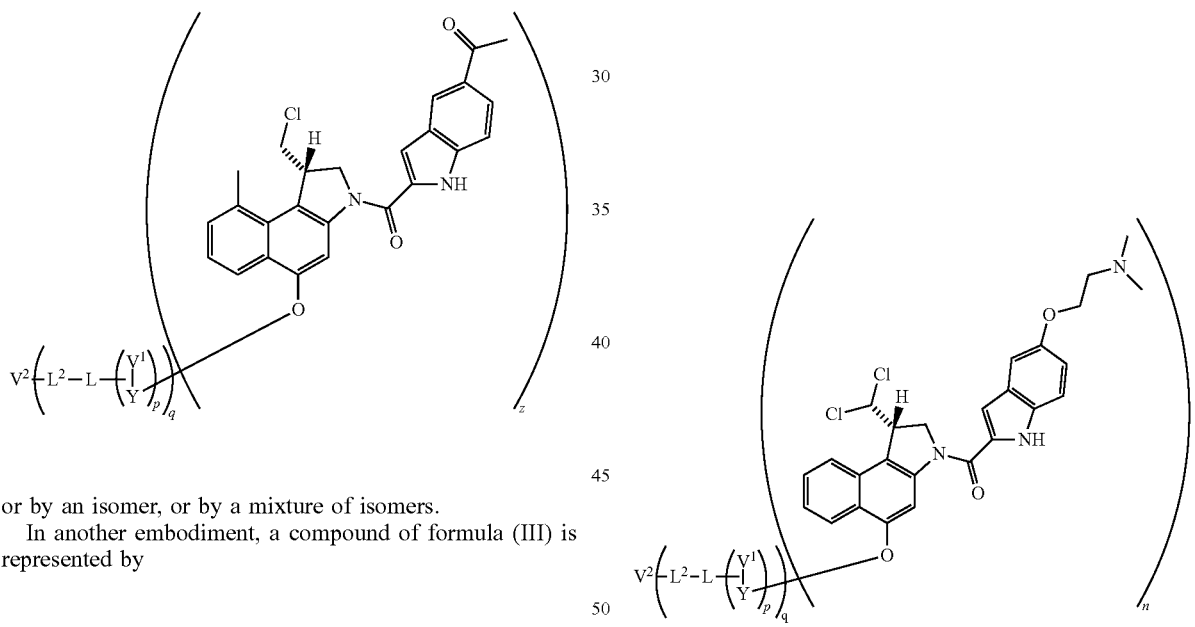
or by an isomer, or by a mixture of isomers.
In another embodiment, a compound of formula (III) is represented by
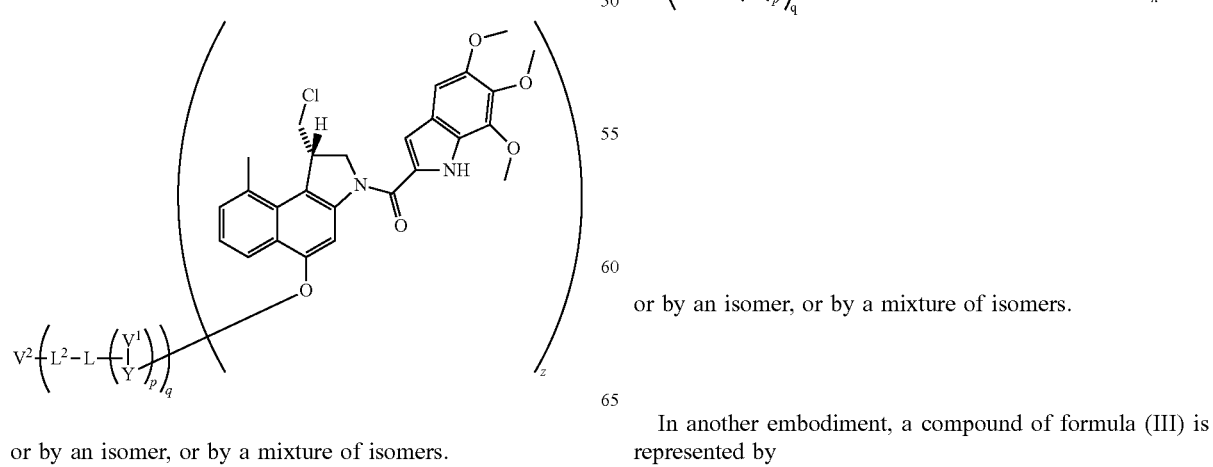
or by an isomer, or by a mixture of isomers.
In another embodiment, a compound of formula (III) is represented by

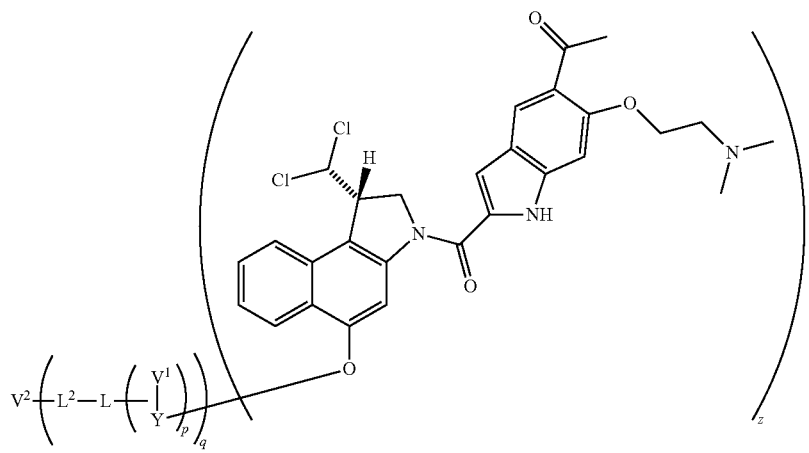

or by an isomer, or by a mixture of isomers.

In another embodiment, a compound of formula (III) is represented by

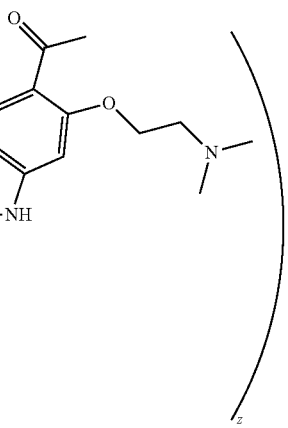

or by an isomer, or by a mixture of isomers.

In another embodiment, a compound of formula (III) is represented by

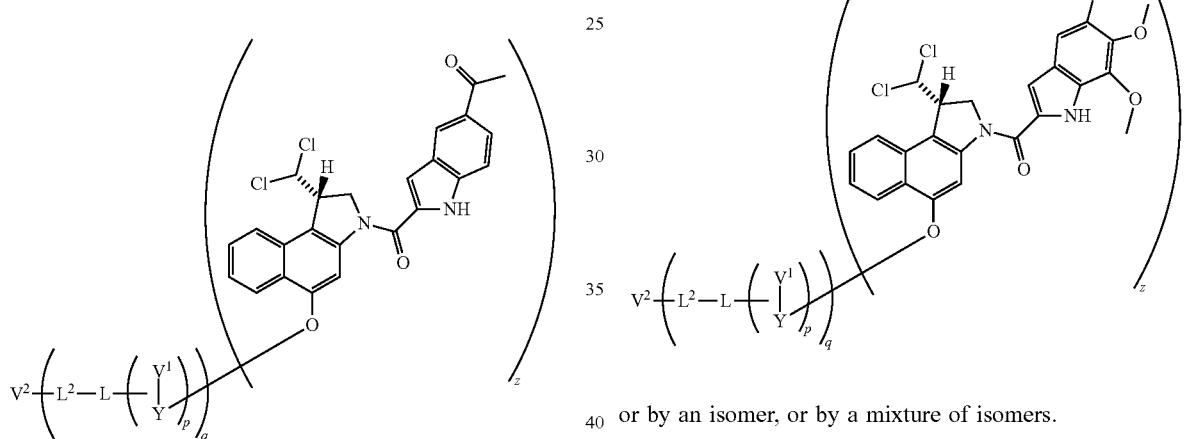

or by an isomer, or by a mixture of isomers.

In another embodiment, a compound of this invention is represented by

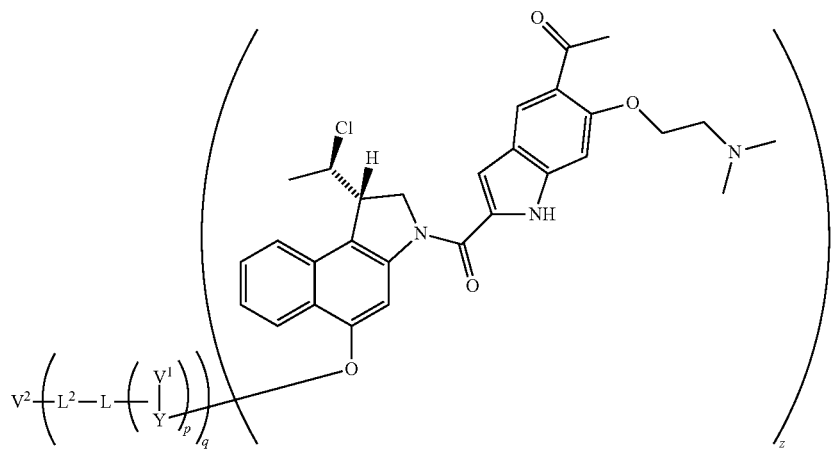

or by an isomer, or by a mixture of isomers.

In another embodiment, a compound of this invention is represented by

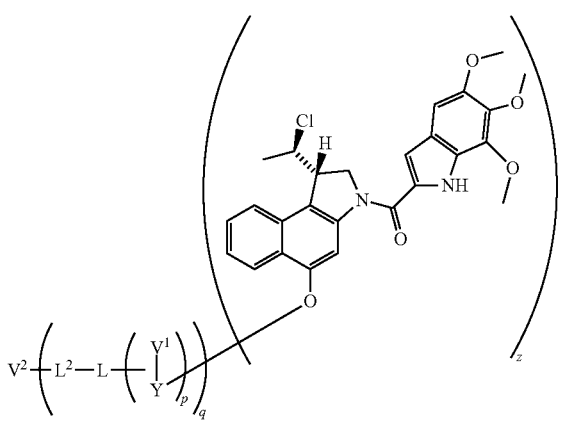

or by an isomer, or by a mixture of isomers.

In another embodiment, a compound of this invention is represented by

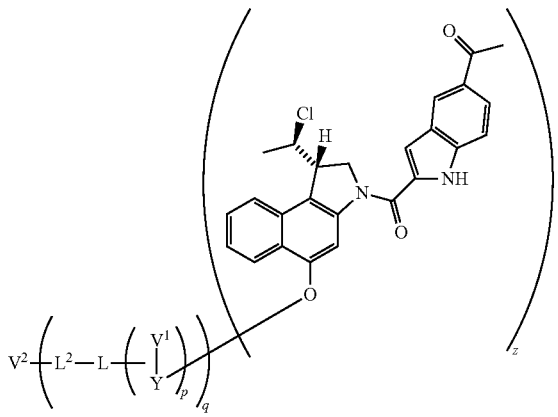

or by an isomer, or by a mixture of isomers.

Synthesis of Compounds of the Invention

As described in somewhat more detail below, compounds of formulae (I)-(IV) can be conveniently prepared in a way for some part analogous to compounds reported in WO 01/83448, WO 2004/043493, and WO 02/083180.

In one embodiment, a compound of formula (I) or (II) is used to prepare a compound of formula (III). In another embodiment, a compound of formula (I) or (II) is used to prepare a compound of formula (IV). In another embodiment, a compound of formula (IV) is used to prepare a compound of formula (III). In another embodiment, a compound of formula (III) wherein $V^1$ is a protecting group is used to prepare another compound of formula (III) wherein $V^1$ is an in vivo removable moiety.

Figure 2:
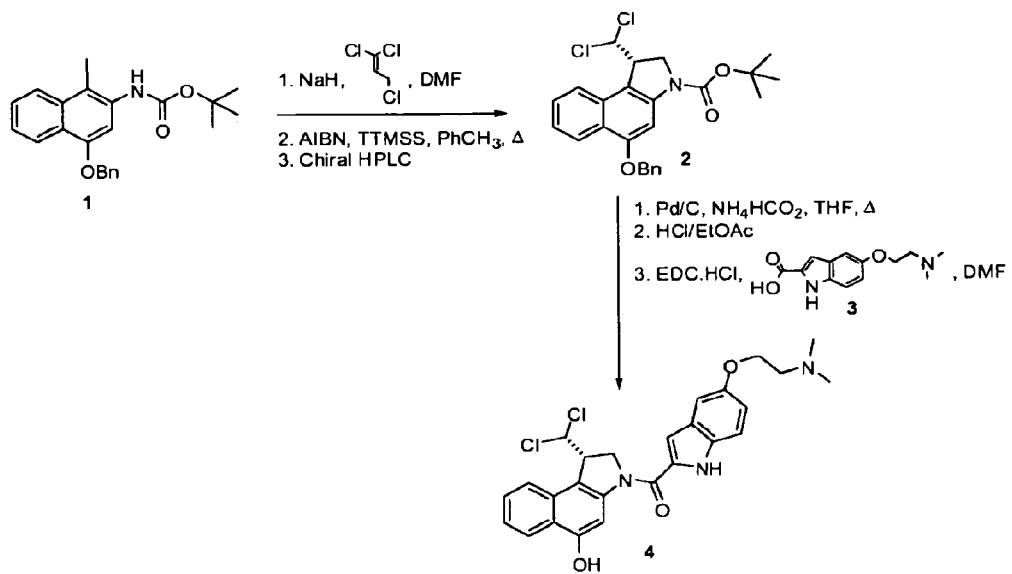
FIG. 2 illustrates the preparation of agent 4 from compound 1.

Several agents have been prepared in good yields. For example, agent 4 was prepared in 6 steps from naphthalene 1, as depicted in FIG. 2. Alkylation of 1 followed by a radical cyclization step provided racemic 2. The enantiomers were then separated on a Chiralpak IA HPLC column. As there is only one chiral center in compound 2, the theoretical yield with which each enantiomer can be obtained after the radical cyclization step amounts to 50%, which is twice as much as the maximum yield for similar enantiopure compounds containing two different substituents on the carbon bearing the leaving group, as for example compound 5 in FIG. 3.

Removal of the benzyl protecting group in 2 with palladium and ammonium formate as the hydrogen donor, subsequent removal of the tert-butyl protecting group, and final coupling to indole 3 afforded agent 4 in good yield.

Figure 3:
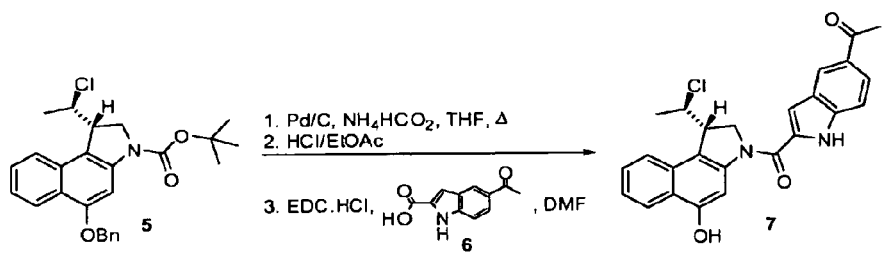
FIG. 3 depicts the synthesis of agent 7 from compound 5.
Figure 4:
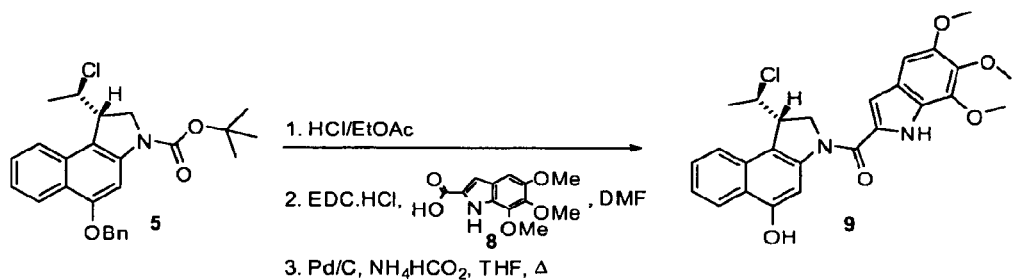
FIG. 4 shows the preparation of agent 9 from compound 5.

Agent 7 was prepared from 5 according to a similar process using indole 6 (FIG. 3). Compound 9 was prepared from 5 using a slightly different approach (FIG. 4). The benzyl protecting group was only removed after coupling of indole 8 to deprotected 5.

Figure 5:
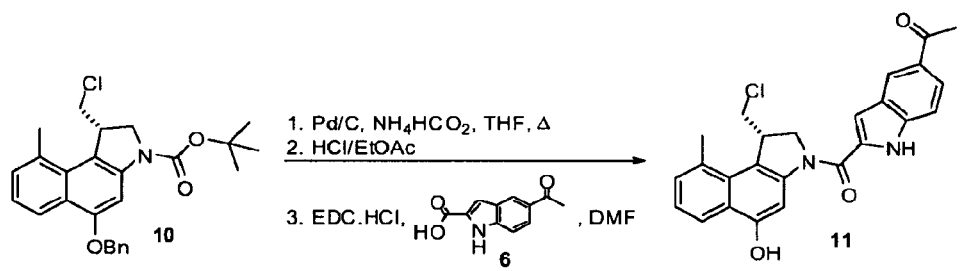
FIG. 5 illustrates the synthesis of agent 11 from compound 10.
Figure 6:
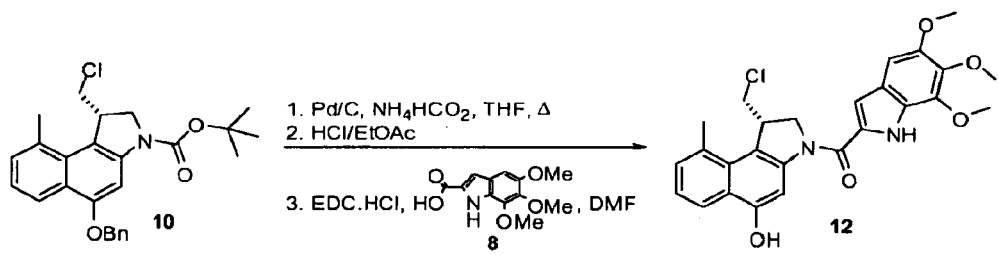
FIG. 6 depicts the preparation of agent 12 from compound 10.

Agents 11 (FIG. 5) and 12 (FIG. 6) were synthesized from 10 and indoles 6 and 8, respectively, in a manner largely analogous to the preparation of 7 from 5.

Figure 7:
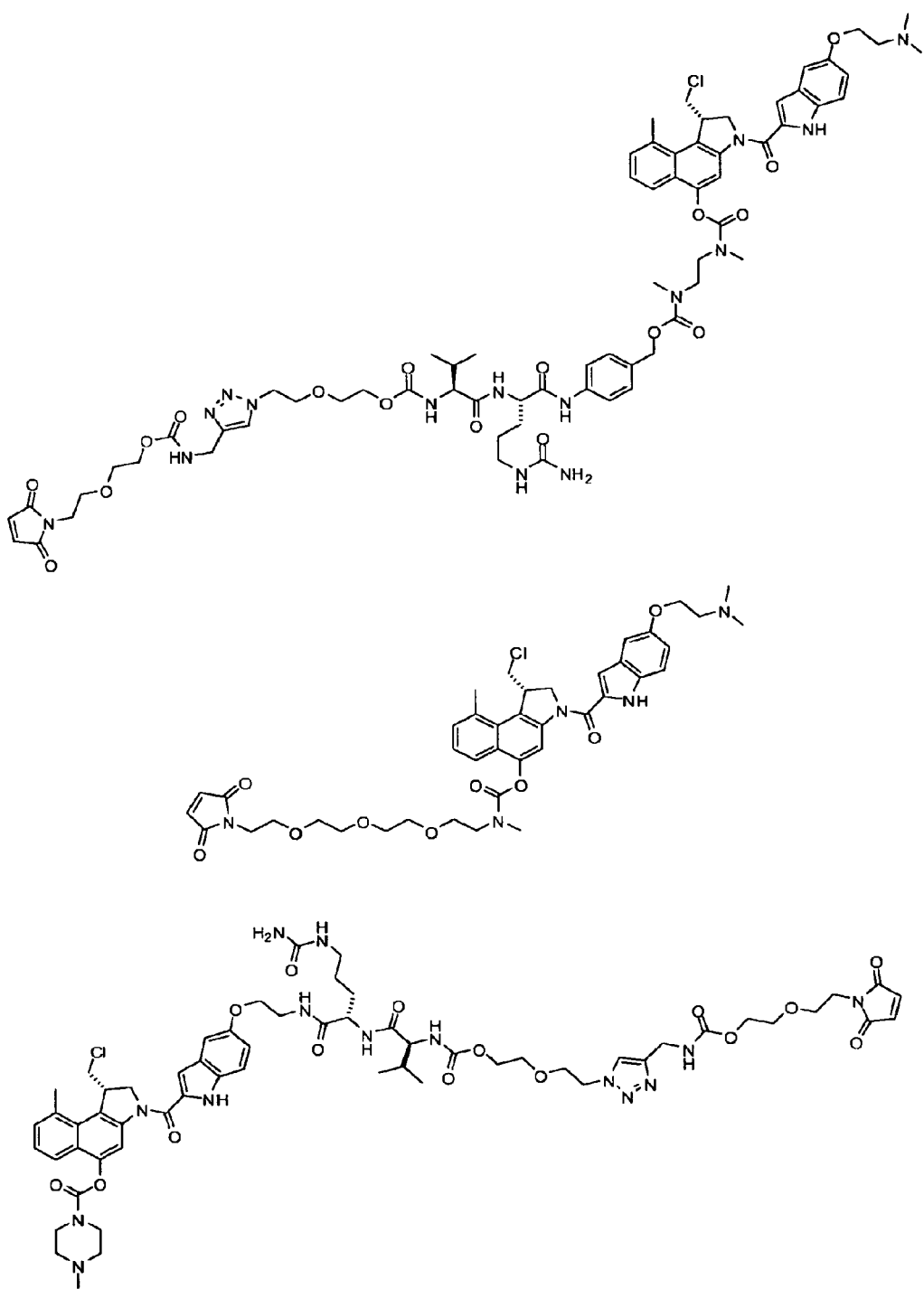
FIG. 7 provides some exemplary structures of linker-agent conjugates.
Figure 7:
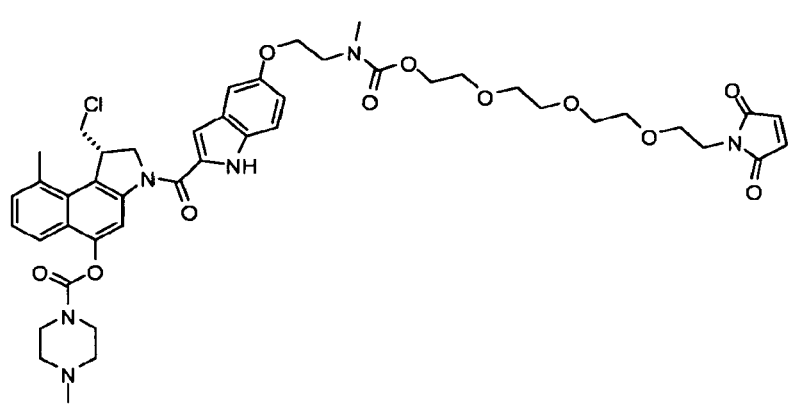

Agents such as 4, 7, 9, 11, and 12 can be incorporated into linker-drug conjugates and conjugates following established procedures. Some exemplary structures of linker-agent conjugates have been depicted in FIG. 7.

Uses, Methods, and Compositions

In one aspect, this invention relates to use of a compound of formula (I) or (II) for the preparation of a compound of formula (III).

In another aspect, this invention relates to use of a compound of formula (IV) for the preparation of a compound of formula (III).

In yet another aspect, this invention relates to use of a compound of formula (I) or (II) for the preparation of a compound of formula (IV).

In yet another aspect, this invention relates to use of a compound of formula (III) wherein $V^1$ is a protecting group for the preparation of another compound of formula (III) wherein $V^1$ is an in vivo removable moiety.

In yet another aspect, the invention relates to the use of any of the compounds defined above for the manufacture of a pharmaceutical composition for the treatment of a mammal being in need thereof.

In one embodiment, the invention relates to the use of any of the compounds defined above for the manufacture of a pharmaceutical composition for the treatment of a tumor in a mammal.

The invention also relates to any of the compounds defined above as a medicament or an active component or active substance in a medicament.

In a further aspect, the invention relates to a process for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one embodiment, a compound of the invention is used to treat an illness characterized by undesired proliferation. In another embodiment, a compound of the invention is used to treat an illness characterized by undesired cell proliferation. In another embodiment, a compound of the invention is used to treat a tumor. In yet another embodiment, a compound of the invention is used to treat an inflammatory disease. In yet another embodiment, a compound of the invention is used to treat an autoimmune disease. In yet another embodiment, a compound of the invention is used to treat a bacterial or microbial infection.

In a further embodiment, this invention relates to a method of treating a mammal having an illness characterized by undesired (cell) proliferation with a compound of this invention. In another embodiment, this invention relates to a method of treating a mammal carrying a tumor with a compound of this invention. In yet another embodiment, this invention relates to a method of treating a mammal having an inflammatory disease with a compound of this invention.

In yet another embodiment, this invention relates to a method of treating a mammal having an autoimmune disease with a compound of this invention. In yet another embodiment, this invention relates to a method of treating a mammal having a bacterial or microbial infection with a compound of this invention.

In a further embodiment, the invention relates to a method of treating a mammal being in need thereof, whereby the method comprises the administration of a pharmaceutical composition comprising a compound of this invention to the mammal in a therapeutically effective dose.

In one embodiment, the invention relates to a method of treating or preventing a tumor in a mammal, whereby the method comprises the administration of a pharmaceutical composition comprising a compound of this invention to the mammal in a therapeutically effective dose.

In another embodiment, the invention relates to a method of treating or preventing an inflammatory disease in a mammal, whereby the method comprises the administration of a pharmaceutical composition comprising a compound of this invention to the mammal in a therapeutically effective dose.

In another embodiment, the invention relates to a method of treating or preventing an autoimmune disease in a mammal, whereby the method comprises the administration of a pharmaceutical composition comprising a compound of this invention to the mammal in a therapeutically effective dose.

In another embodiment, the invention relates to a method of treating or preventing a bacterial or microbial infection in a mammal, whereby the method comprises the administration of a pharmaceutical composition comprising a compound of this invention to the mammal in a therapeutically effective dose.

The invention also relates to pharmaceutical compositions comprising the compounds of the invention as defined above. A compound of the invention may be administered in purified form together with a pharmaceutical carrier as a pharmaceutical composition. The preferred form depends on the intended mode of administration and therapeutic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the invention. Such physiologically acceptable compounds include, for example, carbohydrates, such as glucose, sucrose, or dextrans, antioxidants, such as ascorbic acid or glutathione, chelating agents, low molecular weight proteins, or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions.

Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion, or other known desirable features are red iron oxide, silica gel, sodium lauryl sulfate, titanium dioxide, edible white ink, and the like. Similar diluents can be used to make compressed tablets. Both tablets and capsules can be manufactured as sustained release products to provide for continuous release of medication over a period of hours.

Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science[19].

A compound of the invention may also be used in combination therapy, in which a compound of this invention is used in combination with one or more other therapeutic agents. Combination of two or more therapeutics may favorably affect treatment outcome. The agents may be administered either sequentially or concomitantly. Therefore, in one embodiment this invention relates to use of a compound of this invention or a pharmaceutical composition comprising a compound of this invention in combination therapy.

The invention is further exemplified by the following examples. These examples are for illustrative purposes only and are not intended to limit the scope of the invention.

EXAMPLES

Example 1

Preparation of Compound 2 from Compound 1

To a suspension of NaH (0.50 g, 12.5 mmol) in DMF (30 ml) was added a solution of compound 1 (2.38 g, 5.00 mmol) in DMF (20 ml) and the mixture was stirred for 1 h. Then, 1,1,3-trichloroprop-1-ene (1.02 g, 7.00 mmol) was added and the mixture was stirred for 2.5 h. A saturated aqueous solution of $NH_4Cl$ (100 mL) was slowly added and the mixture was extracted twice with ethyl acetate. The combined organics were washed with water and brine, dried over $Na_2SO_4$, filtered, and concentrated. Column chromatography (heptanes/EtOAc, 6:1 to 3:1) gave the alkylated product (2.43 g, 4.15 mmol, 83%) as an orange foam. The alkylated product (2.42 g, 4.14 mmol) was dissolved in toluene (60 ml) and the solution was heated to 80° C. AIBN (0.170 g, 1.035 mmol) and TTMSS (1.132 g, 4.55 mmol) were then added and the mixture was stirred at 80° C. for 5 h. Then, the mixture was cooled to RT, water was added, the layers were separated, and the aqueous layer extracted with ethyl acetate. The combined organic layers were dried over $Na_2SO_4$, filtered, and concentrated. Crystallization from heptane gave a mixture of enantiomers (1.423 g, 3.11 mmol, 75%) as a slightly brown solid. Separation of the enantiomers was carried out using a Chiralpak IA HPLC column to afford compound 2 with high enantiopurity. —$^1$H NMR (300 MHz, $CDCl_3$), δ (ppm): 1.61 (9H, s, t-butyl), 4.20 (1H, m, H-2), 4.35 (1H, m, H-2), 4.48 (1H, m, H-1), 5.25 (2H, s, Bn), 6.33 (1H, d, J=2.1 Hz, H-10), 7.32-7.55 (8H, m, H-7, H-8, H-9, Bn), 7.88 (1H, br. s, H-4), 8.30 (1H, d, J=8.4 Hz, H-6).

Example 2

Preparation of Agent 4 from Compound 2

A solution of compound 2 (74 mg, 0.161 mmol) in THF (5 ml) was warmed to 45° C., after which palladium (10% on carbon, 34.4 mg, 0.032 mmol) and ammonium formate (25% aqueous solution, 406 mg, 1.61 mmol) were added. The mixture was stirred for 2.5 h, cooled to RT, and filtered over Celite. The filtrate was concentrated and purified by column chromatography to yield the debenzylated intermediate (60 mg, 0.163 mmol) as a white semi-solid. This intermediate (45 mg, 0.122 mmol) was dissolved in 4 N HCl in ethyl acetate (6 ml) and the solution was stirred for 2 h. Then, the mixture was concentrated and dried in vacuo. The crude product was dissolved in dry DMF (4 ml) and the solution was cooled to 0° C. Indole 3 (45.2 mg, 0.159 mmol) and EDC.HCl (70.3 mg, 0.367 mmol) were added. The mixture was stirred at RT for 18 h and then concentrated. The crude product was purified by column chromatography (DCM/MeOH, 19:1, 0.05% conc. HCl) to yield 4 (65 mg, 0.122 mmol, 99%) as a pale yellow solid. —$^1$H NMR (300 MHz, $CDCl_3/CD_3OD$), δ (ppm): 3.02 (6H, br. s, $N(CH_3)_2$), 3.54-3.63 (2H, m, H-2"), 4.42-4.53 (3H, m, H-1, H-1"), 4.76 (1H, t, J=7.5 Hz, H-2), 5.03 (1H, d, J=8.1 Hz, H-2), 6.36 (1H, br. s, H-10), 7.04-7.12 (2H, m, H-3', H-6'), 7.24 (1H, br. s, H-4'), 7.40-7.70 (2H, m, H-8, H-7'), 7.56 (1H, t, J=6.0 Hz, H-7), 7.66 (1H, d, J=6.3 Hz, H-9), 7.82 (1H, br. s, H-4), 8.30 (1H, d, J=6.0 Hz, H-6); MS (ESI) m/z=498 (M+H$^+$).

Example 3

Preparation of Agent 7 from Compound 5

A solution of compound 5 (54 mg, 0.123 mmol) in THF (7 ml) was warmed to 45° C., after which palladium (10% on carbon, 96 mg, 0.090 mmol) and ammonium formate (25% aqueous solution, 310 mg, 1.23 mmol) were added. The mixture was stirred for 0.5 h, cooled to RT, and filtered over Celite. The filtrate was concentrated and purified by column chromatography to yield the debenzylated intermediate (41 mg, 0.118 mmol) as a white semisolid. This intermediate (45 mg, 0.122 mmol) was dissolved in 4 N HCl in ethyl acetate (5 ml) and the resultant solution was stirred for 2 h. Then, the mixture was concentrated and dried in vacuo. The crude product was dissolved in dry DMF (6 ml) and the solution was cooled to 0° C. Indole 6 (35.0 mg, 0.172 mmol) and EDC.HCl (66.1 mg, 0.345 mmol) were added. The mixture was stirred at RT for 18 h and then concentrated. The crude product was purified by column chromatography (DCM/MeOH, 19:1, 0.05% conc. HCl) to yield 7 (23 mg, 0.053 mmol, 46%) as a pale yellow solid. —$^1$H NMR (300 MHz, $CDCl_3/CD_3OD$), δ (ppm): 1.61 (3H, d, J=8.0 Hz, 10-$CH_3$), 2.66 (3H, s, Ac), 3.96 (1H, m, H-1), 4.51-4.63 (2H, m, H-2, H-10), 4.77 (1H, d, J=12.0, H-2), 7.20 (1H, s, H-3'), 7.36 (1H, t, J=8.0 Hz, H-7), 7.46-7.52 (2H, m, H-8, H-9), 7.66 (1H, d, J=8.0 Hz, H-7'), 7.75 (1H, br. s, H-4), 7.93 (1H, dd, H-6'), 8.24 (1H, d, J=8.0 Hz, H-6), 8.40 (1H, s, H-4'); MS (ESI) m/z=433 (M+H$^+$).

Example 4

Preparation of Agent 9 from Compound 5

Compound 5 (80 mg, 0.183 mmol) was dissolved in 4 N HCl in EtOAc (8 ml). The solution was stirred for 1 h and then concentrated. The crude product was dried and then dissolved in dry DMF (4 ml). The solution was cooled to 0 OC and 8 (45.9 mg, 0.183 mmol) and EDC.HCl (105 mg, 0.548 mmol) were added. The mixture was stirred at RT for 18 h and then concentrated. The crude product was purified by column chromatography (DCM/EtOAc, 19:1) to yield the benzyl-protected agent (65 mg, 0.114 mmol, 62%) as a white solid. A solution of this intermediate (65 mg, 0.114 mmol) in THF (5 ml) was warmed to 45° C., palladium (10% on carbon, 24 mg, 0.226 mmol) and ammonium formate (25% aqueous solution, 288 mg, 1.14 mmol) were added, and the resultant mixture was stirred for 2 h. The mixture was cooled to RT and filtered over Celite. The filtrate was concentrated and the crude product purified by column chromatography (DCM/MeOH, 19:1, 0.1% HCl) to yield 9 (44 mg, 0.091 mmol, 80%) as a pale yellow solid. —$^1$H NMR (300 MHz, $CDCl_3$), δ (ppm): 1.60 (3H, d, J=6.6 Hz, 10-$CH_3$), 3.85-3.92 (4H, m, H-1, OMe), 3.95 (3H, s, OMe), 4.11 (3H, s, OMe), 4.45-4.56 (2H, m, H-10, H-2), 4.78 (1H, dd, $J_1$=10.5 Hz, $J_2$=1.5 Hz, H-2), 6.87 (1H, s, H-4'), 7.01 (1H, s, H-3'), 7.38 (1H, m, H-8), 7.48 (1H, m, H-7), 7.63 (1H, d, J=8.4, H-9), 7.98 (1H, br. s, H-4), 8.31 (1H, d, J=8.7 Hz, H-6); MS (ESI) m/z=481 (M+H$^+$).

Example 5

Preparation of Agent 11 from Compound 10

A solution of compound 10 (67 mg, 0.153 mmol) in THF (10 ml) was warmed to 45° C., after which palladium (10% on carbon, 32.6 mg, 0.031 mmol) and ammonium formate (25% aqueous solution, 386 mg, 1.53 mmol) were added. The mixture was stirred for 2.5 h, cooled to RT, and filtered over Celite. The filtrate was concentrated, the crude product dissolved in 4 N HCl in ethyl acetate (6 ml), and the resultant mixture stirred for 2 h. Then, the mixture was concentrated and dried in vacuo to afford the intermediate (26.2 mg, 0.106 mmol) as an off-white solid. The intermediate (13.1 mg, 0.053 mmol) was dissolved in dry DMF (2 ml) and the solution was cooled to 0° C. Indole 6 (11.8 mg, 0.058 mmol) and EDC.HCl (30.4 mg, 0.159 mmol) were added. The mixture was stirred at RT for 18 h and then concentrated. The crude product was purified by column chromatography (DCM/MeOH, 19:1, 0.05% conc. HCl) to yield 11 (13.3 mg, 0.031 mmol, 58%) as a pale yellow solid. —$^1$H NMR (300 MHz, $CDCl_3$), δ (ppm): 2.61 (3H, s, Ac), 2.64 (3H, s, 9-Me), 3.07 (1H, t, J=10.8 Hz, H-10), 3.49 (1H, d, J=10.7 Hz, H-10), 4.06 (1H, m, H-1), 4.35 (1H, t, J=8.9 Hz, H-2), 4.60 (1H, d, J=10.2 Hz, H-2), 7.05 (1H, s, H-3'), 7.30-7.38 (3H, m, H-7, H-8, H-4'), 7.85 (1H, m, H-7'), 8.18 (1H, m, H-6'), 8.29 (2H, d, J=7.2 Hz, H-4, H-6); MS (ESI) m/z=433 (M+H⁺).

Example 6

Preparation of Agent 12 from Compound 10

A solution of compound 10 (67 mg, 0.153 mmol) in THF (10 ml) was warmed to 45° C., after which palladium (10% on carbon, 32.6 mg, 0.031 mmol) and ammonium formate (25% aqueous solution, 386 mg, 1.53 mmol) were added. The mixture was stirred for 2.5 h, cooled to RT, and filtered over Celite. The filtrate was concentrated, the crude product dissolved in 4 N HCl in ethyl acetate (6 ml), and the solution stirred for 2 h. Then, the mixture was concentrated and dried in vacuo to afford the intermediate (26.2 mg, 0.106 mmol) as an off-white solid. The intermediate (13.1 mg, 0.053 mmol) was dissolved in dry DMF (2 ml) and the solution was cooled to 0° C. Indole 8 (14.6 mg, 0.058 mmol) and EDC.HCl (30.4 mg, 0.159 mmol) were added. The mixture was stirred for 18 h at RT and then concentrated. The crude product was purified by column chromatography (DCM/MeOH, 19:1, 0.05% conc. HCl) to yield 12 (12.2 mg, 0.025 mmol, 48%) as a pale yellow solid. —¹H NMR (300 MHz, CDCl₃), δ (ppm): 2.67 (3H, s, 9-Me), 3.13 (1H, t, J=11.4 Hz, H-10), 3.50 (1H, d, J=11.1 Hz, H-10), 3.91 (3H, s, OMe), 3.97 (3H, s, OMe), 4.16 (4H, m, H-1, OMe), 4.53 (1H, t, J=8 Hz, H-2), 4.66 (1H, d, J=10.2 Hz, H-2), 6.77 (1H, s, H-4'), 6.88 (1H, d, J=2.1 Hz, H-3'), 7.24-7.33 (2H, m, H-7, H-8), 8.27 (1H, m, H-6), 8.52 (1H, s, H-4), 9.62 (1H, s, OH), 10.08 (1H, s, NH); MS (ESI) m/z=481 (M+H⁺).

REFERENCES

[1] Boger, D. L.; Johnson, D. S.; Wrasidlo, W. Bioorg. Med. Chem. Lett. 1994, 4, 631-636.
[2] McGovren, J. P., Clarke, G. L., Pratt, E. A., DeKoning, T. F. J. Antibiot. 1984, 37, 63-70.
[3] Carter, P.; Smith, L.; Ryan, M. Endocr.-Relat. Cancer 2004, 11, 659-687.
[4] Bagshawe, K. D. Drug Dev. Res. 1995, 34, 220-230.
[5] Melton, R.; Connors, T.; Knox, R. J. S.T.P. Pharma Sciences, 1999, 13-33.
[6] Huber, B. E.; Richards, C. A.; Krenitsky, T. A. Proc. Natl. Acad. Sci. USA, 1991, 88, 8039-8043.
[7] Bagshawe, K. D.; Springer, C. J.; Searle, F.; Antoniw, P.; Sharma, S. K.; Melton, R. G.; Sherwood, R. F. Br. J. Cancer, 1988, 58, 700-703.
[8] Duncan, R. Nat. Rev. Drug Discov. 2003, 2, 347-360.
[9] Tietze, L. F.; Lieb, M.; Herzig, T.; Haunert, F.; Schuberth, I. Bioorg. Med. Chem. 2001, 9, 1929-1939.
[10] Tietze, L. F., Herzig, T.; Fecher, A.; Haunert, F., Schuberth, I. ChemBioChem 2001, 758-765.
[11] Toki, B. E.; Cerveny, C. G.; Wahl, A. F.; Senter, P. D. J. Org. Chem., 2002, 67, 1866-1872.
[12] See for some recently disclosed cyclization spacers for example WO 2005/079398, WO 2005/105154, and WO 2006/012527.
[13] Greenwald, R. B., Choe, Y. H., McGuirc, J., Conover, C. D. Adv. Drug Delivery Rev. 2003, 55, 217-250.
[14] Kingsbury, W. D.; Boehm; J. C.; Mehta, R. J.; Grappel, S. F.; Gilvarg, C. J. Med. Chem. 1984, 27, 1447-1451.
[15] Greenwald, R. B.; Zhao, H.; Yang, K.; Reddy, P.; Martinez, A. J. Med. Chem. 2004, 47, 726-734.
[16] (a) Franke, A. E.; Sievers, E. L.; and Scheinberg, D. A. Cancer Biother. Radiopharm. 2000, 15, 459-476.
(b) Murray, J. L. Semin. Oncol. 2000, 27, 2564-2570 (c) Breitling, F., and Dubel, S., Recombinant Antibodies, John Wiley and Sons, New York, 1998.
[17] Ringsdorf, H. J. Polym. Sci., Polym. Symp. 1975, 51, 135-153.
[18] Elvira, C.; Gallardo, A.; San Roman, J.; Cifuentes, A. Molecules 2005, 10, 114-125.
[19] Remington's Pharmaceutical Science (15th ed., Mack Publishing, Easton, Pa., 1980) (incorporated by reference in its entirety for all purposes)

The invention claimed is:
1. A compound, which is

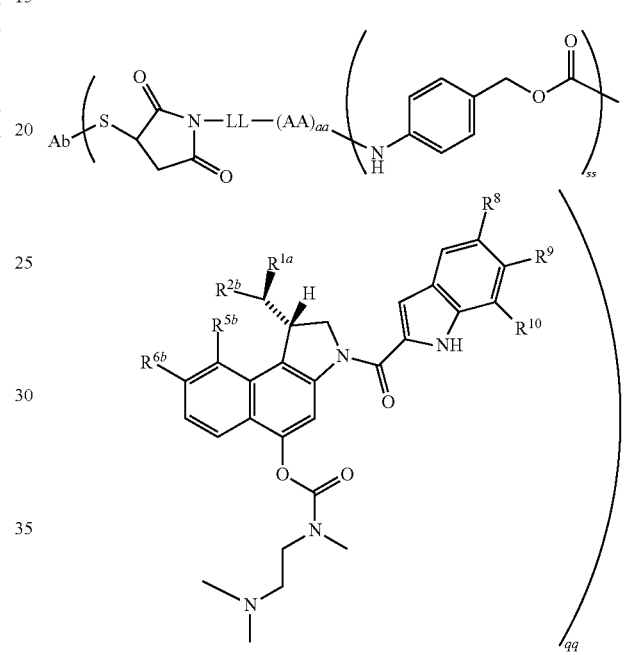

wherein $R^{1a}$ is selected from Cl and Br; $R^{2b}$ is hydrogen; $R^{5b}$ is selected from methyl, ethyl, propyl, isopropyl, nitro, F, Cl, Br, methoxy, amino, methylamino, hydroxymethyl, and dimethylamino; $R^{6b}$ is selected from H, tert-butyl, and isopropyl; $R^9$ and $R^{10}$ are both hydrogen and $R^8$ is selected from the group consisting of $N(R^h)C(O)R^i$, $N(R^h)C(O)OR^i$, and $N(R^h)C(O)N(R^i)R^j$, wherein $R^h$ is H, $R^i$ and $R^j$ are independently selected from H and optionally substituted $C_{3-15}$ cycloalkyl, $C_{1-15}$ heterocycloalkyl, $C_{6-15}$ aryl, or $C_{1-15}$ heteroaryl, one or more of the optional substitutents in $R^i$ and/or $R^j$ optionally being a water-soluble group, $(AA)_{aa}$ is selected from valylcitrulline, valyllysine, phenylalanyllysine, alanylphenylalanyllysine, and D-alanylphenylalanyllysine, ss is 1 or 2, LL is selected from

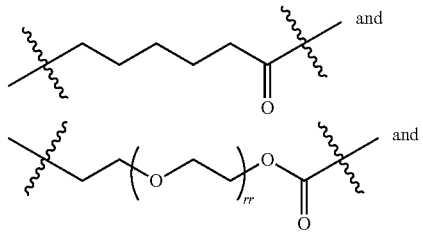

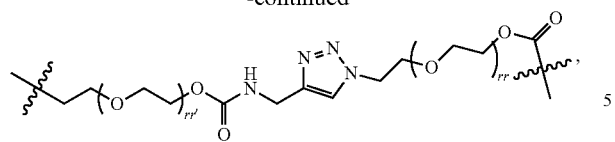

qq ranges from 1 to 20, rr and rr' each independently range from 1 to 4, and Ab is an antibody.

2. A pharmaceutical composition comprising a compound according to claim 1 and a pharmaceutically acceptable carrier.

3. The compound of claim 1, wherein said Ab is a full-length antibody, an F(ab')$_2$ fragment thereof, or an Fab fragment thereof.

4. The compound of claim 3, wherein said Ab is a monoclonal antibody.

5. The compound of claim 1, wherein $R^{6b}$ is hydrogen.

* * * * *

UNITED STATES PATENT AND TRADEMARK OFFICE
CERTIFICATE OF CORRECTION

PATENT NO.         : 9,901,567 B2
APPLICATION NO.    : 14/174794
DATED              : February 27, 2018
INVENTOR(S)        : Patrick Henry Beusker et al.

Page 1 of 1

It is certified that error appears in the above-identified patent and that said Letters Patent is hereby corrected as shown below:

Column 110, Lines 20-40 Claim 1:
The structure of the compound should appear as follows:

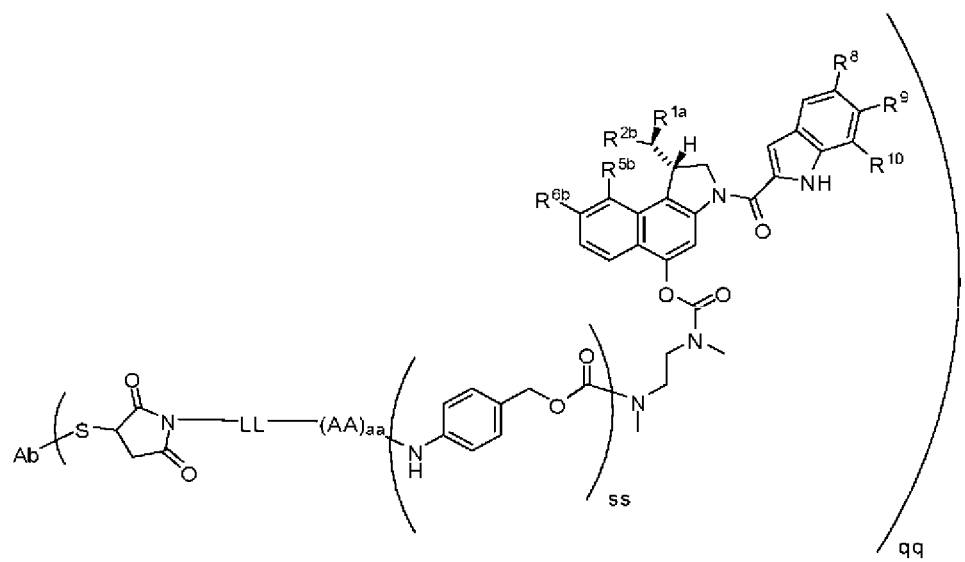

Signed and Sealed this
Nineteenth Day of June, 2018

Andrei Iancu
*Director of the United States Patent and Trademark Office*